(12) United States Patent
Davidson et al.

(10) Patent No.: US 11,766,399 B2
(45) Date of Patent: *Sep. 26, 2023

(54) METHOD AND SYSTEM FOR DRUG DELIVERY

(71) Applicant: Syqe Medical Ltd., Tel-Aviv (IL)

(72) Inventors: Perry Davidson, Tel-Aviv (IL); Aaron Schorr, Misgav (IL); Arie Holtz, Jerusalem (IL); Will Pong, Tehachapi, CA (US); Binyamin Schwartz, Sde Eliezer (IL)

(73) Assignee: Syqe Medical Ltd., Tel-Aviv (IL)

( * ) Notice: Subject to any disclaimer, the term of this patent is extended or adjusted under 35 U.S.C. 154(b) by 50 days.

This patent is subject to a terminal disclaimer.

(21) Appl. No.: 17/238,278

(22) Filed: Apr. 23, 2021

(65) Prior Publication Data

US 2021/0236414 A1 Aug. 5, 2021

Related U.S. Application Data

(63) Continuation of application No. 15/690,323, filed on Aug. 30, 2017, now Pat. No. 11,071,712, which is a continuation of application No. 13/997,302, filed as application No. PCT/IL2011/050071 on Dec. 22, 2011, now Pat. No. 9,775,379.

(60) Provisional application No. 61/425,962, filed on Dec. 22, 2010.

(51) Int. Cl.
| | |
|---|---|
| *A61K 9/00* | (2006.01) |
| *A61K 9/70* | (2006.01) |
| *A61M 11/04* | (2006.01) |
| *A61M 15/00* | (2006.01) |
| *A24F 40/50* | (2020.01) |
| *A61M 16/00* | (2006.01) |
| *G16H 20/13* | (2018.01) |
| *A24F 40/20* | (2020.01) |

(Continued)

(52) U.S. Cl.
CPC ............ *A61K 9/0004* (2013.01); *A24F 40/50* (2020.01); *A61K 9/007* (2013.01); *A61K 9/7007* (2013.01); *A61M 11/041* (2013.01); *A61M 11/042* (2014.02); *A61M 15/002* (2014.02); *A61M 15/0003* (2014.02); *A61M 15/008* (2014.02); *A61M 15/0016* (2014.02); *A61M 15/0045* (2013.01); *A61M 15/0051* (2014.02); *A61M 15/0055* (2014.02); *A61M 15/0065* (2013.01); *A61M 15/0066* (2014.02); *A61M 15/0081* (2014.02); *A61M 15/0083* (2014.02); *A24F 40/10* (2020.01); *A24F 40/20* (2020.01); *A24F 40/485* (2020.01); *A61M 11/048* (2014.02); *A61M 2016/0021* (2013.01); *A61M 2016/0039* (2013.01); *A61M 2202/062* (2013.01); *A61M 2205/12* (2013.01); *A61M 2205/13* (2013.01); *A61M 2205/17* (2013.01); *A61M 2205/18* (2013.01); *A61M 2205/276* (2013.01); *A61M 2205/3306* (2013.01); *A61M 2205/3331* (2013.01); *A61M 2205/3365* (2013.01); *A61M 2205/3368* (2013.01); *A61M 2205/3553* (2013.01); *A61M 2205/3584* (2013.01); *A61M 2205/3592* (2013.01); *A61M 2205/364* (2013.01); *A61M 2205/3606* (2013.01); *A61M 2205/368* (2013.01); *A61M 2205/3653* (2013.01); *A61M 2205/3673* (2013.01); *A61M 2205/502* (2013.01); *A61M 2205/52* (2013.01); *A61M 2205/581* (2013.01); *A61M 2205/583* (2013.01); *A61M 2205/587* (2013.01); *A61M 2205/60* (2013.01); *A61M 2205/6009* (2013.01); *A61M 2205/6018* (2013.01); *A61M 2205/6054* (2013.01); *A61M 2205/6063* (2013.01); *A61M 2205/6072* (2013.01); *A61M 2205/8206* (2013.01); *A61M 2207/00* (2013.01); *A61M 2209/06* (2013.01); *A61M 2209/10* (2013.01); *G16H 20/13* (2018.01)

(58) Field of Classification Search
CPC ... A61K 9/7007; A24F 40/20; A61M 2207/00
See application file for complete search history.

(56) References Cited

U.S. PATENT DOCUMENTS

| | | | |
|---|---|---|---|
| 3,203,432 | A | 8/1965 | Green et al. |
| 3,894,544 | A | 7/1975 | Egri |

(Continued)

FOREIGN PATENT DOCUMENTS

| | | |
|---|---|---|
| AU | 199641966 | 5/1996 |
| AU | 708269 | 7/1999 |

(Continued)

OTHER PUBLICATIONS

Grasscity forums (How to Make Hash? Discussion in 'Apprentice Marijuana Consumption' started by Juggalobud, Nov. 1, 2002) (Year: 2002).*

(Continued)

*Primary Examiner* — Mark V Stevens

(57) ABSTRACT

There is provided in accordance with an exemplary embodiment of the invention, a device and a method for controlled extraction of at least one active substance from at least one type of plant matter by application of heat, the device comprising: a heating element adapted to apply heat to an area of the plant matter to extract the substance; and a mechanism adapted for moving the plant matter relative to the heating element. Optionally, the active substance is a restricted substance. There is also provided in accordance with an exemplary embodiment of the invention, a method of monitoring and controlling inhalation of a restricted substance. There is provided in accordance with an exemplary embodiment of the invention, a method of manufacturing a tape of plant matter comprising an active substance.

17 Claims, 23 Drawing Sheets

(51) Int. Cl.
  *A24F 40/485*  (2020.01)
  *A24F 40/10*  (2020.01)

(56) References Cited

U.S. PATENT DOCUMENTS

| | | | |
|---|---|---|---|
| 4,603,030 | A | 7/1986 | McCarthy |
| 4,735,358 | A | 4/1988 | Morita et al. |
| 4,966,171 | A | 10/1990 | Serrano et al. |
| 4,969,477 | A | 11/1990 | Yagisawa |
| 5,023,020 | A | 6/1991 | Machida et al. |
| 5,086,978 | A | 2/1992 | Fertig |
| 5,105,838 | A | 4/1992 | White et al. |
| 5,301,666 | A | 4/1994 | Lerk et al. |
| 5,333,106 | A | 7/1994 | Lanpher et al. |
| 5,388,594 | A | 2/1995 | Counts et al. |
| 5,404,871 | A | 4/1995 | Goodman et al. |
| 5,443,606 | A | 8/1995 | Hassenboehler, Jr. et al. |
| 5,479,948 | A | 1/1996 | Counts et al. |
| 5,503,869 | A | 4/1996 | Van Oort |
| 5,546,965 | A | 8/1996 | White |
| 5,565,148 | A | 10/1996 | Pendergrass, Jr. |
| 5,649,554 | A | 7/1997 | Sprinkel et al. |
| 5,655,520 | A | 8/1997 | Howe et al. |
| 5,792,057 | A | 8/1998 | Rubsamen et al. |
| 5,805,768 | A | 9/1998 | Schwartz et al. |
| 5,819,756 | A | 10/1998 | Mielordt |
| 5,855,564 | A | 1/1999 | Ruskewicz |
| 6,547,229 | B1 | 4/2003 | Hanson et al. |
| 6,703,418 | B2 | 3/2004 | Plasse |
| 6,713,024 | B1 | 3/2004 | Amell et al. |
| 6,761,164 | B2 | 7/2004 | Amirpour et al. |
| 6,871,647 | B2 | 3/2005 | Allan et al. |
| 7,088,914 | B2 | 8/2006 | Whittle et al. |
| 7,169,378 | B2 | 1/2007 | Rabinowitz et al. |
| 7,287,530 | B1 | 10/2007 | Stuart |
| 7,376,344 | B2 | 5/2008 | Manne |
| 7,389,943 | B2 | 6/2008 | Jaworski |
| 7,537,005 | B2 | 5/2009 | Dave |
| 7,690,076 | B2 | 6/2010 | Tannous |
| 7,987,846 | B2 | 8/2011 | Hale et al. |
| 8,235,037 | B2 | 8/2012 | Hale et al. |
| 8,408,200 | B2 | 4/2013 | Clark et al. |
| 8,490,627 | B2 | 7/2013 | Levin et al. |
| 8,615,407 | B2 | 12/2013 | Hyde et al. |
| 9,775,379 | B2 | 10/2017 | Davidson et al. |
| 9,802,011 | B2 | 10/2017 | Davidson et al. |
| 9,943,114 | B2 | 4/2018 | Batista |
| 9,993,602 | B2 | 6/2018 | Davidson et al. |
| 10,080,851 | B2 | 9/2018 | Davidson et al. |
| 10,179,215 | B2 | 1/2019 | Raichman |
| 10,299,515 | B2 | 5/2019 | Krietzmam |
| 11,044,950 | B2 | 6/2021 | Collett et al. |
| 2001/0027789 | A1 | 10/2001 | Goede et al. |
| 2002/0078951 | A1 | 6/2002 | Nichols et al. |
| 2002/0168322 | A1 | 11/2002 | Clark et al. |
| 2003/0037785 | A1 | 2/2003 | Sonntag |
| 2003/0041859 | A1 | 3/2003 | Abrams et al. |
| 2003/0049025 | A1 | 3/2003 | Neumann et al. |
| 2003/0062042 | A1 | 4/2003 | Wensley et al. |
| 2003/0136420 | A1 | 7/2003 | Kraker |
| 2003/0163099 | A1 | 8/2003 | Wermeling et al. |
| 2003/0168057 | A1 | 9/2003 | Snyder et al. |
| 2003/0200964 | A1 | 10/2003 | Blakley et al. |
| 2004/0045567 | A1 | 3/2004 | Lewis et al. |
| 2004/0069798 | A1 | 4/2004 | Grey et al. |
| 2004/0084044 | A1 | 5/2004 | Childers et al. |
| 2004/0099266 | A1 | 5/2004 | Cross et al. |
| 2004/0188546 | A1 | 9/2004 | Tabata et al. |
| 2004/0192760 | A1 | 9/2004 | Whittle et al. |
| 2004/0234699 | A1 | 11/2004 | Hale et al. |
| 2005/0063686 | A1 | 3/2005 | Whittle et al. |
| 2005/0126562 | A1 | 6/2005 | Rabinowitz et al. |
| 2005/0244521 | A1 | 11/2005 | Strickland et al. |
| 2005/0268909 | A1 | 12/2005 | Bonney et al. |
| 2005/0268911 | A1 | 12/2005 | Cross et al. |
| 2006/0102175 | A1 | 5/2006 | Nelson |
| 2006/0120962 | A1 | 6/2006 | Rabinowitz et al. |
| 2006/0157491 | A1 | 7/2006 | Whittle et al. |
| 2006/0167084 | A1 | 7/2006 | Dudley |
| 2006/0258738 | A1 | 11/2006 | Dieterich |
| 2007/0023060 | A1 | 2/2007 | Ra |
| 2007/0072938 | A1 | 3/2007 | Rose |
| 2007/0122353 | A1 | 3/2007 | Hale et al. |
| 2007/0074721 | A1 | 4/2007 | Harmer et al. |
| 2007/0102013 | A1 | 5/2007 | Adams et al. |
| 2007/0163580 | A1 | 7/2007 | Braithwaite |
| 2007/0209661 | A1 | 9/2007 | Smyth et al. |
| 2007/0240712 | A1 | 10/2007 | Fleming et al. |
| 2007/0286816 | A1 | 12/2007 | Hale et al. |
| 2008/0072898 | A1 | 3/2008 | Quoniam |
| 2008/0078382 | A1 | 4/2008 | LeMahieu et al. |
| 2008/0140250 | A1 | 6/2008 | Dave |
| 2008/0159961 | A1 | 7/2008 | Woolfe et al. |
| 2008/0176885 | A1 | 7/2008 | Holtman et al. |
| 2008/0181942 | A1 | 7/2008 | Zajicek |
| 2008/0199161 | A1 | 8/2008 | Hickey et al. |
| 2008/0202515 | A1 | 8/2008 | Hodson et al. |
| 2008/0299048 | A1 | 12/2008 | Hale et al. |
| 2008/0308101 | A1 | 12/2008 | Spandorfer |
| 2008/0311176 | A1 | 12/2008 | Hale et al. |
| 2009/0084865 | A1 | 4/2009 | Maharaj |
| 2009/0151722 | A1 | 6/2009 | Eason et al. |
| 2009/0194105 | A1 | 8/2009 | Besseler et al. |
| 2009/0197941 | A1 | 8/2009 | Guy et al. |
| 2009/0241949 | A1 | 10/2009 | Smutney et al. |
| 2009/0293888 | A1 | 12/2009 | Williams et al. |
| 2009/0293892 | A1 | 12/2009 | Williams et al. |
| 2009/0308390 | A1 | 12/2009 | Smutney et al. |
| 2009/0320836 | A1 | 12/2009 | Baker, Jr. |
| 2010/0012118 | A1 | 1/2010 | Storz |
| 2010/0035978 | A1 | 2/2010 | Guy et al. |
| 2010/0154795 | A1 | 6/2010 | Pentafragas |
| 2010/0168228 | A1 | 7/2010 | Bose |
| 2010/0181387 | A1 | 7/2010 | Zaffaroni et al. |
| 2010/0204602 | A1 | 8/2010 | Addington et al. |
| 2010/0250280 | A1 | 9/2010 | Sutherland |
| 2010/0294278 | A1 | 11/2010 | Mosier et al. |
| 2010/0300442 | A1 | 12/2010 | Houzego et al. |
| 2010/0326438 | A1 | 12/2010 | Dunne |
| 2011/0030706 | A1 | 2/2011 | Gibson et al. |
| 2011/0036346 | A1 | 2/2011 | Cohen et al. |
| 2011/0038958 | A1 | 2/2011 | Kikuchi et al. |
| 2011/0126831 | A1 | 6/2011 | Fernandez Pernia |
| 2011/0240011 | A1 | 10/2011 | Caldwell |
| 2011/0244020 | A1 | 10/2011 | Hale et al. |
| 2011/0265806 | A1 | 11/2011 | Alarcon et al. |
| 2012/0003318 | A1 | 1/2012 | Schuler et al. |
| 2012/0006700 | A1 | 1/2012 | Geboers et al. |
| 2012/0116241 | A1 | 5/2012 | Shie et al. |
| 2012/0252885 | A1 | 10/2012 | Barbato |
| 2012/0255546 | A1 | 10/2012 | Goetz et al. |
| 2012/0291791 | A1 | 11/2012 | Pradeep |
| 2012/0304990 | A1* | 12/2012 | Todd .......... A61M 11/042 128/203.14 |
| 2012/0325227 | A1 | 12/2012 | Robinson et al. |
| 2013/0032139 | A1 | 2/2013 | Hale et al. |
| 2013/0053719 | A1 | 2/2013 | Wekell |
| 2013/0081623 | A1 | 4/2013 | Buchberger |
| 2013/0087144 | A1 | 4/2013 | Todd |
| 2013/0112197 | A1 | 5/2013 | Kruener et al. |
| 2013/0213397 | A1 | 8/2013 | Curtis et al. |
| 2013/0276799 | A1 | 10/2013 | Davidson et al. |
| 2013/0304990 | A1 | 11/2013 | Bass et al. |
| 2013/0333700 | A1 | 12/2013 | Buchberger |
| 2014/0037794 | A1 | 2/2014 | Patera et al. |
| 2014/0060525 | A1 | 3/2014 | Hale et al. |
| 2014/0088045 | A1 | 3/2014 | Rigas et al. |
| 2014/0100249 | A1 | 4/2014 | Sears et al. |
| 2014/0106324 | A1 | 4/2014 | Adams et al. |
| 2014/0144429 | A1 | 5/2014 | Wensley et al. |
| 2014/0190496 | A1 | 7/2014 | Wensley et al. |
| 2014/0202454 | A1 | 7/2014 | Buchberger |
| 2014/0209105 | A1 | 7/2014 | Sears et al. |
| 2014/0238423 | A1 | 8/2014 | Tucker et al. |

(56) References Cited

U.S. PATENT DOCUMENTS

| | | |
|---|---|---|
| 2014/0366898 A1 | 12/2014 | Monsees et al. |
| 2015/0064672 A1 | 3/2015 | Bars |
| 2015/0075521 A1 | 3/2015 | Lee et al. |
| 2015/0090253 A1 | 4/2015 | Farrow |
| 2015/0122252 A1 | 5/2015 | Frija |
| 2015/0136124 A1 | 5/2015 | Aronie et al. |
| 2015/0237913 A1 | 8/2015 | Suzuki et al. |
| 2016/0007653 A1 | 1/2016 | Tu |
| 2016/0044960 A1 | 2/2016 | O'Connor |
| 2016/0100624 A1 | 4/2016 | Yilmaz et al. |
| 2016/0121057 A1 | 5/2016 | Dyche et al. |
| 2016/0166564 A1 | 6/2016 | Myers et al. |
| 2016/0166786 A1 | 6/2016 | Kinzer |
| 2016/0171164 A1 | 6/2016 | Kinzer |
| 2016/0183589 A1 | 6/2016 | Born et al. |
| 2016/0271347 A1 | 9/2016 | Raichman |
| 2016/0286860 A1 | 10/2016 | Flayler |
| 2016/0295922 A1 | 10/2016 | John et al. |
| 2016/0309784 A1 | 10/2016 | Silvestrini et al. |
| 2016/0331022 A1 | 11/2016 | Cameron |
| 2016/0331913 A1 | 11/2016 | Bourque |
| 2016/0345630 A1 | 12/2016 | Mironov et al. |
| 2016/0354573 A1 | 12/2016 | Buswell et al. |
| 2017/0095624 A1 | 4/2017 | Davidson et al. |
| 2017/0106153 A1 | 4/2017 | Davidson et al. |
| 2017/0119979 A1 | 5/2017 | Davidson et al. |
| 2017/0119981 A1 | 5/2017 | Davidson et al. |
| 2017/0127727 A1 | 5/2017 | Davidson et al. |
| 2017/0136196 A1 | 5/2017 | Davidson et al. |
| 2017/0150755 A1 | 6/2017 | Batista |
| 2017/0157343 A1 | 6/2017 | Davidson et al. |
| 2017/0164657 A1 | 6/2017 | Batista |
| 2017/0203058 A1 | 7/2017 | Davidson et al. |
| 2017/0295848 A1 | 10/2017 | LaMothe |
| 2017/0360089 A1 | 12/2017 | Davidson et al. |
| 2018/0110943 A1 | 4/2018 | Raichman |
| 2018/0318529 A1 | 11/2018 | Davidson et al. |
| 2018/0344954 A1 | 12/2018 | Davidson et al. |
| 2019/0001087 A1 | 1/2019 | Davidson et al. |
| 2019/0009039 A1 | 1/2019 | Davidson et al. |
| 2019/0015382 A1 | 1/2019 | Davidson et al. |
| 2019/0290862 A1 | 9/2019 | Davidson et al. |
| 2021/0023316 A1 | 1/2021 | Schorr et al. |
| 2021/0402109 A1 | 12/2021 | Landa et al. |
| 2022/0031972 A1 | 2/2022 | Davidson et al. |
| 2022/0096760 A1 | 3/2022 | Schwartz et al. |
| 2022/0183962 A1 | 6/2022 | Davidson et al. |
| 2022/0211958 A1 | 7/2022 | Davidson |
| 2022/0241523 A1 | 8/2022 | Davidson et al. |

FOREIGN PATENT DOCUMENTS

| | | | | |
|---|---|---|---|---|
| CA | 2599022 | 9/2005 | | |
| CA | 3025407 | 11/2017 | | |
| CN | 1323231 | 11/2001 | | |
| CN | 2816102 | 9/2006 | | |
| CN | 1925883 | 3/2007 | | |
| CN | 101053685 | 10/2007 | | |
| CN | 101130121 | 2/2008 | | |
| CN | 101132823 | 2/2008 | | |
| CN | 101360528 | 2/2009 | | |
| CN | 101415457 | 4/2009 | | |
| CN | 101980743 | 2/2011 | | |
| CN | 102355914 | 2/2012 | | |
| CN | 102438602 | 5/2012 | | |
| CN | 203166473 | 8/2013 | | |
| CN | 106659858 | 5/2017 | | |
| CN | 108260855 | 7/2018 | | |
| CN | 108712918 | 10/2018 | | |
| EA | 201100197 | 3/2012 | | |
| EP | 0216926 | 3/1991 | | |
| EP | 0539674 | 5/1993 | | |
| EP | 0547429 | 6/1993 | | |
| EP | 1358902 | 11/2003 | | |
| EP | 2145643 | 1/2010 | | |
| EP | 2292108 | 3/2011 | | |
| EP | 3160553 | 5/2017 | | |
| GB | 2108390 | 5/1983 | | |
| GB | 2340758 | 3/2000 | | |
| GB | 2456183 | 7/2009 | | |
| GB | 2495771 | 4/2013 | | |
| JP | 2002-527151 | 8/2002 | | |
| JP | 2003-503117 | 1/2003 | | |
| JP | 2003-079731 | 3/2003 | | |
| JP | 2003-275214 | 9/2003 | | |
| JP | 2004-283609 | 10/2004 | | |
| JP | 2004-298331 | 10/2004 | | |
| JP | 2005-503846 | 2/2005 | | |
| JP | 2005-516644 | 6/2005 | | |
| JP | 2005-516647 | 6/2005 | | |
| JP | 2006-507909 | 3/2006 | | |
| JP | 2007-0516015 | 6/2007 | | |
| JP | 2008-501406 | 1/2008 | | |
| JP | 2008-301847 | 12/2008 | | |
| JP | 2009-509523 | 3/2009 | | |
| JP | 2009-131686 | 6/2009 | | |
| JP | 2011-508765 | 3/2011 | | |
| JP | 2012-110499 | 6/2012 | | |
| JP | 2012-527329 | 11/2012 | | |
| JP | 2013-521075 | 6/2013 | | |
| JP | 2013-523395 | 6/2013 | | |
| JP | 2020-062479 | 4/2020 | | |
| KR | 10-1319228 | 10/2013 | | |
| RU | 2413544 | 3/2011 | | |
| RU | 107026 | 8/2011 | | |
| RU | 2460677 | 9/2012 | | |
| RU | 2017102234 | 7/2018 | | |
| WO | WO 1991011120 A1 * | 8/1991 | ............ | A24C 5/392 |
| WO | WO 94/09842 | 5/1994 | | |
| WO | WO 96/32854 | 10/1996 | | |
| WO | WO 98/04308 | 2/1998 | | |
| WO | WO 2008/116165 | 9/1998 | | |
| WO | WO 00/21594 | 4/2000 | | |
| WO | WO 00/21598 | 4/2000 | | |
| WO | WO 00/24362 | 5/2000 | | |
| WO | WO 01/00263 | 1/2001 | | |
| WO | WO 01/17595 | 3/2001 | | |
| WO | WO 03/020057 | 3/2003 | | |
| WO | WO 03/030979 A1 | 4/2003 | | |
| WO | WO 03/037412 | 5/2003 | | |
| WO | WO 2005/06103 3 | 7/2005 | | |
| WO | WO 2005/072719 | 8/2005 | | |
| WO | WO 2005/072792 | 8/2005 | | |
| WO | WO 2005/120614 | 12/2005 | | |
| WO | WO 2007/018568 | 2/2007 | | |
| WO | WO 2007/042941 | 4/2007 | | |
| WO | WO 2008/024408 | 2/2008 | | |
| WO | WO 2008/024490 | 2/2008 | | |
| WO | WO 2009/102976 | 8/2009 | | |
| WO | WO 2009/124552 | 10/2009 | | |
| WO | WO 2010/015260 | 2/2010 | | |
| WO | WO 2011/073306 | 6/2011 | | |
| WO | WO2011/130183 | 10/2011 | | |
| WO | WO 2012/006125 | 1/2012 | | |
| WO | WO 2012/006126 | 1/2012 | | |
| WO | WO 2012/026963 | 3/2012 | | |
| WO | WO 2012/038903 | 3/2012 | | |
| WO | WO 2012/085919 | 6/2012 | | |
| WO | WO 2013/013808 | 1/2013 | | |
| WO | WO 2013/057185 | 4/2013 | | |
| WO | WO 2013/060781 | 5/2013 | | |
| WO | WO 2013/083636 | 6/2013 | | |
| WO | WO 2014/037794 | 3/2014 | | |
| WO | WO 2014/061477 | 4/2014 | | |
| WO | WO 2014/085719 | 6/2014 | | |
| WO | WO 2015/123064 | 8/2015 | | |
| WO | WO 2015/123317 | 8/2015 | | |
| WO | WO 2015/175979 | 11/2015 | | |
| WO | WO 2016/001921 | 1/2016 | | |
| WO | WO 2016/001922 | 1/2016 | | |
| WO | WO 2016/001923 | 1/2016 | | |
| WO | WO 2016/001924 | 1/2016 | | |
| WO | WO 2016/001925 | 1/2016 | | |
| WO | WO 2016/001926 | 1/2016 | | |

(56) References Cited

FOREIGN PATENT DOCUMENTS

| | | |
|---|---|---|
| WO | WO 2016/090303 | 6/2016 |
| WO | WO 2016/147188 | 9/2016 |
| WO | WO 2016/172802 | 11/2016 |
| WO | WO 2016/187696 | 12/2016 |
| WO | WO 2017/118980 | 7/2017 |
| WO | WO 2017/122196 | 7/2017 |
| WO | WO 2017/122201 | 7/2017 |
| WO | WO 2017/178958 | 10/2017 |
| WO | WO 2017/185051 | 10/2017 |
| WO | WO 2018/019855 | 2/2018 |
| WO | WO 2019/159170 | 8/2019 |
| WO | WO 2020/089890 | 5/2020 |
| WO | WO 2020/161721 | 8/2020 |
| WO | WO 2013/052586 | 3/2021 |

OTHER PUBLICATIONS

Verilife (Cannabis Trichromes:What are they & what do they do? https://www.verilife.com/blog/trichomes, 2021) (Year: 2021).*

UNODC (Recommended methods for the identification and analysis of cannabis and cannabis products, Sep. 2009, United Nations publication, pp. 1-50) (Year: 2009).*

Requisition by the Examiner Dated Apr. 4, 2022 From the Innovation, Science and Economic Development Canada, Canadian Intellectual Property Office Re. Application No. 2,953.074 with Claims. (11 Pages).

Notice of Reasons for Rejection dated May 24, 2022 From the Japan Patent Office Re. Application No. 2020-134166 and Its Translation Into English. (10 Pages).

Examination Report dated Apr. 20, 2021 From the Instituto Mexicano de la Propiedad Industrial, Direccion Divisional de Patentes Re. Application No. MX/a/2017/000057 together with an English Summary. (5 Pages).

Requisition by the Examiner dated May 25, 2022 From the Innovation, Science and Economic Development Canada, Canadian Intellectual Property Office Re. Application No. 3,114,582. (3 Pages).

International Preliminary Report on Patentability dated Aug. 19, 2021 From the International Bureau of WIPO Re. Application No. PCT/IL2020/050151. (7 Pages).

Notice of Allowance dated Dec. 1, 2021 from the US Patent and Trademark Office Re. U.S. Appl. No. 16/030,967. (21 pages).

Patent Examination Report dated Oct. 26, 2021 From the Australian Government, IP Australia Re. Application No. 2017204945. (3 Pages).

Notification of Office Action dated Jun. 23, 2022 From the State Intellectual Property Office of the People's Republic of China Re. Application No. 20200101980.3. (8 Pages).

Requisition by the Examiner dated Sep. 28, 2021 From the Innovation, Science and Economic Development Canada, Canadian Intellectual Property Office Re. Application No. 2,953,069. (4 Pages).

Applicant-Initiated Interview Summary dated Apr. 5, 2018 From the US Patent and Trademark Office Re. U.S. Appl. No. 15/391,896. (3 pages).

Applicant-Initiated Interview Summary dated Jan. 5, 2018 From the US Patent and Trademark Office Re. U.S. Appl. No. 15/382,819. (3 pages).

Applicant-Initiated Interview Summary dated Dec. 22, 2017 From the US Patent and Trademark Office Re. U.S. Appl. No. 15/312,647. (3 pages).

Applicant-Initiated Interview Summary dated Dec. 22, 2017 From the US Patent and Trademark Office Re. U.S. Appl. No. 15/362,883. (3 pages).

Applicant-Initiated Interview Summary dated Mar. 22, 2018 From the US Patent and Trademark Office Re. U.S. Appl. No. 15/308,370. (5 pages).

Applicant-Initiated Interview Summary dated May 22, 2017 From the US Patent and Trademark Office Re. U.S. Appl. No. 15/386,182. (3 pages).

Applicant-Initiated Interview Summary dated May 23, 2017 From the US Patent and Trademark Office Re. U.S. Appl. No. 15/362,841. (3 pages).

Applicant-Initiated Interview Summary dated May 23, 2017 From the US Patent and Trademark Office Re. U.S. Appl. No. 15/362,883. (3pages).

Applicant-Initiated Interview Summary dated May 23, 2017 From the US Patent and Trademark Office Re. U.S. Appl. No. 15/375,098. (3 pages).

Applicant-Initiated Interview Summary dated May 23, 2017 From the US Patent and Trademark Office Re. U.S. Appl. No. 15/382,819. (3 pages).

Applicant-Initiated Interview Summary dated Dec. 30, 2019 From the US Patent and Trademark Office Re. U.S. Appl. No. 15/690,323. (4 pages).

Communication Pursuant to Article 94(3) EPC dated Sep. 2, 2020 From the European Patent Office Re. Application No. 15756490.7. (5 Pages).

Communication Pursuant to Article 94(3) EPC dated Aug. 4, 2020 From the European Patent Office Re. Application No. 15815982.2. (5 Pages).

Communication Pursuant to Article 94(3) EPC dated Sep. 5, 2018 From the European Patent Office Re. Application No. 15744363.1. (4 Pages).

Communication Pursuant to Article 94(3) EPC dated Feb. 6, 2019 From the European Patent Office Re. Application No. 15753782.0. (6 Pages).

Communication Pursuant to Article 94(3) EPC dated Nov. 12, 2018 From the European Patent Office Re. Application No. 15814472.5. (5 Pages).

Communication Pursuant to Article 94(3) EPC dated Nov. 12, 2018 From the European Patent Office Re. Application No. 15815982.2. (4 Pages).

Communication Pursuant to Article 94(3) EPC dated Jan. 19, 2018 From the European Patent Office Re. Application No. 15744363.1. (4 Pages).

Communication Pursuant to Article 94(3) EPC dated Nov. 19, 2018 From the European Patent Office Re. Application No. 15756490.7. (4 Pages).

Communication Pursuant to Article 94(3) EPC dated Jan. 22, 2018 From the European Patent Office Re. Application No. 15756490.7. (4 Pages).

Communication Pursuant to Article 94(3) EPC dated Jun. 23, 2017 From the European Patent Office Re. Application No. 11815728.8. (5 Pages).

Communication Pursuant to Article 94(3) EPC dated Apr. 26, 2018 From the European Patent Office Re. Application No. 11815728.8. (4 Pages).

Communication Pursuant to Article 94(3) EPC dated Feb. 26, 2018 From the European Patent Office Re. Application No. 15753782.0. (6 Pages).

Communication Relating to the Results of the Partial International Search dated May 18, 2012 From the International Searching Authority Re. Application No. PCT/IL2011/050071.

Communication Relating to the Results of the Partial International Search dated Oct. 22, 2015 From the International Searching Authority Re. Application No. PCT/IL2015/050673.

Communication Relating to the Results of the Partial International Search dated Sep. 24, 2015 From the International Searching Authority Re. Application No. PCT/IL2015/050677.

Decision of Rejection dated Sep. 17, 2019 From the Japan Patent Office Re. Application No. 2016-576068 and Its Translation Into English. (12 Pages).

Decision of Rejection dated Aug. 27, 2019 From the Japan Patent Office Re. Application No. 2016-576071 and Its Translation Into English. (8 Pages).

(56) References Cited

OTHER PUBLICATIONS

Decision to Grant a Patent for Invention and Search Report dated Oct. 29, 2019 From the (ROSPATENT), Federal Government Institution of Industrial Property of the Federal Service of Intellectual Property, Patents and Trademark of the Russian Federation Re. Application No. 2019115942.and Its Translation Into English. (16 Pages).
Decision to Grant a Patent for Invention dated Mar. 25, 2019 From the Federal Goverment Institution, Federal Institute of Industrial Property of the Federal Sendee for Intellectual Property, Patents and Trademarks, ROSPATENT of the Russian Federation Re. Application No. 2017102236 and Its Translation Into English. (18 Pages).
Decision to Grant a Patent for invention dated Mar. 25, 2019 From the Federal Government Institution, Federal Institute of industrial Property of the Federal Service for Intellectual Property, Patents and Trademarks, ROSPATENT of the Russian Federation Re. Application No. 2017102235 and Its Translation Into English. (16 Pages).
Decision to Grant a Patent for Invention dated Mar. 25, 2019 From the Federal Government Institution, Federal Institute of Industrial Property of the Federal Service of Intellectual Property, Patents and Trademarks, ROSPATENT of the Russian Federation Re. Application No. 2017102233 and Its Translation Into English. (17 Pages).
European Search Report and the European Search Opinion dated Jul. 5, 2019 From the European Patent Office Re. Application No. PCT/19165448.2. (7 Pages).
European Search Report and the European Search Opinion dated Apr. 8, 2021 From the European Patent Office Re. Application No. 21159548.3. (7 Pages).
European Search Report and the European Search Opinion dated Nov. 20, 2020 From the European Patent Office Re. Application No. 20192870.2. (7 Pages).
European Search Report and the European Search Opinion dated Apr. 22, 2021 From the European Patent Office Re. Application No. 20192870.2. (14 Pages).
European Search Report and the European Search Opinion dated Mar. 26, 2020 From the European Patent Office Re. Application No. 20150198.8. (9 Pages).
Examination Report dated Feb. 5, 2020 From the Instituti Mexicano de la Propiedad Industrial, IMPI, Direction Divisional de Patentes Re. Application No. MX/a/2017/000056 and Its Translation Into English. (4 Pages).
Examination Report dated Apr. 8, 2019 From the Australian Government, IP Australia Re. Application No. 2015283589. (5 Pages).
Examination Report dated Jan. 13, 2021 From the Instituto Mexicano de la Propiedad Industrial, Secretario de Economia, Dioreccion Divisional de Patentes Re. Application No. MX/a/2017/000057. (6 Pages).
Examination Report dated Sep. 14, 2020 From the Australian Government, IP Australia Re. Application No. 2019229369, (4 Pages).
Examination Report dated Jan. 15, 2019 From the Australian Government, IP Australia Re. Application No. 2015283594. (4 Pages).
Examination Report dated Feb. 20, 2020 From the Australian Government, IP Australia Re. Application No. 2015283590. (6 Pages).
Examination Report dated Jan. 21, 2019 From the Australian Government, IP Australia Re. Application No. 2015283593. (4 Pages).
Examination Report dated Mar. 29, 2019 From the Australian Government, IP Australia Re. Application No. 2015283590. (5 Pages).
Examination Report dated Jan. 30, 2020 From the Instituto Mexicano de la Propiedade Industrial. IMPI, Direction Divisional de Patentes Re. Application No. MX/a/2017/000055 and Its Translation Into English. (5 Pages).
Examiner-Initiated Interview Summary dated Nov. 2, 2017 From the US Patent and Trademark Office Re. U.S. Appl. No. 15/382,819. (2 pages).
Final Official Action dated Feb. 22, 2021 From the US Patent and Trademark Office Re. U.S. Appl. No. 16/131,079, (60 Pages).
Final Official Action dated May 4, 2020 from the US Patent and Trademark Office Re. U.S. Appl. No. 15/690,323. (55 pages).
International Preliminary Report on Patentability dated Jul. 2, 2013 From the International Preliminary Examining Authority Re. Application No. PCT/IL2011/050071.
International Preliminary Report on Patentability dated Jan. 12, 2017 From the International Bureau of WIPO Re. Application No. PCT/IL2015/050673. (15 Pages).
International Preliminary Report on Patentability dated Jan. 12, 2017 From the International Bureau of WIPO Re. Application No. PCT/IL2015/050674. (11 Pages).
International Preliminary Report on Patentability dated Jan. 12, 2017 From the International Bureau of WIPO Re. Application No. PCT/IL2015/050675. (8 Pages).
International Preliminary Report on Patentability dated Jan. 12, 2017 From the International Bureau of WIPO Re. Application No. PCT/IL2015/050677. (13 Pages).
International Preliminary Report on Patentability dated Jan. 12, 2017 From the International Bureau of WIPO Re. Application No. PCT/IL2015/050678. (12 Pages).
International Preliminary Report on Patentability dated Jan. 12, 2017 From the International Bureau of WIPO Re. Application No. PCT/IL2015/50676. (11 Pages).
International Preliminary Report on Patentability dated Jul. 19, 2018 From the International Bureau of WIPO Re. Application No. PCT/IL2017/050014. (10 Pages).
International Preliminary Report on Patentability dated Aug. 27, 2020 From the International Bureau of WIPO Re. Application No. PCT/IL2019/050178. (8 Pages).
International Search Report and the Written Opinion dated Feb. 2, 2016 From the International Searching Authority Re. Application No. PCT/TL2015/050673.
International Search Report and the Written Opinion dated Dec. 3, 2015 From the International Searching Authority Re. Application No. PCT/IL2015/050677.
International Search Report and the Written Opinion dated May 3, 2020 From the International Searching Authority Re. Application No. PCT/IL2020/050151. (18 Pages).
International Search Report and the Written Opinion dated Jan. 7, 2016 From the International Searching Authority Re. Application No. PCT/IL2015/050675.
International Search Report and the Written Opinion dated Dec. 10, 2015 From the International Searching Authority Re. Application No. PCT/IL2015/050674.
International Search Report and the Written Opinion dated Oct. 19, 2012 From the International Searching Authority Re. Application No. PCT/IL2011/050071.
International Search Report and the Written Opinion dated Jan. 20, 2016 From the International Searching Authority Re. Application No. PCT/IL2015/50676.
International Search Report and the Written Opinion dated Oct. 22, 2015 From the International Searching Authority Re. Application No. PCT/IL2015/050678.
International Search Report and the Written Opinion dated May 23, 2019 From the International Searching Authority Re. Application No. PCT/IL2019/050178. (15 Pages).
International Search Report and the Written Opinion dated Mar. 27, 2017 From the International Searching Authority Re. Application No. PCT/IL2017/050014. (16 Pages).
International Search Report and the Written Opinion dated Dec. 31, 2019 From the International Searching Authority Re. Application No. PCT/IL2019/051163. (16 Pages).
Interview Summary dated Feb. 23, 2021 From the US Patent and Trademark Office Re. U.S. Appl. No. 16/068,373. (3 Pages).
Notice of Acceptance dated Aug. 28, 2019 From the Australian Government, IP Australia Re. Application No. 2015283589. (4 Pages).
Notice of Allowance dated Jun. 1, 2017 From the US Patent and Trademark Office Re. U.S. Appl. No. 13/997,302. (24 Pages).
Notice of Allowance dated Mar. 1, 2018 From the US Patent and Trademark Office Re. U.S. Appl. No. 15/312,647. (24 pages).

(56) References Cited

OTHER PUBLICATIONS

Notice of Allowance dated Jun. 12, 2018 From the US Patent and Trademark Office Re. U.S. Appl. No. 15/308,370. (13 pages).
Notice of Allowance dated Apr. 19, 2018 From the US Patent and Trademark Office Re. U.S. Appl. No. 15/375,098, (5 pages).
Notice of Allowance dated Sep. 20, 2017 From the US Patent and Trademark Office Re. U.S. Appl. No. 15/362,841. (33 pages).
Notice of Allowance dated Sep. 20, 2017 From the US Patent and Trademark Office Re. U.S. Appl. No. 15/386,182.(32 pages).
Notice of Allowance dated Feb. 22, 2021 From the US Patent and Trademark Office Re. U.S. Appl. No. 15/690,323. (28 Pages).
Notice of Allowance dated Apr. 23, 2018 From the US Patent and Trademark Office Re. U.S. Appl. No. 15/382,819. (17 pages).
Notice of Allowance dated Oct. 23, 2018 From the US Patent and Trademark Office Re. U.S. Appl. No. 15/391,896. (16 pages).
Notice of Reason(s) for Rejection dated Jan. 26, 2021 From the Japan Patent Office Re. Application No. 2019-231996 and Its Translation Into English.(10 Pages).
Notice of Reason(s) for Rejection dated Jan. 26, 2021 From the Japan Patent Office Re. Application No. 2020-003761 and Its Translation Into English. (7 Pages).
Notice of Reasons for Rejection dated Feb. 4, 2020 From the Japan Patent Office Re. Application No. 2016-576066 and Its Translation Into English. (6 Pages).
Notice of Reasons for Rejection dated Jan. 7, 2020 From the Japan Patent Office Re. Application No. 2016-576067 and Its Translation Into English. (10 Pages).
Notice of Reasons for Rejection dated May 7, 2019 From the Japan Patent Office Re. Application No. 2016-576067 and Its Translation Into English. (3 Pages).
Notice of Reasons for Rejection dated May 7, 2019 From the Japan Patent Office Re. Application No. 2016-576068 and Its Translation Into English. (15 Pages).
Notice of Reasons for Rejection dated May 7, 2019 From the Japan Patent Office Re. Application No. 2016-576071 and Its Translation into English. (8 Pages).
Notice of Reasons for Rejection dated Mar. 9, 2021 From the Japan Patent Office Re. Application No. 2016-576068 and Its Translation Into English. (17 Pages).
Notice of Reasons for Rejection dated May 21, 2019 From the Japan Patent Office Re. Application No. 2016-576066 and Its Translation Into English. (12 Pages).
Notification of Office Action and Search Report dated Mar. 1, 2021 From the State Intellectual Property Office of the People's Republic of China Re. Application No. 201580045151.1 and Its Translation of Office Action Into English. (8 Pages).
Notification of Office Action and Search Report dated Feb. 3, 2020 From the State Intellectual Property Office of the People's Republic of China Re. Application No. 201580045151.1. 4 Pages).
Notification of Office Action and Search Report dated Sep. 3, 2019 From the State Intellectual Property Office of the People's Republic of China Re. Application No. 201580045136.7. (9 Pages).
Notification of Office Action and Search Report dated Sep. 3, 2019 From the State Intellectual Property Office of the People's Republic of China Re. Application No. 201580045638.X. (15 Pages).
Notification of Office Action and Search Report dated Sep. 4, 2019 From the State Intellectual Property Office of the People's Republic of China Re. Application No. 201580046016.9 and Its Translation Into English. (16 Pages).
Notification of Office Action and Search Report dated Aug. 13, 2020 From the State Intellectual Property Office of the People's Republic of China Re. Application No. 201580045151.1 and Its Translation of Office Action Into English. (9 Pages).
Notification of Office Action and Search Report dated Dec. 30, 2019 From the China National Intellectual Property Administration Re. Application No. 201580045638.X. (11 Pages).
Notification of Office Action dated Aug. 1, 2019 From the State Intellectual Property Office of the People's Republic of China Re. Application No. 201580045151.1 and its Translation into English. (8 Pages).
Notification of Office Action dated Aug. 2, 2018 From the State Intellectual Property Office of the People's Republic of China Re. Application No. 201580045151.1 and Its Summary in English. (6 Pages).
Notification of Office Action dated Feb. 3, 2019 From the State Intellectual Property Office of the People's Republic of China Re. Application No. 201580045136.7 and Its Translation Into English. (4 Pages).
Notification of Office Action dated Jan. 3, 2020 From the China National Intellectual Property Administration Re. Application No. 201580046016.9 and Its Translation Into English. (13 Pages).
Notification of Office Action dated Feb. 11, 2019 From the State Intellectual Property Office of the People's Republic of China Re. Application No. 201580045638.X and Its Translation Into English. (4 Pages).
Notification of Office Action dated Feb. 11, 2019 From the State Intellectual Property Office of the People's Republic of China Re. Application No. 201580046016.9 and Its Translation Into English. (4 Pages).
Notification of Office Action dated Dec. 27, 2019 From the State Intellectual Property Office of the People's Republic of China Re. Application No. 201580045136.7 and its Translation Into English. (4 Pages).
Notification of Office Action dated Feb. 27, 2019 From the State Intellectual Property Office of the People's Republic of China Re. Application No. 201580045151.1 and Its Translation into English. (6 Pages).
Office Action dated Apr. 15, 2019 From the Israel Patent Office Re. Application No. 249834 and Its Translation Into English. (5 Pages).
Office Action dated Apr. 15, 2019 From the Israel Patent Office Re. Application No. 249835 and Its Translation Into English. (5 Pages).
Office Action dated Jan. 17, 2019 Fromthe Israel Patent Office Re. Application No. 260852 and Its Translation Into English. (6 Pages).
Office Action dated Jan. 19, 2017 From the Israel Patent Office Re. Application No. 227102 and Its Translation Into English. (5 Pages).
Office Action dated Dec. 21, 2017 From the Israel Patent Office Re. Application No. 227102 and Its Translation Into English. (4 Pages).
Office Action dated Jun. 22, 2016 From the Israel Patent Office Re. Application No. 227102 and Its Translation Into English.
Office Action dated Jan. 30, 2020 From the Israel Patent Office Re. Application No. 249836 and Its Translation Into English. (9 Pages).
Official Action dated Jun. 1, 2017 From the US Patent and Trademark Office Re. U.S. Appl. No. 15/375,098. (42 pages).
Official Action dated Nov. 1, 2017 From the US Patent and Trademark Office Re. U.S. Appl. No. 15/382,819. (45 pages).
Official Action dated Feb. 4, 2019 From the US Patent and Trademark Office Re. U.S. Appl. No. 15/362,883. (53 pages).
Official Action dated Apr. 6, 2017 From the US Patent and Trademark Office Re. U.S. Appl. No. 15/362,841. (35 pages).
Official Action dated Mar. 9, 2017 From the US Patent and Trademark Office Re. U.S. Appl. No. 15/386,182. (24 pages).
Official Action dated Sep. 1, 2020 from the US Patent and Trademark Office Re. U.S. Appl. No. 15/690,323. (14 pages).
Official Action dated Apr. 10, 2017 From the US Patent and Trademark Office Re. U.S. Appl. No. 15/362,883. (33 pages).
Official Action dated Dec. 12, 2017 From the US Patent and Trademark Office Re. U.S. Appl. No. 15/308,370. (27 pages).
Official Action dated Mar. 13, 2017 From the US Patent and Trademark Office Re. U.S. Appl. No. 15/391,896. (22 pages).
Official Action dated Mar. 14, 2018 From the US Patent and Trademark Office Re. U.S. Appl. No. 15/362,883. (21 pages).
Official Action dated Aug. 18, 2017 From the US Patent and Trademark Office Re. U.S. Appl. No. 15/308,370. (56 pages).
Official Action dated Apr. 20, 2017 From the US Patent and Trademark Office Re. U.S. Appl. No. 15/382,819. (30 pages).
Official Action dated Sep. 22, 2017 From the US Patent and Trademark Office Re. U.S. Appl. No. 15/362,883, (43 pages).
Official Action dated Jan. 25, 2018 From the US Patent and Trademark Office Re. U.S. Appl. No. 15/375,098. (37 pages).
Official Action dated Dec. 26, 2017 From the US Patent and Trademark Office Re. U.S. Appl. No. 15/391,896. (53 pages).
Official Action dated Jul. 28, 2020 from the US Patent and Trademark Office Re. U.S. Appl. No. 16/131,079. (102 pages).

(56) References Cited

OTHER PUBLICATIONS

Official Action dated Sep. 28, 2017 From the US Patent and Trademark Office Re. U.S. Appl. No. 15/312,647. (57 pages).
Official Action dated Jan. 30, 2017 From the US Patent and Trademark Office Re. U.S. Appl. No. 13/997,302. (23 pages).
Official Action dated Sep. 30, 2016 From the US Patent and Trademark Office Re. U.S. Appl. No. 13/997,302.
Official Action dated Sep. 30, 2019 From the US Patent and Trademark Office Re. U.S. Appl. No. 15/690,323, (123 pages).
Official Action dated May 31, 2018 From the US Patent and Trademark Office Re. U.S. Appl. No. 15/391,896. (17 pages).
Official Action dated Jan. 8, 2021 from the US Patent and Trademark Office Re. U.S. Appl. No. 16/068,373. (85 pages).
Patent Examination Report dated Sep. 14, 2020 From the Australian Government, IP Australia Re. Application No. 2019275594. (4 Pages).
Patent Examination Report dated Nov. 23, 2020 From the Australian Government, IP Australia Re. Application No. 2019229370. (4 Pages).
Pre-Appeal Examination Report dated Feb. 6, 2020 From the Japan Patent Office Re. Application No. 2016-576068 and Its Translation Into English.
Request for Examination and Search Report dated Feb. 4, 2021 From the Federal Government Institution, Federal Institute of Industrial Property of the Federal Service of Intellectual Property, Patents and Trademarks of the Russian Federation, FIPS Re. Application No. 2020130235 and Its Translation of Office Action Into English. (9 Pages).
Request for Examination and Search Report dated Nov. 22, 2018 From the Federal Government Institution, Federal Institute of Industrial Property of the Federal Service for Intellectual Property, Patents and Trademarks of the Russian Federation Re. Application No. 2017102236 and Its Translation of Office Action Into English. (7 Pages).
Request for Examination and Search Report dated Nov. 23, 2018 From the Federal Government Institution, Federal Institute of Industrial Property of the Federal Service for Intellectual Property, Patents and Trademarks of the Russian Federation Re. Application No. 2017102235 and Its Translation Into English. (9 Pages).
Request for Examination and Search Report dated Feb. 26, 2020 From the Federal Government Institution, Federal Institute of Industrial Property of the Federal Service of Intellectual Property, Patents and Trademarks of the Russian Federation, FIPS Re. Application No. 2019115949 and Its Translation Into English. (11 Pages).
Request for Examination and Search Report dated Nov. 27, 2018 From the Federal Government Institution, Federal Institute of Industrial Property of the Federal Service of Intellectual Property, Patents and Trademarks of the Russian Federation Re. Application No. 2017102233 and Its Translation of Office Action Into English. (8 Pages).
Request for Examination dated Feb. 4, 2021 From the (ROSPATENT), Federal Government Institution of Industrial Property of the Federal Service of Intellectual Properly, Patents and Trademark of the Russian Federation Re Application No. 2020130235. (5 Pages).
Request for Examination dated Dec. 12, 2018 From the Federal Government Institution, Federal Institute of Industrial Property of the Federal Service or Intellectual Property, Patents and Trademark of the Russian Federation Re. Application No. 2017102234 and its Translation Into English. (9 Pages).
Request for Examination dated Jan. 28, 2020 From the Federal Government Institution, Federal Institute of Industrial Property of the Federal Service or Intellectual Property, Patents and Trademark of the Russian Federation Re. Application No. 2017102234 and Its Translation Into English. (14 Pages).
Requisition by the Examiner dated Nov. 2, 2018 From the Innovation, Science and Economic Development Canada, Canadian Intellectual Property Office Re. Application No. 2,822,738. (4 Pages).
Requisition by the Examiner dated Aug. 6, 2019 From the Innovation, Science and Economic Development Canada, Canadian Intellectual Property Office Re. Application No. 2,822,738. (4 Pages).
Requisition by the Examiner dated Aug. 13, 2020 From the Innovation, Science and Economic Development Canada, Canadian Intellectual Property Office Re. Application No. 2,822,738. (3 Pages).
Requisition by the Examiner dated Nov. 16, 2017 From the Innovation, Science and Economic Development Canada, Canadian Intellectual Property Office Re. Application No. 2,822,738. (4 Pages).
Restriction Official Action dated Aug. 7, 2017 From the US Patent and Trademark Office Rc. U.S. Appl. No. 15/312,647. (8 pages).
Restriction Official Action dated Jul. 8, 2016 From the US Patent and Trademark Office Re. U.S. Appl. No. 13/997,302.
Restriction Official Action dated Sep. 17, 2020 from the US Patent and Trademark Office Re. U.S. Appl. No. 16/068,373. (8 pages).
Search Report and Explanation dated Mar. 24, 2020 From the Servico Publico Federal, Ministerio da Economia, Instituto National da Propriedade Industrial do Brasil Re. Application No. BRI 12016030944-8 and Its Summary in English. (5 Pages).
Search Report and Explanation dated Mar. 24, 2020 From the Servico Publico Federal, Ministerio da Economia, Instituto National da Propriedade Industrial do Brasil Re. Application No. BR112016030952-9 and Its Summary in English. (5 Pages).
Search Report and Explanation dated Mar. 24, 2020 From the Sevico Publico Federal, Ministerio da Economia, Instituto National da Propriedade Industrial do Brasil Re. Application No. BR112016030955-3 and Its Summary in English. (5 Pages).
Search Report and Explanations dated Apr. 15, 2020 From the Servico Publico Federal, Ministerio da Economia, Instituto National da Propriedade Industrial do Brasil Re. Application No. BR112016030829-8 and Its Summary in English. (5 Pages).
Summons to Attend Oral Proceedings Pursuant to Rule 115(1) EPC Dated Sep. 24, 2020 From the European Patent Office Re. Application No. 15814472.5. (6 Pages).
Supplementary European Search Report and the European Search Opinion Dated Aug. 19, 2019 From the European Patent Office Re. Application No. 17735927.0. (8 Pages).
Supplementary European Search Report and the European Search Opinion dated Mar. 19, 2018 From the European Patent Office Re. Application No. 15814472.5. (9 Pages).
Supplementary European Search Report and the European Search Opinion dated Mar. 19, 2018 From the European Patent Office Re. Application No. 15815982.2. (8 Pages).
Translation Dated Oct. 1, 2019 of Notification of Office Action dated Sep. 3, 2019 From the State Intellectual Property Office of the People's Republic of China Re. Application No. 201580045638.X. (13 Pages).
Translation Dated Aug. 14, 2018 of Notification of Office Action dated Aug. 2, 2018 From the State Intellectual Property Office of the People's Republic of China Re. Application No. 201580045151.1. (3 Pages).
Translation Dated Sep. 18, 2019 of Notification of Office Action dated Sep. 3, 2019 From the State Intellectual Property Office of the People's Republic of China Re. Application No. 201580045136.7. (5 Pages).
Translation Dated Feb. 20, 2020 of Notification of Office Action dated Feb. 3, 2020 From the State Intellectual Property Office of the People's Republic of China Re. Application No. 201580045. (4 Pages).
Translation Dated Jan. 22, 2020 of Notification of Office Action Dated Dec. 30, 2019 Fromthe China National Intellectual Property Administration Re. Application No. 201580045638,X, (9 Pages).
Written Opinion dated Apr. 22, 2013 From the International Preliminary Examining Authority Re. Application No. PCT/IL2011/050071.
AAAAI "Inhaled Asthma Medications: Tips to Remember", American Academy of Allergy Asthma & Immunology, AAAAI, 4 P., 2013.
Abrams et al. "Vaporization as a Smokeless Cannabis Delivery System: A Pilot Study", Clinical Pharmacology & Therapeutics, 82(5): 572-578, Advance Online Publication Apr. 11, 2007.

(56) References Cited

OTHER PUBLICATIONS

Assaf et al. "Pre- and Post-Conditioning Treatment With An Ultra-Low Dose of [Delta]/\sup9/\-Tetrahydrocannabinol (THC) Protects Against Pentylenetetrazole (PTZ)-Induced Cognitive Damage", Behavioral Brain Research, 220(1): 194-201, Jun. 2011.
Bhattacharyya et al. "Opposite Effects of Delta-9-Tetrahydrocannabinol and Cannabidiol on Human Brain Function and Psychopathology", Neuropsychophartnacology, 35: 764-774, 2010.
Boden et al. "The Effects of Cannabis Use Expectancies on Self-Initiated Cannabis Cessation", Addiction, 108: 1649-1657, 2013.
Carter et al. "Medicinal Cannabis: Rational Guidelines for Dosing". IDrugs, 7(5): 464-470, May 2004.
Cohen et al. "Modelling of the Concentration—Effect Relationship of THC on Central Nervous System Parameters and Heart Rate—Insight Into Its Mechanisms of Action and a Tool for Clinical Research and Development of Cannabinoids", Journal of Pharmacology, 22(7): 717-726, Sep. 2008.
Das et al. "Effects of 9-Ene-Tetrahydrocannabinol on Expression of Beta-Type Transforming Growth Factors, Insulin-Like Growth Factor-I and C-Myc Genes in the Mouse Utems", Tire Journal of Steroid Biochemistry and Molecular Biology, 45(6): 459-465, 1993.
Eisenberg et al. "The Pharmacokinetics, Efficacy, Safety, and Ease of Use of A Novel Portable Metered-Dose Cannabis Inhaler in Patients With Chronic Neuropathic Pain: A Phase la Study", Journal of Pain & Palliative Care Pharmacotherapy, 28(3): 216-225. Published Online Aug. 13, 2014.
Farrimond et al. "Cannabinol and Cannabidiol Exert Opposing Effects on Rat Feeding Patterns", Psychopharmacology, 223: 117-129, 2012.
FDA "Guidance for Industry. Population Pharmacokinetics", U.S. Department of Health and Human Services. Food and Drug Administration (FDA), Center for Drug Evaluation and Research (CDER), Center for Biological Evaluation and Research (CBER), CP 1: 1-31, Feb. 1999.
Fishbein et al. "Long-Term Behavioral and Biochemical Effects of an Ultra-Low Dose of [Delta]/\sup9/\-Tetrahydrocannabinol (THC): Neuroprotection and ERK Signaling", Experimental Brain Research, 221(4): 437-448, Published Online Jul. 22, 2012.
Green Machine "Structure of a leaf—Internal & External", Retrieved from google.com, 6 Pages, Sep. 2019.
Hazekamp et al. "Bedrocan® - Stimulating the Development of Herbal Cannabis-Based Products", Bedromedical Presentation, 2013.
Hazekamp et al. "Evaluation of A Vaporizing (Volcano®) for the Pulmonary Administration of Tetrahydrocannabinol", Journal of Pharmaceutical Sciences, 95(6): 1308-1317, Jun. 2006.
Hazekamp et al. "The Medicinal Use of Cannabis and Cannabinoids—An International Cross-Sectional Survey on Administration Forms", Journal of Psychoactive Drugs, 45(3): 199-210, 2013.
Herbalizcr "Herbalizer, the New Vaporization Experience", 6 P., Jun. 7, 2013.
Ibrahim et al. "Inhalation Drug Delivery Devices: Technology Update", Medical Devices: Evidence and Research, 8: 131-139, Feb. 12, 2015.
Jamontt et al. "The Effects of Delta[9]—Tetrahydrocannabinol and Cannabidiol Alone and in Combination on Damage, Inflammation and In Vitro Motility Disturbances in Rat Colitis", British Journal of Pharmacology, 160: 712-723, 2010.
Jang et al. "Thermophysical Properties of Porous SiC Ceramics Fabricated by Pressureless Sintering", Science and Technology of Advanced Materials, 8(7): 655-659, Nov. 30, 2007.
Lanz et al. "Medicinal Cannabis: In Vitro Validation of Vaporizers for the Smoke-Free Inhalation of Cannabis", PLOS ONE, 11(1): e0147286-1-e0147286-18, Jan. 19, 2016.
McPartland et al. "Affinity and Efficacy Studies of Tetrahydrocannabinolic Acid A at Cannabinoid Receptor Types One and Two", Cannabis and Cannabinoid Research, 2(1): 87-95, May 2017.
McPartland et al. "Are Cannabidiol and Delta9-Tetrahydrocannabivarin Negative Modulators of the Endocannabinoid System? A Systematic Review", British Journal of Pharmacology, 172(3): 737-753, Published Online Jan. 8, 2015.
McPartland et al. "Cannabis and Cannabis Extracts: Greater Than the Sum of Their Parts?", Journal of Cannabis Therapeutics, 1(3-4):103-132, Jun. 1, 2001.
Mechoulam et al. "Cannabidiol—Recent Advances", Chemistry & Biodiversity, 4: 1678-1692, 2007.
Moreno-Sanz "Can You Pass the Acid Test? Critical Review and Novel Therapeutic Perspectives of Delta9-Tetrahydrocannabinolic Acid A", Cannabis and Cannabinoid Research, 1(1): 124-130, Published Online Jun. 1, 2016.
Norwood et al. "Best Practices for Extractables and Leachables in Orally Inhaled and Nasal Drag Products: An Overview of the PQRI Recommendations", Pharmaceutical Research, 25(4): 727-739, Published Online Jan. 9, 2008.
Ormrod et al. "A Survey of Weed Leaf Stomata and Trichomes", Canadian Journal of Plant Science, 48(2): 197-209, 1968.
Pertwee "The Diverse CB 1 and CB2 Receptor Pharmacology of Three Plant Cannabinoids: Delta[9]-Tetrahydrocannabinol, Cannabidiol andDelta[9]-Tetrahydrocannabivarin", British Journal of Pharmacology, 153: 199-215, 2008.
Pomahacova et al. "Cannabis Smoke Condensate III: The Cannabinoid Content of Vaporised Cannabis Sativa", Inhalation Toxicology, 21(13): 1108-1112, Nov. 1, 2009.
Rabinowitz et al. "Fast Onset Medications Through Thermally Generated Aerosols", The Journal of Pharmacological and Experimental Therapeutics, 309(2): 769-775, Published Online Jan. 29, 2004.
Rau "The Inhalation of Drags: Advantages and Problems", Respiratory Care, 50(3): 367-382, Mar. 2005.
Science "Nettle leaf trichromes", Retrieved fromsciencesource.com, 1 Page, Sep. 2019.
Syqe Medical "The World's First Metered Dose Pharmaceutical Grade Medical Cannabis Inhaler", Syqe Medical™, Press Kit, p. 1-8, 2015.
Van Gerven "Biomarkers to Assess Adverse Drug Effects on the CNS", Centre for Human Drug Research, CHDR, Poster-Session, Slide-Show, 25 P., 2013.
Van Hell et al. "Evidence for Involvement of the Insula in the Psychotropic Effects of THC in Humans: A Double-Blind, Randomized Pharamcological MRI Study". International Journal of Neuropharmacology, 14: 1377-1388, 2011.
Vann et al. "Divergent Effects of Cannabidiol on the Discriminative Stimulus and Place Conditioning Effects of Delta 9-Tetrahydrocannabiol", Drug and Alcohol Dependence, 94(1-3): 191-198, Apr. 1, 2008.
Vemuri et al. "Pharmacotherapeutic Targeting of the Endocannabinoid Signaling System: Drags for Obesity and the Metabolic Syndrome", Physiology & Behavior, 93:671-686, 2008.
Wallace et al. "Efficacy of Inhaled Caimabis on Painful Diabetic Neuropathy", Tlie Journal of Pain, 169(7): 616-627, Published Online Apr. 3, 2015.
Ware et al. "Smoked Cannabis for Chronic Neuropathic Pain: A Randomized Controlled Trial", Canadian Medical Association Journal, CMAJ, 182(14): E694-E701, Published Online Aug. 30, 2010.
Wilsey et al. "A Randomized, Placebo-Controlled. Crossover Trial of Caimabis Cigarettes in Neuropathic Pain", The Journal of Pain, 9(6): 506-521, Published Online Apr. 10, 2008.
Wilsey et al. "Low-Dose Vaporized Cannabis Significantly Improves Neuropathic Pain", The Journal of Pain, 14(2): 136-148. Published Online Dec. 13, 2012. 'Discussion', Last Para.
Zuurman et al. "Biomarkers for the Effects of Cannabis and THC in Healthy Volunteers", British Journal of Clinical Pharmacology, 67(1): 5-21, 2008.
Zuurman et al. "Effect of Intrapulmonary Tetrahydrocannabinol Administration in Humans", Journal of Psychopharmacology, 22(7): 707-716, 2008.
Patent Examination Report dated Aug. 13, 2021 From the Australian Government, IP Australia Re. Application No. 2020205271. (7 Pages).
Requisition by the Examiner Dated Aug. 19, 2021 From the Innovation, Science and Economic Development Canada, Canadian Intellectual Property Office Re. Application No. 2,953,074. (16 Pages).

(56) References Cited

OTHER PUBLICATIONS

Requisition by the Examiner Dated Aug. 26, 2021 From the Innovation, Science and Economic Development Canada, Canadian Intellectual Property Office Re. Application No. 2,953,082. (28 Pages)
Supplementary European Search Report and the European Search Opinion dated Dec. 16, 20021 From the European Patent Office Re. Application No. 19754583.3. (6 Pages).
English Translation Dated Feb. 21, 2022 of Notification of Office Action and Search Report Dated Jan. 20, 2022 From the State Intellectual Property Office of the People's Republic of China Re. Application No. 202011200160.2.1 Pages).
European Search Report and the European Search Opinion dated Nov. 9, 2021 From the European Patent Office Re. Application No. 21199976.8. (8 Pages).
Notice of Allowance dated Dec. 20, 2021 from US Patent and Trademark Office Re. U.S. Appl. No. 16/055,269. (158 pages).
Van Oort.
Supplementary European Search Report and the European Search Opinion dated Jul. 12, 2022 From the European Patent Office Re. Application No. 19880500.4. (11 Pages).
Interview Summary dated Sep. 12, 2022 From the US Patent and Trademark Office Re. U.S. Appl. No. 16/068,373. (2 Pages).
Notice of Reasons for Rejection dated Aug. 30, 2022 From the Japan Patent Office Re. Application No. 2021-175408 and Its Translation Into Enghsh. (12 Pages).
Examination Report dated Jan. 29, 2022 from the Australian Patent Office Re. Application No. 2021202185. (5 pages).
Examination Report dated May 29, 2022 From the Servico Publico Federal, Ministerio da Economia, Institute Nacional da Propriedade Industrial do Brasil RE Application No. BR12 2020 018207 5 with Pending Claims and its English Summary. (8 Pages).
Grounds of Reason of Rejection dated Mar. 24, 2022 From the Korean Intellectual Property Office Re. Application No. 10-2017-7002682 and Its Translation Into English. (14 Pages).
Notice of Reasons for Rejection dated Mar. 22, 2022 From the Japan Patent Office Re. Application No. 2020-101083 and Its Translation Into English. (7 Pages).
Patent Examination Report dated Mar. 18, 2022 From the Australian Government, IP Australia Re. Application No. 2021204703 with claims. (7 Pages).
Patent Examination Report dated Mar. 22, 2022 From the Australian Government, IP Australia Re. Application No. 2020205271 with amended Claims. (8 Pages).
Requisition by the Examiner dated Mar. 29, 2022 From the Innovation, Science and Economic Development Canada, Canadian Intellectual Property' Office Re. Application No. 2,953.069 with Claims. (15 Pages).
Requisition by the Examiner dated Mar. 30, 2022 From the Innovation, Science and Economic Development Canada, Canadian Intellectual Property Office Re. Application No. 2,953.073 with Claims. (18 Pages).
Notification of Office Action and Search Report dated Jun. 27, 2022 From the State Intellectual Property Office of the People's Republic of China Re. Application No. 201980081175.0. (13 Pages).
Official Action dated Jul. 6, 2022 from US Patent and Trademark Office Re. U.S. Appl. No. 16/068,373. (40 pages).
Perry et al.
Final Official Action dated Jul. 6, 2021 from the US Patent and Trademark Office Re. U.S. Appl. No. 16/068,373. (33 pages).
Requisition by the Examiner dated Mar. 11, 2022 From the Innovation, Science and Economic Development Canada, Canadian Intellectual Property Office Re. Application No. 2,953,082. (6 Pages).
Bandi et al "From Detection of Individual Metastases to Classification of Lymph Node Status at the Patient Level: The CAMELYON17 Challenge", IEEE Transactions on Medical Imaging,38(2):550-560, Aug. 27, 2018.
Bauer et al. "Tools and Techniques to Standardize Tissue Collection, Transport, and Fixation", Current Pathobiology Reports, 6(2): 135-143, Apr. 25, 2018.
Colley et al. "Fixation and Other Pre-Analytical Factors", Dako:10P. ,Apr. 17, 2017.
Lanng et al. "Quality Assessment of Ki67 Staining Using Cell Line Proliferation Index and Stain Intensity Features", Cytometry, Journal of Quantitative Cell Science, 95(4):381-388, Dec. 17, 2018.
Official Action dated Aug. 5, 2021 from the US Patent and Trademark Office Re. U.S. Appl. No. 16/030,967. (163 pages).
International Preliminary Report on Patentability dated May 6, 2021 From the International Bureau of WIPO Re. Application No. PCT/IL2019/051163. (6 Pages).
Notice of Reason(s) for Rejection dated Jun. 1, 2021 From the Japan Patent Office Re. Application No. 2020-1101083 and Its Translation Into English. (12 Pages).
European Search Report and the European Search Opinion dated Oct. 11, 2021 From the European Patent Office Re. Application No. 211943 94.9 (8 Pages).
Notification of Office Action and Search Report dated Nov. 3, 2021 From the State Intellectual Property Office of the People's Republic of China Re. Application No. 202010701980.3. (10 Pages).
Office Action dated Nov. 2, 2021 From the Israel Patent Office Re. Application No. 262376 and Its Translation Into English. (7 Pages).
Ground(s) of Reason of Rejection dated Jan. 21, 2022 From the Korean Intellectual Property Office Re. Application No. 10-2017-70023243 and its Translation into English. (13 Pages).
Notification of Office Action and Search Report dated Jan. 20, 2022From the State Intellectual Property Office of the People's Republic of China Re. Application No. 202011200160.2. (6 Pages).
European Search Report and the European Search Opinion dated Dec. 17, 2021 From the European Patent Office Re. Application No. 21196651.0. (7 Pages).
Notice of Reasons for Rejection dated Feb. 22, 2022 From the Korean Intellectual Property Office Re. Application No. 10-2017-7002721 and Its Translation Into English. (5 Pages).
English Summary dated Jul. 20, 2022 of Notification of Office Action and Search Report dated Jun. 27, 2022 From the State Intellectual Property Office of the People's Republic of China Re. Application No. 201980081175.0. (1 Page).
Almog et al. "The Pharmacokinetics, Efficacy, and Safety of A Novel Selective-Dose Cannabis Inhaler in Patients With Chronic Pain: A Randomized, Double-Blineed, Placebo-Controlled Trial", European Journal of Pain, 24(8): 1505-1516, Published Online Jun. 12, 2020.
Examination Report dated Aug. 6, 2021 From the Institute Mexicano de la Propiedad Industrial, Direccion Divisional de Patentes Re. Application No. MX/a/2017/000057 and Its Translation Into English. (10 Pages).
Requisition by the Examiner dated Sep. 28, 2021 From the Innovation, Science and Economic Development Canada, Canadian Intellectual Property Office Re. Application No. 2,953,073. (4 Pages).
Interview Summary dated Dec. 24, 2021 From the US Patent and Trademark Office Re. U.S. Appl. No. 16/068,373. (3 Pages).
Notice of Reason(s) for Rejection dated Oct. 12, 2021 From the Japan Patent Office Re. Application No. 2020-101083 and Its Translation Into English. (17 Pages).
Notice of Reason(s) for Rejection dated Oct. 12, 2021 From the Japan Patent Office Re. Application No. 2020-134166 and Its Translation Into English. (10 Pages).
Request for Examination and Search Report dated Mar. 10, 2023 From the (ROSPATENT), Federal Government Institution of Industrial Property of the Federal Service of Intellectual Property, Patents and Trademark of the Russian Federation Re. Application No. 2021125574. (9 Pages).
Request for Examination and Search Report dated Feb. 16, 2023 From the (ROSPATENT), Federal Government Institution of Industrial Property of the Federal Service of Intellectual Property, Patents and Trademark of the Russian Federation Re. Application No. 202111628 and its Summary in English.(12 Pages).

(56) References Cited

OTHER PUBLICATIONS

Notification of Office Action and Search Report dated Oct. 25, 2022 From the State Intellectual Property Office of the People's Republic of China Re. Application No. 202110926270.5 and Its Translation of Office Action Into English. (7 Pages).
Supplementary European Search Report and the European Search Opinion dated Nov. 14, 2022 From the European Patent Office Re. Application No. 20751958.8 (8 pages).
Communication Pursuant to Article 94(3) EPC dated Feb. 6, 2023 From the European Patent Office Re. Application No. 20150198.8 (7 Pages).
Translation Dated Apr. 10, 2023 of Request for Examination and Search Report dated Mar. 10, 2023 From the (ROSPATENT), Federal Government Institution of Industrial Property of the Federal Service of Intellectual Property, Patents and Trademark of the Russian Federation Re. Application No. 2021125574. (5 Pages).
Examination Report dated Jan. 11, 2023 From the Australian Government. IP Australia Re. Application No. 2021204365. (4 Pages).
Requisition by the Examiner Dated Dec. 22, 2022 From the Innovation, Science and Economic Development Canada. Canadian Intellectual Property Office Re. Application No. 3,009,599.(10 pages).
Official Action dated Mar. 30, 2023 From the US Patent and Trademark Office Re. U.S. Appl. No. 17/679,190. (287 Pages).
Translation Dated Mar. 30, 2023 of Request for Examination and Search Report dated Feb. 16, 2023 From the (ROSPATENT). Federal Government Institution of Industrial Property of the Federal Service of Intellectual Property , Patents and Trademark of the Russian Federation Re. Application No. 202111628 and its Summary in English.(7 Pages).
Ground(s) of Reason of Rejection dated Nov. 21, 2022 From the Korean Intellectual Property Office Re. Application No. 10-2022-7038127 and its Translation into English. (5 Pages).
Requisition by the Examiner dated Nov. 28, 2022 From the Innovation, Science and Economic Development Canada, Canadian Intellectual Property Office Re. Application No. 2,953,069 with Claims. (17 Pages).
Requisition by the Examiner dated Nov. 28, 2022 From the Innovation, Science and Economic Development Canada. Canadian Intellectual Property Office Re. Application No. 2,953,073. (3 Pages).
Notice of Reason(s) for Rejection dated Mar. 7, 2023 From the Japan Patent Office Re. Application No. 2021-175408 and Its Translation Into English. (5 Pages).
Requisition by the Examiner Dated Dec. 13, 2022 From the Innovation, Science and Economic Development Canada. Canadian Intellectual Property Office Re. Application No. 2,953,074 with claims. (11 pages).
Decision on Rejection Dated Apr. 23, 2023 From the State Intellectual Property Office of the People's Republic of China Re. Application No. 201980081175.0. (8 pages).
English Summary dated Apr. 26, 2023 of Notification of Office Action dated Apr. 19, 2023 From the State Intellectual Property Office of the People's Republic of China Re. Application No. 202080027182.5. (2 pages).
Notification of Office Action and Search Report dated Apr. 13, 2023 From the State Intellectual Property Office of the People's Republic of China Re. Application No. 202080027182.5 (11 pages).
English Summary dated May 4, 2023 of Decision on Rejection Dated Apr. 23, 2023 From the State Intellectual Property Office of the People's Republic of China Re. Application No. 201980081175.0 (1 page).
Grounds of Reason of Rejection dated Apr. 20, 2023 From the Korean Intellectual Property Office Re. Application No. 10-2022-7045372 and Its Translation Into English. (9 Pages).
Grounds of Reason of Rejection dated May 22, 2023 From the Korean Intellectual Property Office Re. Application No. 10-2022-7036865 and Its Translation Into English. (6 Pages).
Notice of Allowance dated Jun. 28, 2023 Together with Interview Summary dated Jun. 13, 2023 from the U.S. Patent and Trademark Office Re. U.S. Appl. No. 16/068,373. (39 pages).
Notice of Reason(s) for Rejection dated Jun. 13, 2023 From the Japan Patent Office Re. Application No. 2022-115378. (4 pages).
Notice of Reason(s) for Rejection dated May 16, 2023 From the Japan Patent Office Re. Application No. 2021-522537 and Its Translation Into English. (9 Pages).
Requisition by the Examiner Dated Jul. 5, 2023 From the Innovation, Science and Economic Development Canada, Canadian Intellectual Property Office Re. Application No. 2,953,073. (3 pages).
Requisition by the Examiner Dated Jun. 27, 2023 From the Innovation, Science and Economic Development Canada, Canadian Intellectual Property Office Re. Application No. 3,114,582. (3 pages).
Translation Dated Jun. 23, 2023 of Notice of Reason(s) for Rejection Dated Jun. 13, 2023 From the Japan Patent Office Re. Application No. 2022-115378. (4 pages).
Translation for the Rejection of Claim 1 Dated May 11, 2023 of Notification of Office Action Dated Apr. 13, 2023 From the State Intellectual Property Office of the People's Republic of China Re. Application No. 202080027182.5. (1 Page).

\* cited by examiner

Dose Profile
Age: Adult  Gender: Male
Indication: Cancer

| Start Time (24h) | Inhalation 1 (mg) | (sec) | Pause (sec) | Inhalation 2 (mg) | (sec) | Pause (sec) | Inhalation 3 (mg) | (sec) | Pause (sec) | Inhalation 4 (mg) | (sec) | Pause (sec) | Inhalation... (mg) | (sec) | end Time (24h) | Total (mg) | (sec) net | (sec) gross |
|---|---|---|---|---|---|---|---|---|---|---|---|---|---|---|---|---|---|---|
| 8:00:00 | 10 | 5 | 10 | 10 | 5 | 8 | 8 | 4 | 0 | 0 | 0 | 0 | 0 | 0 | 8:00:32 | 28 | 14 | 32 |
| 14:00:00 | 8 | 4 | 10 | 6 | 3 | 5 | 8 | 4 | 8 | 6 | 3 | 0 | 0 | 0 | 14:00:37 | 28 | 14 | 37 |
| 20:30:00 | 12 | 6 | 9 | 6 | 3 | 6 | 10 | 5 | 0 | 0 | 0 | 0 | 0 | 0 | 20:30:29 | 28 | 14 | 29 |

*THC as reference active compound in mg

Dose Profile
Age: Child  Gender: Female
Indication: Tourette

| Start Time (24h) | Inhalation 1 (mg) | (sec) | Pause (sec) | Inhalation 2 (mg) | (sec) | Pause (sec) | Inhalation 3 (mg) | (sec) | Pause (sec) | Inhalation 4 (mg) | (sec) | Pause (sec) | Inhalation... (mg) | (sec) | end Time (24h) | Total (mg) | (sec) net | (sec) gross |
|---|---|---|---|---|---|---|---|---|---|---|---|---|---|---|---|---|---|---|
| 8:00:00 | 2 | 1 | 6 | 4 | 2 | 8 | 2 | 1 | 5 | 2 | 1 | 0 | 0 | 0 | 8:00:32 | 10 | 5 | 24 |
| 11:00:00 | 4 | 2 | 4 | 4 | 2 | 5 | 2 | 1 | 0 | 0 | 0 | 0 | 0 | 0 | 14:00:37 | 10 | 5 | 14 |
| 14:00:00 | 6 | 3 | 15 | 2 | 1 | 5 | 2 | 1 | 0 | 0 | 0 | 0 | 0 | 0 | 14:00:37 | 10 | 5 | 25 |
| 17:00:00 | 2 | 1 | 10 | 4 | 2 | 10 | 2 | 1 | 5 | 2 | 1 | 0 | 0 | 0 | 14:00:37 | 10 | 5 | 30 |
| 20:00:00 | 2 | 1 | 8 | 2 | 1 | 15 | 4 | 2 | 10 | 2 | 1 | 0 | 0 | 0 | 8:00:29 | 10 | 5 | 38 |

*THC as reference active compound in mg

Dose Profile
Age: Adult  Gender: Male
Indication: Chronic Pain

| Start Time (24h) | Inhalation 1 (mg) | (sec) | Pause (sec) | Inhalation 2 (mg) | (sec) | Pause (sec) | Inhalation 3 (mg) | (sec) | Pause (sec) | Inhalation 4 (mg) | (sec) | Pause (sec) | Inhalation... (mg) | (sec) | end Time (24h) | Total (mg) | (sec) net | (sec) gross |
|---|---|---|---|---|---|---|---|---|---|---|---|---|---|---|---|---|---|---|
| 8:00:00 | 14 | 7 | 3 | 12 | 6 | 2 | 12 | 6 | 0 | 0 | 0 | 0 | 0 | 0 | 8:00:32 | 38 | 19 | 24 |
| 14:00:00 | 8 | 4 | 10 | 8 | 4 | 0 | 0 | 0 | 0 | 0 | 0 | 0 | 0 | 0 | 14:00:37 | 16 | 8 | 18 |
| 21:00:00 | 14 | 7 | 2 | 12 | 6 | 6 | 10 | 5 | 10 | 8 | 4 | 0 | 0 | 0 | 8:00:29 | 44 | 22 | 40 |

*THC as reference active compound in mg

FIG. 14

| # | Administration Data | | | | | Subjective Data Entry | | | Clinical Data Entry | | |
|---|---|---|---|---|---|---|---|---|---|---|---|
| | Timestamp | | Dose | | Source Material | | | | | | |
| | Date | Time (24h) | Quantity (mg) | Duration (sec) | ID | Query 1 | Query 2 | Query... | Dataset 1 | Dataset 2 | Dataset... |
| 1 | 10-10-12 | 8:00 | 28 | 32 | 54321 | 4 | 5 | 3 | 5.2 | 3.3 | 4.1 |
| 2 | 10-10-12 | 14:05 | 28 | 37 | 54321 | 5 | 5 | 6 | | | |
| 3 | 10-10-12 | 20:30 | 28 | 29 | 54321 | 5 | 5 | 5 | | | |
| 4 | 11-10-12 | 8:20 | 28 | 30 | 54321 | 6 | 5 | 6 | | | |
| 5 | 11-10-12 | 15:10 | 28 | 32 | 54321 | 7 | 5 | 6 | | | |
| 6 | 11-10-12 | 21:05 | 28 | 35 | 54321 | 7 | 6 | 5 | | | |
| 7 | 12-10-12 | 9:00 | 28 | 29 | 54321 | 7 | 6 | 6 | | | |
| 8 | 12-10-12 | 15:00 | 28 | 29 | 54321 | 7 | 6 | 7 | | | |
| 9 | 12-10-12 | 21:25 | 28 | 31 | 54321 | 8 | 6 | 7 | | | |
| 10 | 13-10-12 | 8:45 | 22 | 32 | 54321 | 8 | 6 | 6 | 5.5 | 4.2 | 4.5 |
| 11 | 13-10-12 | 14:05 | 22 | 33 | 54321 | 7 | 5 | 7 | | | |
| 12 | 13-10-12 | 20:10 | 22 | 28 | 54321 | 8 | 6 | 6 | | | |
| 13 | 14-10-12 | 8:10 | 22 | 34 | 54321 | 7 | 6 | 7 | | | |
| 14 | 14-10-12 | 14:10 | 22 | 29 | 54321 | 7 | 7 | 7 | | | |
| 15 | 14-10-12 | 20:15 | 22 | 30 | 54321 | 8 | 7 | 6 | | | |
| 16 | 14-10-12 | 22:50 | 22 | 33 | 54321 | 7 | 7 | 6 | | | |
| 17 | 15-10-12 | 8:20 | 22 | 32 | 54321 | 7 | 7 | 5 | | | |
| 18 | 15-10-12 | 15:10 | 18 | 29 | 74200 | 9 | 7 | 7 | | | |
| 19 | 15-10-12 | 21:05 | 18 | 31 | 74200 | 9 | 7 | 7 | | | |
| 20 | 16-10-12 | 9:00 | 18 | 28 | 74200 | 8 | 7 | 7 | | | |
| 21 | 16-10-12 | 15:00 | 18 | 34 | 74200 | 9 | 7 | 7 | 6.4 | 5.8 | 5.2 |
| 22 | 16-10-12 | 21:25 | 18 | 33 | 74200 | 9 | 7 | 7 | | | |
| 23 | 17-10-12 | 8:00 | 18 | 32 | 74200 | 8 | 7 | 7 | | | |
| 24 | 17-10-12 | 14:05 | 18 | 31 | 74200 | 9 | 8 | 7 | | | |
| 25 | 17-10-12 | 20:30 | 18 | 30 | 74200 | 9 | 7 | 7 | | | |

FIG. 15A

Patient Medical Information

| Date | Indication | Medical History | Current Medication |
|---|---|---|---|
| 10-10-12 | Cancer | Condition 1, Condition 2, Condition... | drug 1, drug 2, drug... |
| 20-10-12 | Cancer | Condition 1, Condition 2, Condition... | drug 1, drug 2, drug... |

Prescription Information

| Date | Physician ID | Time | mg | Profile Product ID | Prescription Lock |
|---|---|---|---|---|---|
| 09-10-12 | 4575 | 8:00 | 10 | 54 | Unlocked |
| | | 14:00 | 10 | | |
| | | 20:00 | 10 | | |
| 15-10-12 | 4575 | 8:00 | 8 | 74 | Locked |
| | | 14:00 | 8 | | |
| | | 20:00 | 8 | | |

Patient Personal Information

| ID | Title | First Name | Middle | Last | Date of Birth | Telephone | Address |
|---|---|---|---|---|---|---|---|
| 12345 | Mr. | John | Mobius | Smith | 14-12-60 | 555-24574 | Townville 0391 |

Physician Information

| ID | Title | First Name | Middle | Last | Specialization | Telephone | Address |
|---|---|---|---|---|---|---|---|
| 4575 | Dr. | Erwin | Good | Man | Oncology | 555-54657 | Townville 0348 |

FIG. 15B

| Source Material Information | | | | | | | | | | | | | |
|---|---|---|---|---|---|---|---|---|---|---|---|---|---|
| | | | | Cannabinoids | | Terpenoids | | | Flavonoids | | | Other Parameters | |
| Product ID | Issued ID | Date produced | Manufacturer ID | Expiry Date | Cannabinoid 1 | Cannabinoid 2 | Cannabinoid... | Terpenoid 1 | Terpenoid 2 | Terpenoid... | Flavonoid 1 | Flavonoid 2 | Flavonoid... | Parameter... |
| 54 | 54319 | 20-09-12 | 12 | 20-09-13 | 21.05% | 4.50% | 0.05% | 0.07% | 0.10% | 0.03% | 0.06% | 0.03% | 0.08% | 2.00% |
| | 54320 | 20-09-12 | 12 | 20-09-13 | 21.05% | 4.50% | 0.05% | 0.07% | 0.10% | 0.03% | 0.06% | 0.03% | 0.08% | 2.00% |
| | 54321 | 20-09-12 | 12 | 20-09-13 | 21.05% | 4.50% | 0.05% | 0.07% | 0.10% | 0.03% | 0.06% | 0.03% | 0.08% | 2.00% |
| | 54322 | 20-09-12 | 12 | 20-09-13 | 21.70% | 4.55% | 0.04% | 0.07% | 0.11% | 0.03% | 0.06% | 0.04% | 0.10% | 2.05% |
| | 54323 | 20-09-12 | 12 | 20-09-13 | 21.70% | 4.55% | 0.04% | 0.07% | 0.11% | 0.03% | 0.06% | 0.04% | 0.10% | 2.05% |
| | 54324 | 20-09-12 | 12 | 20-09-13 | 21.70% | 4.55% | 0.04% | 0.07% | 0.11% | 0.03% | 0.06% | 0.04% | 0.10% | 2.05% |
| | 54325 | 20-09-12 | 12 | 20-09-13 | 21.70% | 4.55% | 0.04% | 0.07% | 0.11% | 0.03% | 0.06% | 0.04% | 0.10% | 2.05% |
| 74 | 74190 | 10-08-12 | 15 | 10-08-13 | 6.20% | 5.70% | 0.10% | 0.03% | 0.05% | 0.03% | 0.03% | 0.07% | 0.10% | 0.03% |
| | 74191 | 10-08-12 | 15 | 10-08-13 | 6.20% | 5.70% | 0.10% | 0.03% | 0.05% | 0.03% | 0.03% | 0.07% | 0.10% | 0.03% |
| | 74192 | 10-08-12 | 15 | 10-08-13 | 6.20% | 5.70% | 0.10% | 0.03% | 0.05% | 0.03% | 0.03% | 0.07% | 0.10% | 0.03% |
| | 74193 | 10-08-12 | 15 | 10-08-13 | 6.21% | 5.70% | 0.11% | 0.03% | 0.04% | 0.04% | 0.03% | 0.07% | 0.11% | 0.03% |
| | 74194 | 10-08-12 | 15 | 10-08-13 | 6.21% | 5.70% | 0.11% | 0.03% | 0.04% | 0.04% | 0.03% | 0.07% | 0.11% | 0.03% |
| | 74195 | 10-08-12 | 15 | 10-08-13 | 6.21% | 5.70% | 0.11% | 0.03% | 0.04% | 0.04% | 0.03% | 0.07% | 0.11% | 0.03% |
| | 74196 | 10-08-12 | 15 | 10-08-13 | 6.21% | 5.70% | 0.11% | 0.03% | 0.04% | 0.04% | 0.03% | 0.07% | 0.11% | 0.03% |

FIG. 15C

METHOD AND SYSTEM FOR DRUG DELIVERY

RELATED APPLICATIONS

This application is a continuation of U.S. patent application Ser. No. 15/690,323 filed on Aug. 30, 2017, which is a continuation of U.S. patent application Ser. No. 13/997,302 filed on Jun. 24, 2013, now U.S. Pat. No. 9,775,379, which is a National Phase of PCT Patent Application No. PCT/IL2011/050071 having International Filing Date of Dec. 22, 2011, which claims the benefit of priority under 35 USC § 119(e) of U.S. Provisional Patent Application No. 61/425,962 filed on Dec. 22, 2010. The contents of the above applications are all incorporated by reference as if fully set forth herein in their entirety.

FIELD AND BACKGROUND OF THE INVENTION

The present invention, in some embodiments thereof, relates to a drug delivery device and method, and more particularly, but not exclusively, to a device and method for delivery of a substance extracted by local heating of plant matter.

U.S. Patent Publication No. 2005/0268911 discloses "Devices and methods of entraining a substance within an airflow are disclosed."

U.S. Patent Publication No. 2011/0192399 discloses "In one embodiment, a vaporizer for vaporizing a substance is described herein."

U.S. Patent Publication No. 2010/0012118 discloses "A dosage pad that has already been pre-dosed by the manufacturer ensures that the proper amount of medication is used."

Additional background art includes:

Cannabis smoke condensate III, May 2009 B. Pomahacova, F. Van der Kooy, and R. Verpoorte. Leiden, Netherlands.

U.S. Pat. No. 7,819,116.

SUMMARY OF THE INVENTION

An aspect of some embodiments of the invention relates to plant matter organized as a tape, and a mechanism for moving the tape and/or controlling heating of the tape to extract selected doses of a substance from the plant matter. Optionally, the plant matter comprises a restricted substance. In an exemplary embodiment of the invention, the delivery of the substance is monitored and/or controlled.

There is provided in accordance with an exemplary embodiment of the invention, a device for controlled extraction of at least one active substance from at least one type of plant matter by application of heat, the device comprising:

a heating element adapted to apply heat to an area of the plant matter to extract the substance; and a mechanism adapted for moving the plant matter relative to the heating element.

In an exemplary embodiment of the invention, the device further comprises plant matter organized as a tape, the plant matter comprising the active substance. Optionally, the active substance is a restricted substance. Optionally or additionally, the active substance is selected from the group comprising: tetrahydrocannabinol, salvinorin A, benzoylmethylecgonine, dimethyltryptamine, psilocybin. Optionally or additionally, the plant matter is organized with a predetermined amount of the active substance per unit area of the tape. Optionally or additionally, a thickness of the tape ranges from about 0.2 mm to about 1.0 mm. Optionally or additionally, the tape comprises about 5 grams to about 100 grams of the plant matter. Optionally or additionally, the tape comprises a sufficient amount of the active substance for at least two treatment doses. Optionally or additionally, the tape is organized as a roll. Optionally or additionally, the tape comprises a first material layer coupled to the plant matter at a side opposite that contacting the heating element, the first layer comprising apertures large enough to let gas escape but small enough to contain residue of the heated plant matter. Optionally or additionally, a diameter of the apertures ranges from 25 μm~500 μm. Optionally or additionally, the tape comprises a second material layer coupled to the plant matter at least at a side contacting the heating element, the second layer adapted to transmit heat to the plant matter without substantially distributing the heat across the second layer.

In an exemplary embodiment of the invention, an area of the heating element ranges from about 10 mm$^2$ to about 100 mm$^2$.

In an exemplary embodiment of the invention, the device further comprises an inhaler unit adapted to connect and disconnect from the device, the inhaler unit comprising:

a mouthpiece for inhalation of the substance, the mouthpiece forming fluid communication with a vapor chamber upon the connection of the inhaler unit and the device, the vapor chamber comprising the extracted active substance.

Optionally, the mouthpiece comprises a one way valve to control fluid flow away from the vapor chamber. Optionally or additionally, the device further comprising a sensor in fluid communication with the mouthpiece, the sensor adapted to estimate an air flow rate and send a signal to a controller, the controller adapted for extracting the substance according to the airflow rate.

In an exemplary embodiment of the invention, the device further comprises a controller configured to synchronize the application of heat and the movement of the plant matter.

In an exemplary embodiment of the invention, the device further comprises circuitry for controlling activation of the heating element.

In an exemplary embodiment of the invention, the device further comprises a communication interface for communicating to one or more external computers.

In an exemplary embodiment of the invention, the device further comprises a dose display meter for providing visual output of the extraction of the substance.

In an exemplary embodiment of the invention, the device is portable and weights no more than 300 grams.

In an exemplary embodiment of the invention, the device further comprises a memory adapted to hold at least one of prescription data and usage data, the memory coupled to the controller, the controller adapted to control at least one of the heating element and the mechanism according to the prescription data.

In an exemplary embodiment of the invention, the device further comprises a storage chamber adapted to store vaporized tape after the application of the heat.

In an exemplary embodiment of the invention, the device further comprises a unique ID adapted for tracking the device use by an associated patient.

In an exemplary embodiment of the invention, the device further comprises a sensor adapted to detect a physical breach of the device.

There is provided in accordance with an exemplary embodiment of the invention, a method for controlled extraction of an active substance from matter, the matter organized as a tape, the method comprising;

applying heat to an area of the tape to extract a predetermined amount of the active substance; and moving the tape relative to a heat source.

In an exemplary embodiment of the invention, the method further comprises adjusting at least one of timing and speed of the moving to extract the active substance according to a delivery profile. Optionally, the matter comprises plant matter having a macroscopic plant structure.

In an exemplary embodiment of the invention, the method further comprises treating a patient by inhaling the extracted active substance.

In an exemplary embodiment of the invention, the tape is moved relative to the heat source at a rate of about 0.1 mm/second to about 1 mm/second. Optionally or alternatively or additionally, the tape is moved in steps relative to the heat source.

In an exemplary embodiment of the invention, the extracting comprises extracting during inhalation.

In an exemplary embodiment of the invention, the applying heat comprises applying heat to reach a target temperature in less than 500 milliseconds after a start signal.

In an exemplary embodiment of the invention, the delivery profile comprises of at least one dose. Optionally, the method further comprises logging details of delivery of the at least one dose. Optionally or additionally, the method further comprises delivering a dose during specified windows of time during a day.

In an exemplary embodiment of the invention, the method further comprises titrating a dose up or down.

There is provided in accordance with an exemplary embodiment of the invention, a method for controlled extraction of at least one active substance from at least one type of plant matter by application of heat, the method comprising:

heating up multiple areas of plant matter organized as one or more tapes with one user trigger, to release the at least one active substance. Optionally, the areas comprise different active substances.

There is provided in accordance with an exemplary embodiment of the invention, a method of monitoring and controlling inhalation of a restricted substance released by localized heating of a tape comprising plant matter, the method comprising:

prescribing to a patient treatment by inhalation of the restricted substance;

entering the prescribed treatment data into a database;

providing the patient with a device adapted to provide the restricted substance according to the prescribed treatment and to record data of usage in the database.

In an exemplary embodiment of the invention, the method further comprises communicating with a central database to control fraud.

In an exemplary embodiment of the invention, the method further comprises requesting a resupply of the restricted substance.

In an exemplary embodiment of the invention, the method further comprises notifying authorities when a breach or unauthorized use has been detected.

In an exemplary embodiment of the invention, the method further comprises asking the patient to participate in trials of the restricted substance.

In an exemplary embodiment of the invention, the method further comprises detecting fraud by logging usage data on a base component and a modular component, the modular component comprising the restricted substance.

There is provided in accordance with an exemplary embodiment of the invention, a method of manufacturing a tape of plant matter comprising an active substance, the tape adapted for use with a device for automatically applying localized heat to extract the substance, the method comprising:

grinding the plant material without substantially physically damaging the active substance;

sieving the ground plant material to isolate small particles;

measuring the concentration of active substances the small particles; and pressing the small particles into the tape.

In an exemplary embodiment of the invention, sieving is performed a plurality of times to isolate particles of different sizes.

In an exemplary embodiment of the invention, a size of particles ranges from about 100 µm to about 700 µm.

In an exemplary embodiment of the invention, pressing is performed on a material having apertures with a size smaller than the size of the small particles.

In an exemplary embodiment of the invention, the method further comprises marking the tape with the concentration of the active substance.

There is provided in accordance with an exemplary embodiment of the invention, a tape for therapeutic drug delivery comprising:

plant matter comprising an active substance, said plant matter organized with a predetermined amount of said active substance per unit area of said tape.

In an exemplary embodiment of the invention, the tape is organized as a roll.

In an exemplary embodiment of the invention, the active substance comprises a restricted drug.

In an exemplary embodiment of the invention, the tape comprises a sufficient amount of the active substance for a plurality of treatment doses.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 14 is a table of an example of a dosing profile delivered to the patient using the device, in accordance with an exemplary embodiment of the invention;

FIGS. 15A-15C are some examples of database entries, in accordance with an exemplary embodiment of the invention.

DESCRIPTION OF SPECIFIC EMBODIMENTS OF THE INVENTION

Figure 1A:
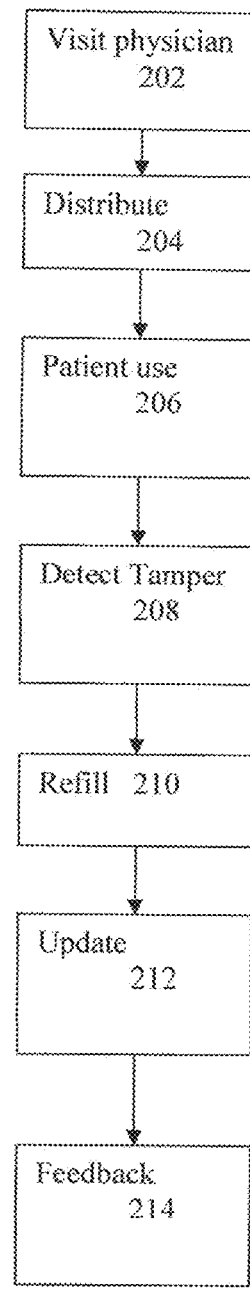
FIG. 1A is an exemplary method of substance delivery, in accordance with an exemplary embodiment of the invention.

The present invention, in some embodiments thereof, relates to a drug delivery device and method, and more particularly, but not exclusively, to a device and method for delivery of a substance extracted by local heating of plant matter.

An aspect of some embodiments of the invention relates to a device which selectively extracts substances from a material by localized heating, for example, by conduction, convection and/or radiation. Optionally, the material is comprised of organic matter. Alternatively or additionally, the material is comprised of any suitable compositions, for example, synthetic and/or pharmaceutical compositions. Optionally, the organic matter is heated sufficiently quickly to a temperature suitable for forming a vapor. In an exemplary embodiment of the invention, the organic matter is organized as a moving element which can be selectively and/or locally activated. Optionally, the organic matter is organized as a tape or as a plurality of tapes.

In an exemplary embodiment of the invention, the organic matter is processed without damaging the substances in the organic matter. Optionally, the organic matter retains a macroscopic plant structure.

In an exemplary embodiment of the invention, the substances are active, for example, having drug effects. Optionally or additionally, the substances are activated by the heating. In some embodiments of the invention, the substances have a therapeutic effect, for example, pain and/or nausea reduction.

In an exemplary embodiment of the invention, the substances are restricted drugs that people might illegally share, non-limiting examples of restricted substances and the plants they can be obtained from include; Cannabinoids e.g. tetrahydrocannabinol (THC) from *Cannabis*, diterpenoids e.g. salvinorin A from *Salvia*, Alkaloids e.g. benzoylmethylecgonine from the coca plant, Tryptamines e.g. psylocibin from mushrooms and DMT from example, from a variety of plants. Alternatively, the substances are not restricted, for example, tobacco. Alternatively, the substances are not illegal, but pose a hazard if administered incorrectly and/or to a person that does not require them, for example, chemotherapy drugs.

In an exemplary embodiment of the invention, the organic matter is not pharmaceutical grade, for example, does not require standard pharmaceutical regulatory approval for administration. Optionally, the organic matter is naturally grown. Optionally, the organic matter is commonly available.

In an exemplary embodiment of the invention, the tape is organized with a predetermined amount of active substance per unit of volume and/or surface area. For example, the tape is organized in units, for example, about 10 mg of source material, or about 2 mg, about 5 mg, about 15 mg, about 20 mg, or other smaller, intermediate or larger values are used. Optionally, the units are the smallest clinically useful doses that would be administered to a patient. Alternatively or additionally, the units represent the resolution of the device in administering doses, for example, the device being unable to regulate doses below the units. Optionally, the tape and/or a data carrier encode the information, for example, whether the amount is constant or varies along the tape. Optionally, the tape is substantially uniform throughout, for example, having a thickness of, for example, about 0.2 mm, about 0.4 mm, about 0.5 mm, about 0.6 mm, about 0.8 mm, about 1.0 mm, or other smaller, intermediate or larger thicknesses are available. Alternatively, the tape is non-uniform, for example increasing in thickness and/or density of active substance from one end to another, for example, to allow titration of doses up or down. Optionally or additionally, the units are separated by spaces which do not release drugs when heated, for example, empty spaces and/or inert materials.

In an exemplary embodiment of the invention, the tape contains a sufficient amount of raw material for a plurality of doses, for example, for at least 2 doses, at least 5, 10, 20, 50, 100 doses, or other smaller, intermediate or larger numbers of doses. In an exemplary embodiment of the invention, the tape contains, for example, at least 1 gram of raw materials, or at least 5 grams, 10 grams, 15 grams, 20 grams, 50 grams, 100 grams, or other smaller, intermediate or larger amounts are used.

In an exemplary embodiment of the invention, areas and/or volumes of the tape are automatically heated in a controlled manner to release and/or deliver vapors. Optionally, the tape is moved relative to the heat source, for example, spooled over the heating source. In an exemplary embodiment of the invention, an area of tape heated at any one time is, for example, about 60 mm$^2$, or about 10 mm$^2$, about 20 mm$^2$, about 40 mm$^2$, about 80 mm$^2$, about 100 mm$^2$, or other smaller, intermediate or larger areas are used.

In an exemplary embodiment of the invention, any area of tape can be delivered in any suitable manner. Optionally, tape is moved continuously, for example, the heat source is applied continuously as the tape is spooled, for example, at a rate of about 0.1 mm/second, or 0.3 mm/second, 0.5 mm/second, 1 mm/second, 1.5 mm/second, 2 mm/second, 3 mm/second, or other smaller, intermediate or larger speeds are used. Alternatively, the tape is moved in steps, for example, the heat source is applied to a stationary area of tape to extract the drugs, then the tape is advanced forward to position the next area for application of heat.

In an exemplary embodiment of the invention, heat is applied continuously to extract drugs from the raw material, for example, until the entire dose has been delivered. Alternatively, heat is applied is bursts (e.g., turned on and off), releasing sub-doses of the material. Optionally, the tape is heated to release vapors when the patient is inhaling. Optionally or additionally, the tape is not heated when the patient is not inhaling.

In some embodiments of the invention, the heat source is moved, with the tape being stationary.

In an exemplary embodiment of the invention, the tape is taken up at the end (e.g., after being heated), for example, stored in a storage chamber. Optionally, the tape is spooled in the storage chamber. Alternatively, the tape is a closed loop.

In some embodiments of the invention, the plant matter is organized into other compacted shapes, such as a disc or cylinder. Optionally, the tape is divided into sections, for example, physically cut up into pieces. Optionally, each piece represents a predetermined drug dose. Optionally, each piece is heated independently to release the drug dose.

In an exemplary embodiment of the invention, the amount of substance released from the tape is controlled, for example, by heating one or more areas of the tape are to release the predetermined dose of the substance. Optionally, the dose is determined by the user. Alternatively or additionally, the dose is determined by the physician.

In an exemplary embodiment of the invention, the tape is packaged for distribution. Optionally, the tape is hermetically sealed, for example, to prevent moisture damage. Optionally or additionally, the package is labeled with details related to the extraction of the selected dose of active substance from the tape, for example, the concentration of the active substance in the tape and/or the speed, time and/or temperature required to extract a unit of active substance from the tape. Optionally or additionally, the package is provided with a unique ID, allowing for tracking, for example, to detect unauthorized use.

In an exemplary embodiment of the invention, one or more tapes comprises two or more different raw materials that vaporize into two or more different drugs. Optionally, the materials alternate, for example, in parallel along the short axis of the tape. Alternatively, the materials are divided along the long axis of the tape. Optionally, the release of each drug is independently controlled.

In an exemplary embodiment of the invention, one side of the tape is in contact with a material having apertures large enough to let gas out, but small enough to contain residue of the heated organic matter. Optionally the aperture size is related the vegetable matter, for example, for *Cannabis* particle sizes of 25 μm-700 μm, or 40 μm-100 μm, or 50 μm-70 μm, or 25 μm-500 μm or 30 μm-300 μm, or 100 μm-500 μm, or 500 μm-700 μm, or other smaller, intermediate or larger sizes are used.

In an exemplary embodiment of the invention, the apertures cover for example, about 1% of the surface area of the material, or about 5%, about 10%, about 15%, about 20%, about 25%, about 30%, about 40%, about 50%, or other smaller, intermediate or larger values are used.

In an exemplary embodiment of the invention, one side of the tape is in contact with a heat conducting material that transfers heat from a heating element on one side to the organic matter on the other side without substantially distributing the heat along the material, for example, Kapton (e.g., available from Dupont). Alternatively or additionally, non-conductive areas separate conductive areas to prevent excessive heat diffusion.

In an exemplary embodiment of the invention, the tape is held tight enough to maintain the structure of the raw material in the tape arrangement. Optionally, the tape and/or materials in contact with the tape are held together by frictional forces as a result of the tight packing of the tape and/or spooling. Alternatively or additionally, the edges of the tape are sealed.

In an exemplary embodiment of the invention, the cross sectional area of the surface of the heated volume is substantially similar to a cross sectional area of a heating element, for example, about 100%, about 120%, about 140%, about 160%, about 200%, about 300%, or other smaller, intermediate or larger volumes are used.

An aspect of some embodiments of the invention relates to a method of manufacturing a tape for drug delivery by vaporization. Optionally, the method comprises processing (e.g., grinding) the raw material without damaging the active substance, for example, without bursting and/or breaking the trichomes of the *Cannabis* plant. Optionally or additionally, the method comprises sieving the ground raw material to obtain relatively small particle sizes, for example, less than 700 μm for *Cannabis*. In an exemplary embodiment of the invention, the concentration of active substances per unit (e.g., volume and/or weight) of the particle material are measured. In an exemplary embodiment of the invention, the method comprises pressing the ground raw material into a tape. Alternatively or additionally, material is folded over the leaves. Optionally or additionally, the pressing is performed on a material having apertures with a size smaller than the particle size of the raw material. Optionally or additionally, the method comprises cutting the material to size and fitting between support layers. Optionally or additionally, the method comprises labeling the tape with the strain chemical data.

An aspect of some embodiments of the invention relates to tapes designed for drug delivery by extraction of substances from the tape. Optionally, the source material is mixed with an inert, biocompatible, adhesive (e.g., FDA compliant high temperature thixtropic adhesive silicone sealant), and the tape is formed from the combined adhesive-source material. Alternatively or additionally, the source material is bound to an inert layer (e.g., hemp), so the source material remains in place on the inert layer. Bounding can take place, for example, by use of an inert, biocompatible adhesive. Optionally or additionally, the tape is perforated to allow vapors to escape. Optionally or additionally, the tape is stretched (e.g., adhesive and/or inert layers are flexible) when passing over the heating element, potentially allowing for vapors to escape.

An aspect of some embodiments of the invention relates to a system for remote monitoring and/or controlling drug delivery by extraction of an active substance by vaporization. In an exemplary embodiment of the invention, the system comprises an inhaler for controlled drug delivery by vaporization of a tape, and a database. Optionally, the database is accessible by one or more stakeholders, for example, healthcare providers, drug enforcement agencies, patients, drug producers, researchers.

An aspect of some embodiments of the invention relates to a method of controlling the use of a controlled substance by tracking usage of the substance. Optionally, the method comprises identifying 'wrong' behavior, for example, tampering with a module comprising the substance, administration of the substance above the set dose. Optionally or additionally, the method comprises disabling releasing of the substance when 'wrong' behavior has been identified. Optionally or additionally, the method comprises cartridges talking back to back when bought. Optionally or additionally, the method comprises wirelessly setting the limits for usage of the controlled substance, for example, to define 'proper' behavior.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Delivery Device

Figure 1B:
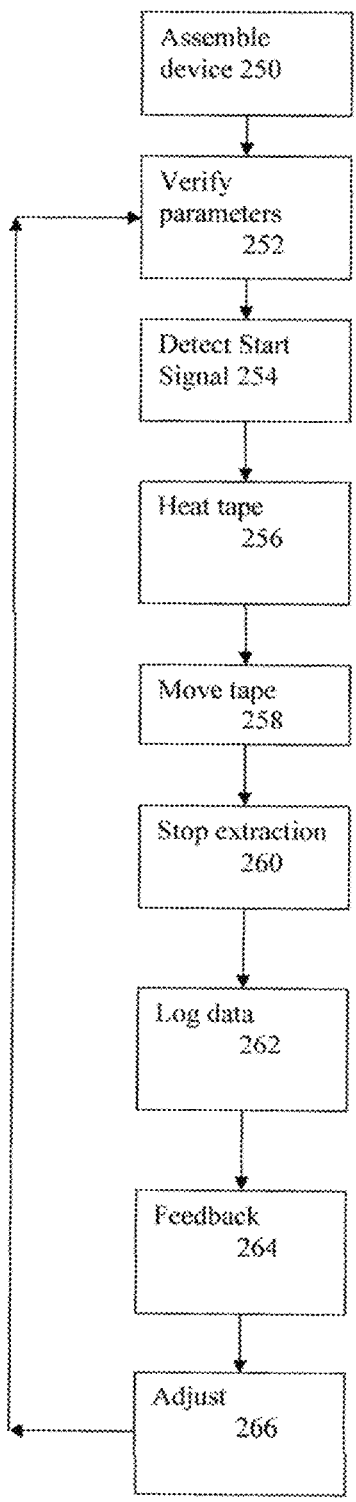
FIG. 1B is an exemplary method of operation of a delivery device, in accordance with an exemplary embodiment of the invention.
Figure 1C:
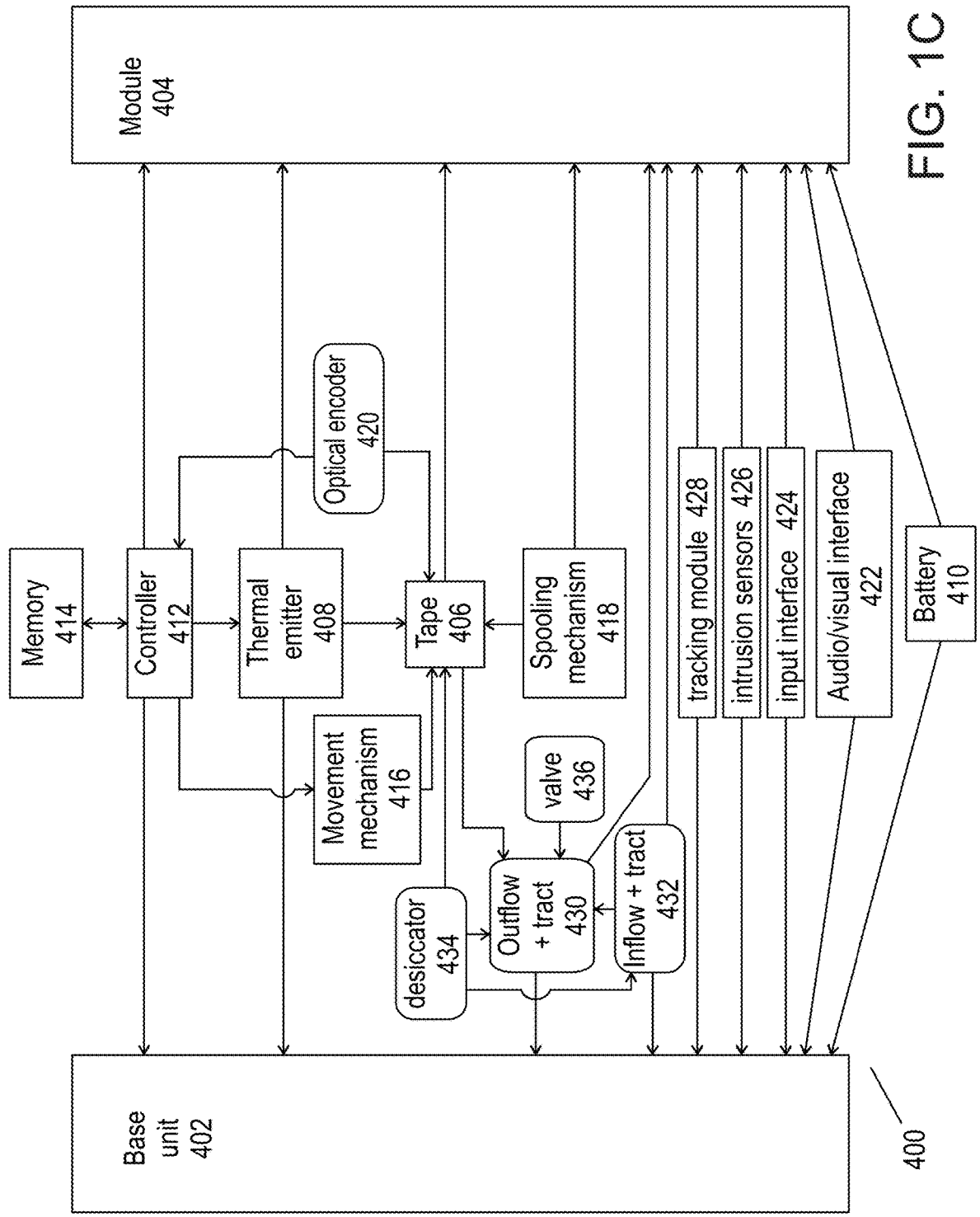
FIG. 1C is a block diagram of the delivery device, in accordance with an exemplary embodiment of the invention.

FIG. 1C is a block diagram of an exemplary delivery device 400 for releasing substances from matter, in accordance with an exemplary embodiment of the invention. A brief overview of device 400 is presented, with additional details provided.

In an exemplary embodiment of the invention, device 400 comprises a base unit 402, and an attachable module 404. Alternatively, unit 402 and module 404 are not separable.

In an exemplary embodiment of the invention, module 404 comprises one or more tapes 406 comprising one or more plant matter with one or more active substances.

In an exemplary embodiment of the invention, one or more thermal emitters 408 heats tape 406 to extract the substance. Emitter 408 is located on unit 402 and/or module 404.

In some embodiments of the invention, tape 406 is moved relative to emitter 408 by one or more movement mechanisms 416. Alternatively, tape 406 is not moved. Mechanisms 416 are located on unit 402 and/or module 404. Optionally, an optical encoder 420 reads patterns on tape 406 to determine the movement of tape 406. Encoder 420 resides on unit 402 or module 404. Optionally, one or more spooling mechanisms 418 unravel tape 406 and/or reform tape 406 into the roll form.

In some embodiments of the invention, controller 412 controls one or more of movement mechanism 416, optical encoder 420, thermal emitter 408. Controller 412 resides on unit 402 and/or module 404. Optionally, memory 414 is coupled to controller 412, to be read and/or written to.

In an exemplary embodiment of the invention, substances emitted from tape 406 travel to the patient through an outflow tract 430. Optionally, a valve 436 in tract 430 controls the rate of gas outflow. Optionally, an inflow tract 432 provides the inflow of air, and is in fluid communication with outflow tract 430.

In some embodiments of the invention, one or more desiccators 434 remove moisture from one or more of tape 406, outflow tract 430 and/or inflow tract 432.

In some embodiments of the invention, one or more batteries 410 power one or more of the described components. Batters 410 are located on unit 402 and/or module 404. Alternatively, other power sources are available, for example, a manually wound spring, and/or a wall socket plug.

In some embodiments of the invention, an audio and/or visual interface 422 provides data to the patient, for example, the remaining dose. Optionally or additionally, an input interface 424 allows the user to turn on the device and/or make adjustments to the dose profile. Interfaces 422 and/or 424 are located on unit 402 and/or module 404.

In some embodiments of the invention, one or more sensors 426 detect intrusion. Sensors 426 reside on unit 402 and/or module 404.

In some embodiments of the invention, one or more tracking modules 428 are used to locate and/or determine the identity of unit 402 and/or module 404.

Exemplary Method of Controlled Substance Delivery

FIG. 1A is an exemplary method of delivery of a substance, such as a vaporized active substance, in accordance with an exemplary embodiment of the invention. Optionally, the method relates to controlled medical supply, administration, tracking and/or research of organic substances, for example, restricted substances such as medical *Cannabis*. It should be noted that the method described in the flowchart is non-limiting. For example, some steps are optional. Furthermore, there can be other methods and/or other apparatus used to obtain the results.

Optionally, at 202, the patient is prescribed treatment, for example, as will be described in the section "PHYSICIAN VISIT".

Optionally, at 204, the patient is provided with the delivery device and/or tape, for example, as will be described in the section "DISTRIBUTION".

At 206, the patient uses the device, for example, as will be described in more detail in the section "PATIENT USE" and/or with respect to FIG. 1B.

Optionally, at 208, the patient attempts to tamper with the device and/or share the device with friends, for example, as will be described in the section "TAMPER".

Optionally, at 210, the patient requests a refill of medication, for example, as will be described in the section "REFILL SUPPLY".

Optionally, at 212, the data on the device is updated, for example, as will be described in the section "UPDATE".

Optionally, at 214, the patient provides information to one or more stakeholders, for example, as will be described in the section "FEEDBACK".

Optionally, one or more of 202, 204, 206, 208, 210, 212, 214 are repeated.

Exemplary Monitoring and/or Control System

Figure 2:
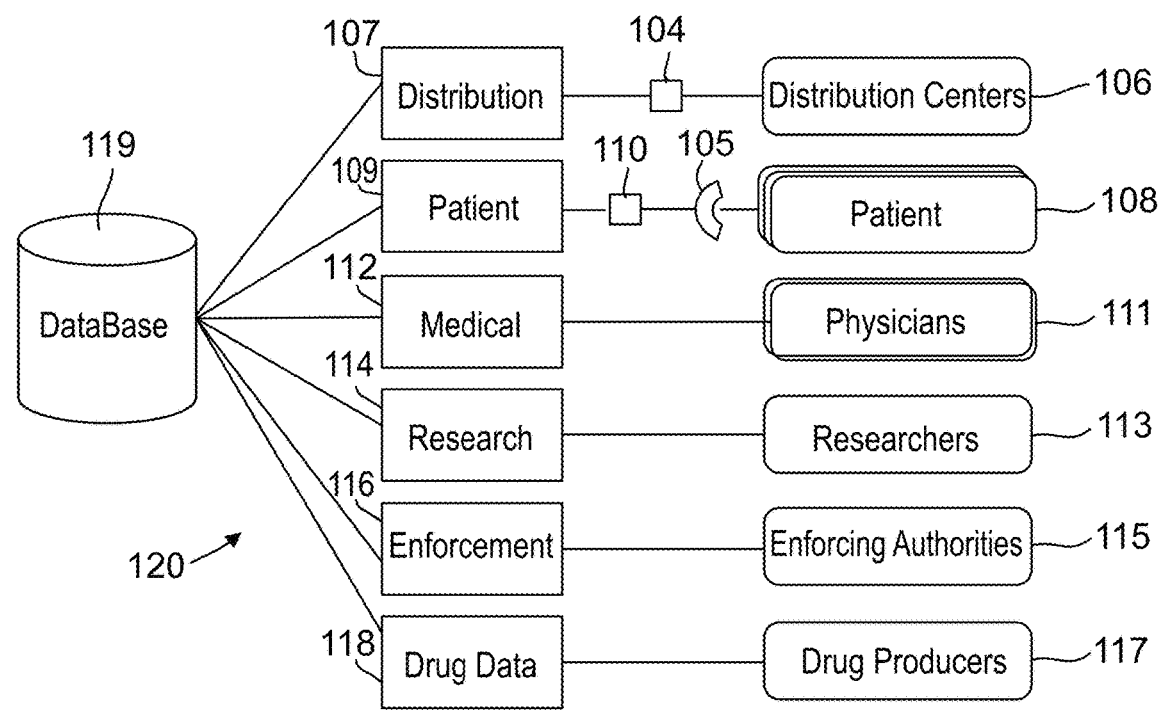
FIG. 2 is an illustration of a computerized system for monitoring and/or control of the administration of substances, in accordance with an exemplary embodiment of the invention.

FIG. 2 is an illustration of a computerized system 120 for monitoring and/or control of the administration of substances, in accordance with an exemplary embodiment of the invention. Optionally, system 120 is used to monitor, track and/or control the distribution of a regulated substance and/or the administration of the regulated substance, for example, medical *Cannabis*. Optionally, system 120 is centralized, for example, residing on a central server with internet access.

In an exemplary embodiment of the invention, system 120 comprises of a database 119 of one or more users, comprising of data related to the administration of the organic substance (for example, obtained from the device during use). Alternatively, information is stored on the device itself, optionally, with no central database.

In an exemplary embodiment of the invention, system 120 comprises a drug delivery device 105 coupled to a transmitter and/or receiver, which allows for control and/or monitoring of the functions of device 105 and/or uploading and/or downloading capabilities.

In an exemplary embodiment of the invention, delivery device 105 interfaces with database 119, for example, using a wired connection and/or a wireless connection. Some non-limiting examples of capabilities of system 120 include; registering dispensation of the drug, logging drug administration, tracing source-material, aggregating scientific data, and/or offering drug producers clinical and/or statistical data on the performance of their products. Further details about some of these functions will be provided herein.

In an exemplary embodiment of the invention, database 119 is divided into one or more domain specific partitions with user specific access capabilities. Optionally, a distribution dedicated domain 107, for example, accessed by distribution terminals 104 of distribution centers 106. Optionally or additionally, a patient domain 109, for example, accessed by personal computers 110 of either patients 108 and/or medical institutions, for example, through inhaler base units 105 provided to the patients for substance delivery. Optionally or additionally, a medical domain 112, for example, accessed by prescribing physicians 111. Optionally or additionally, a research domain 114, for example, accessed by researchers 113. Optionally or additionally, an enforcement domain 116, for example, accessed by enforcing authorities 115. Optionally or additionally, a drug data domain 118, for example, accessed by drug producers 117.

One or more potential advantages of the centralized system are to empower one or more stakeholders. For example:

Empower physicians, by enabling prescription of a medication from various known compositions, with exact dosing, remote administration control and logging.

Empower researchers, by harnessing and/or monitoring the breadth of data from a unique and aggregate interactive patient and/or drug database (for example, contrary to the contemporary disordered medical *Cannabis* treatment systems, and the feedback-limited pharmaceutical distribution system), allowing the researches to conduct detailed studies.

Empower the drug enforcing agencies and policing authorities, enabling complete raw material tracing capabilities, providing evidence for prosecution.

Empower drug producing entities, by providing constantly updated clinical and statistical data on the drugs produced and used, potentially assisting in the development of improved formulations.

Empower patients, with an affordable, efficient, convenient, safe, and/or effective medication, by allowing the patients to use the device any time, any where, without having to figure out the doses themselves.

Potentially the centralized system, maintains a complete monitoring infrastructure, for example, for restricted substance use, such as the medical *Cannabis* supply process.

Exemplary Database

FIGS. 15A-15C are some non-limiting examples of possible database entries, in accordance with an exemplary embodiment of the invention.

FIG. 15A is a sample entry recording drug administration to the patient. Optionally, the time and/or date of each treatment session is recorded. Optionally or additionally, the dose taken per session and/or the time period required for the dose administration is recorded (the prescription can be stored separately, for example, as described with reference to FIG. 14 below). Optionally or additionally, the ID of the cassette and/or tape is recorded (e.g., source material), for example, for tracking purposes (e.g., in the example the user changed cartridges). Optionally or additionally, the user provides subjective data related to the treatment (e.g., mobile phone applications, internet, phone surveys), for example, changes in pain. For example, any suitable method and/or device that directly interfaces with the database and/or other data center that identifies the specific user. For example, the user may user a mobile phone application to log in and input subjective data, for example after every administration. Optionally or additionally, relevant clinical data associated with the treatment is recorded, for example, blood test results.

FIG. 15B illustrates some sample entries showing one or more of; patient medical information (e.g., medical history), patient personal information, physician information and/or prescription information.

FIG. 15C is a sample entry for tracking the modules containing the drugs. For example, 'Product ID' refers to the drug the physician prescribes. For example, 'Issue ID' refers to the ID assigned to the specific cassette and/or tape. For example, 'Manufacturing ID' refers to the batch that the tape was prepared from. Optionally, the expiration date is stored. Optionally, the formulation of the active substances is stored.

Physician Visit

In an exemplary embodiment of the invention, a patient (e.g., patient 108) experiencing a medical condition visits a physician (e.g., physician 111) in order to obtain a prescription and/or recommendation for treatment by inhalation of one or more heated naturally growing substance, and/or one or more other materials released by heat. In some cases, patient 108 suffers from a chronic condition requiring administration of medication on a regular basis, for example, neuropathic pain, and/or cancer pain. Optionally, patient 108 is prescribed a restricted substance, for example, medical *Cannabis*. In some cases, patient 108 is addicted to a drug, and requires help to quit, for example, tobacco smoking or opioids.

In an exemplary embodiment of the invention, physician 111 selects the dosing profile for the patient, for example, the number of treatments per day and/or the dose per treatment. Optionally, physician 111 allows patient 108 to select the drug dose himself, but physician 111 places a limit on the dose per unit of time. Optionally or additionally, physician 111 selects a titration profile, for example, allowing increases in the dose over time, or decreasing the dose over time (e.g., to control drug withdrawal symptoms). Optionally, physician 111 prescribes a plant complex, for example, medical *Cannabis*: 20% THC, 5% Cannabidiol (CBD).

In an exemplary embodiment of the invention, physician 111 accesses and/or enters the patient data and/or prescription data into centralized computerized system 120, for example, medical domain 112 of database 119. Optionally or additionally, physician 111 updates database 119 with the changes in the prescription details for patient 108. Optionally, physician 111 is provided with remote access to system 120, for example, from home and/or office and/or from a smartphone. Alternatively or additionally, physician 111 updates the device directly. Alternatively or additionally, physician 111 gives out the pre-programmed inhaler to the user, and the user buys a standard drug by prescription. Non-limiting examples of data entered by physician 111 include; dosing profile (e.g., number of permitted administrations per day, size of doses, allowable titration limits), expiry date of dose regiments (e.g., when patient needs to return for follow-up) and/or any other control and/or data physician 111 may find beneficial to the treatment process.

In an exemplary embodiment of the invention, one or more of domains; patient 109, medical 112, research 114, enforcement 116 and/or drug producers 118 are granted access privileges to data stored in main database 119. Non-limiting examples of access privileges include:

Patient 109 being able to view all data (e.g., prescription and/or usage), but unable to change the data.

Healthcare workers accessing medical 112 domain, being able to change prescription data, but not the usage data.

Researchers accessing research 114 domain, being able to only view the pre-approved data (e.g., approved by ethical committee) required for the research.

Enforcement officials accessing enforcement 116 domain, being able to view only the detected breaches in usage. The rest of the data can be protected by privacy laws.

Drug producers 118 being able to view only the pre-approved data required for post-market surveillance.

Example of Dosing Profiles

FIG. 14 is a non-limiting example of a dosing profile, in accordance with an exemplary embodiment of the invention. In this example, three patients have been prescribed treatment with THC for medical conditions; cancer pain and/or nausea, Tourette's, chronic pain (e.g., Spinal Cord Injury).

In some embodiments of the invention, the number of inhalations per day is prescribed, for example, 1, 3, 5, or other smaller, intermediate or larger numbers are used. Optionally, the number of actual inhalations taken by the patient are recorded, for example in the database.

In some embodiments of the invention, the dose per inhalation is prescribed, for example, about 2 mg, about 4 mg, about 6 mg, about 8 mg, about 10 mg, about 12 mg, about 14 mg, or other smaller, intermediate or larger doses are used. Optionally, the time required per inhalation to obtain the dose is determined, for example, calculated by the device according to the dose and the tape concentration, for example, about 1 second, about 2 seconds, about 4 seconds, about 5 seconds, about 6 seconds, about 7 seconds, or other smaller, intermediate or larger time frames are used. Optionally or additionally, the actual amount inhaled and/or the time period of inhalation are recorded, for example in the database.

In some embodiments of the invention, the pause between inhalations is prescribed, for example, to allow the patient to rest before the next dose. Alternatively or additionally, the time between inhalations is recorded, for example, the patient is able to determine the rest time.

In some embodiments, the total start and end time are recorded (e.g., time stamps). Optionally, the total dose taken during the time is recorded. Optionally or additionally, the total time taken is recorded, for example, the gross time (e.g., including pauses) and/or the net time (e.g., not including pauses).

In some embodiments, the prescribed data is compared to the actual usage data, for example, to detect fraud and/or compliance with treatment.

Distribution

In an exemplary embodiment of the invention, patient 108 approaches distribution center 106 to obtain the prescription, for example, in person or remotely using a secure login, or through an intermediary such as a nurse.

In an exemplary embodiment of the invention, patient 108 is registered in database 119, for example, by distribution terminal 104 via distribution domain 107. Database 119 can reside on a central server (e.g., accessible by network access). Optionally, registration occurs, for example, with the patient's personal details, for example, medical license to obtain the restricted substance. Optionally or additionally, distribution center 106 accesses distribution domain 107 (e.g., manually by staff, and/or automatically), entering the patient identification details to main database 119, for example, in order to establish a supply profile for the patient. Optionally, if physician 111 already entered specific prescription details for patient 108, the details are already bound to the patient supply profile. Alternatively, the prescription is entered manually and/or automatically into distribution terminal 104.

In some embodiments of the invention, a pharmacy directly provides the drugs to the patient.

In some embodiments of the invention, the pharmacy and/or distribution center 106 reads the previous module (e.g., returned by the patient). Optionally, the new dosage is determined according to the previous dosage, for example, the dose is repeated. Alternatively or additionally, the previous module is read to discover 'tampering' (e.g., breaches in usage), for example, by comparing the usage data and the amount of remaining substance. Alternatively or additionally, the pharmacy programs the new module and/or the central database with messages, for example 'user lost one module', 'user tampered with module'. The messages can be tracked over time to determine patterns in breach of use, for example, user repeatedly losing modules.

Figure 3:
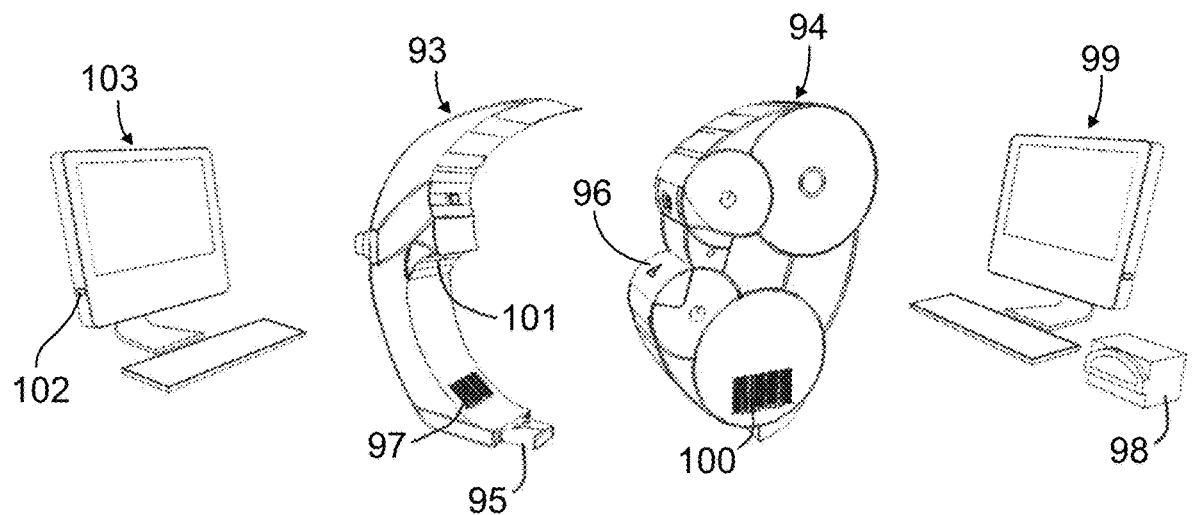
FIG. 3 is a schematic illustration of a Medical *Cannabis* Cassette and delivery device, in accordance with an exemplary embodiment of the invention.

FIG. 3 illustrates a medical *Cannabis* cassette 94 containing the prescribed drug, in accordance with an exemplary embodiment of the invention. In an exemplary embodiment of the invention, cassette 94 is designed to fit into an inhaler base unit 93 (e.g., unit 105), forming a complete inhalation device. Optionally, base unit 93 is provided to the patient, and kept by the patient for use with multiple replaceable cassettes 94.

In an exemplary embodiment of the invention, a unique ID of inhaler base unit 93 is read, for example, by a reader unit (e.g., software module on a general purpose computer and/or dedicated circuitry), for example, by scanning a printed barcode and/or quick response (QR) code 97 with a barcode reader device 98, which optionally is coupled to a distribution terminal 99 (e.g., terminal 104). Alternatively, inhaler base unit 93 communicates physically and/or wirelessly with distribution terminal 99, for example, the unique ID residing as an RFID. Alternatively, inhaler base unit 93 is plugged into a special reader and/or USB socket.

In an exemplary embodiment of the invention, issued cassette 94 comprises a unique ID 100 (e.g., barcode, RFID). Optionally, ID 100 is associated with the patient ID entry in database 119. In some embodiments of the invention, unique ID 100 is used to trace and/or monitor cassette 94 comprising controlled substances, for example, through database 119.

In an exemplary embodiment of the invention, the distribution center uploads to the control module residing on inhaler base unit 93 and/or cassette 94 the dose regiment prescribed by physician 111. Uploading can be performed by a programmer unit (e.g., software on a general purpose computer and/or dedicated circuitry). Alternatively, the prescription is loaded to cassette 94, optionally communicated to the controller on unit 93, for example, by the patient and/or pharmacist, when the two parts are assembled. In an exemplary embodiment of the invention, the uploaded parameters affect and/or limit the entire vaporization process with regard to the specific patient, for example, by limiting the allowable daily dose of the substance.

In an exemplary embodiment of the invention, unique ID 97 of inhaler base unit 93 is associated with the supply profile of the patient. In an exemplary embodiment of the invention, when issuing unit 93, and/or a cassette 94, each patient profile in the database is bound to the unique identifier of the specifically issued unit, for example, by means of the electronic and/or optical identifiers. Optionally, the distribution center completes the synchronization of the supply profile of the patient with the main database via the distribution domain.

In an exemplary embodiment of the invention, the distribution center and/or pharmacy communicate with an inventory control system (e.g., in communication with database 119). Optionally, the inventory control system tracks the inventory of the individual distribution centers and/or pharmacies. Alternatively or additionally, the inventory control system globally tracks the supplies across the plurality of pharmacies. Some non-limiting examples of the functions of the inventory control system include; tracking the supply of cassettes 94, tracking the supply of inhalers 93, tracking the supply of different formulations of tapes, ordering new supplies as needed to maintain a sufficient inventory.

Exemplary Dispensing Device

Figure 4A:
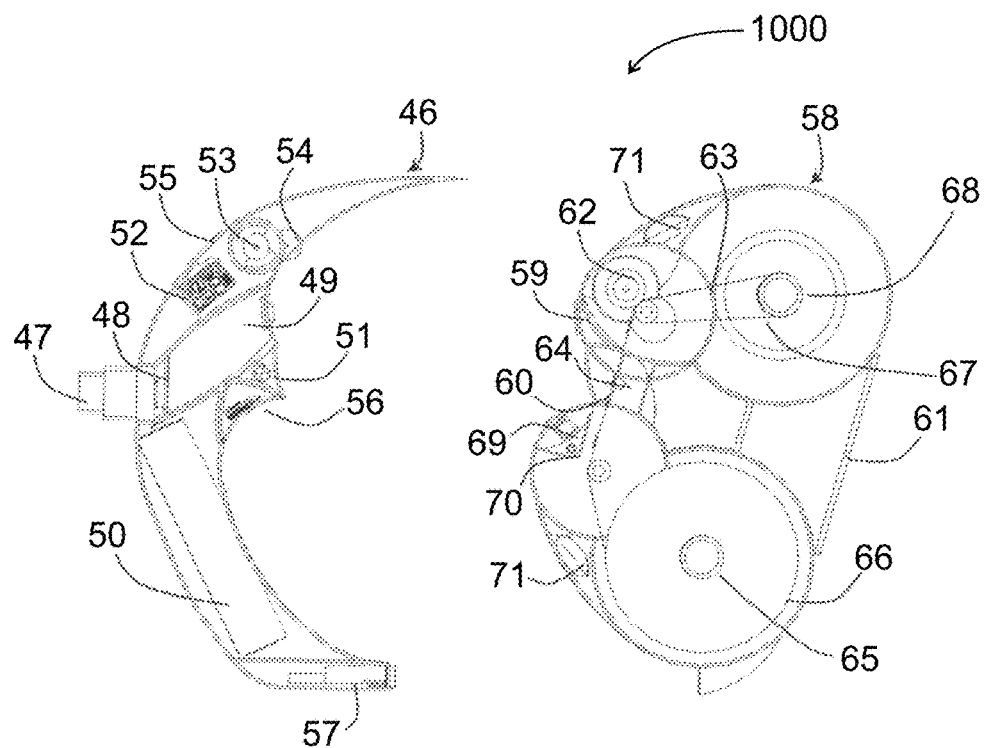
FIG. 4A is a schematic of two separable components of an inhaler; a base unit and a cassette unit, in accordance with an exemplary embodiment of the invention.
Figure 4B:
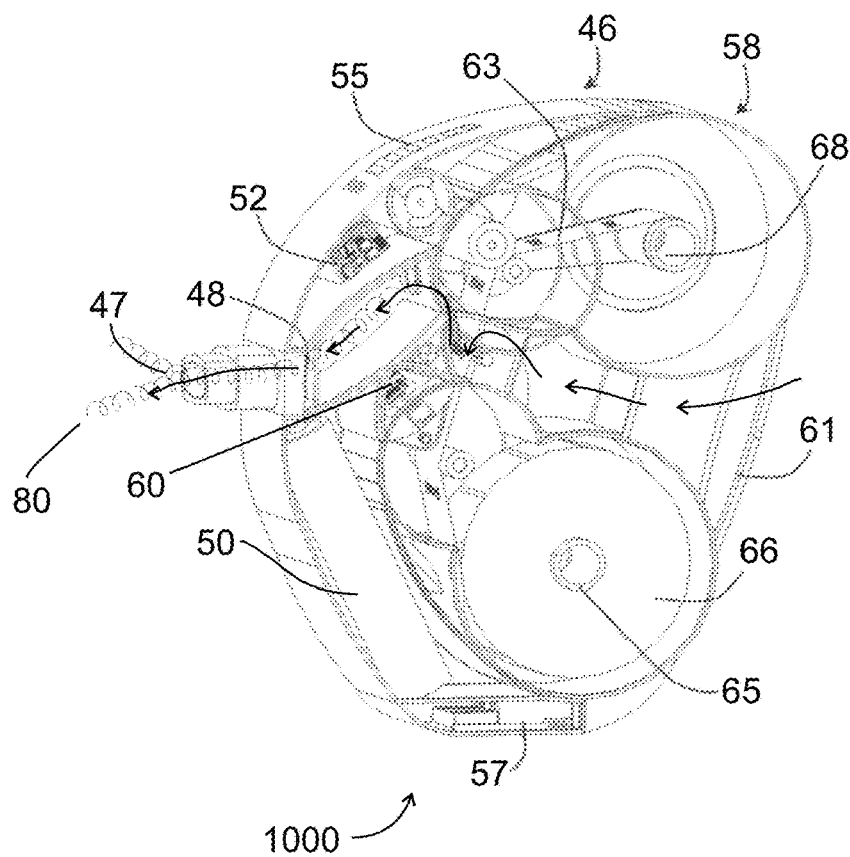
FIG. 4B illustrates the parts of FIG. 4A assembled into the inhaler, in accordance with an exemplary embodiment of the invention.
Figure 7B:
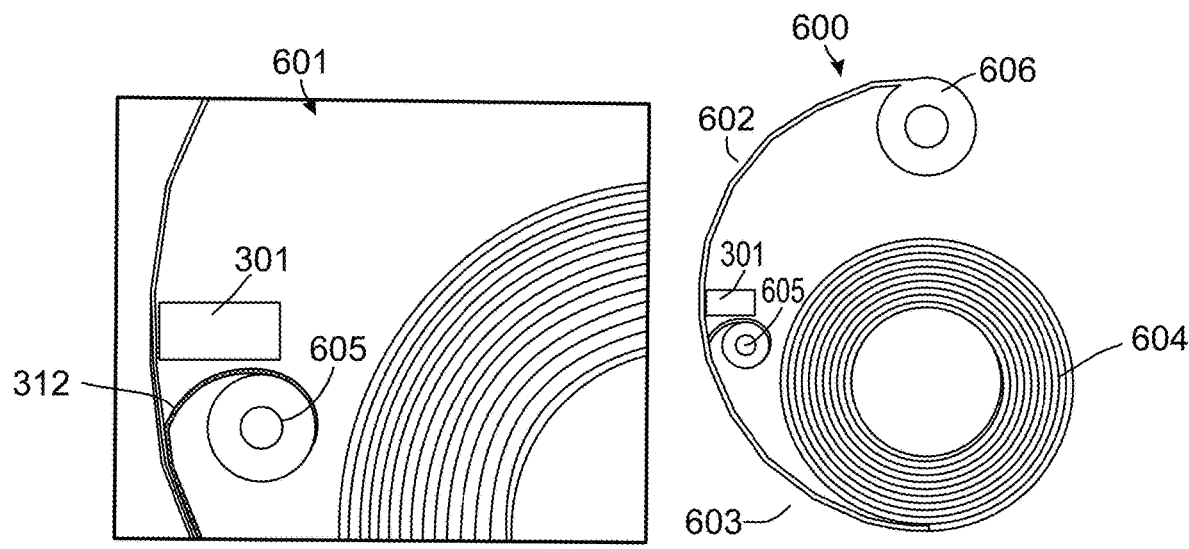
FIG. 7B is a spooling mechanism, for example, for use with the tape of FIG. 6C, in accordance with some embodiments of the invention.

FIG. 4A illustrates two separable components of an inhaler 1000; a base unit 46 and a cassette unit 58, in accordance with an exemplary embodiment of the invention. FIG. 4B illustrates the parts of FIG. 4A assembled into inhaler 1000, in accordance with an exemplary embodiment of the invention.

In an exemplary embodiment of the invention, inhaler 1000 is portable. For example, the weight of inhaler 1000 is no more than 100 grams, no more than 200 grams, no more than 300 grams, no more than 500 grams, or other smaller, intermediate or larger values are used.

Alternatively, in some embodiments, the inhaler is a room-standing device. Optionally, the room inhaler is designed to be placed on the table, for example, by the inhaler having a substantially flat base. Optionally or additionally, the room inhaler is powered by plugging into an electrical outlet.

In an exemplary embodiment of the invention, inhaler 1000 is adapted to be handheld, for example, by one hand.

In an exemplary embodiment of the invention, base unit 46 comprises a mouthpiece 47 for inhaling vapors. Optionally, vapors can be inhaled directly into the respiratory system of the patient. Alternatively, mouthpiece 47 can be attached to other elements, for example, to a mask and/or nasal cannula, optionally with supplemental oxygen, for example, to deliver therapy to debilitated patients.

In an exemplary embodiment of the invention, mouthpiece 47 is in fluid communication with at least one valve 48. Optionally, valve 48 is one way, for example, to prevent expired air from entering further into inhalation device 1000. Optionally or additionally, valve 48 regulates the flow of air therethrough, for example, limiting the air flow to a threshold value. Potentially, placing an upper limit on air flow prevents excessive cooling of the heating element and/or helps to ensure correct vaporization. Optionally or additionally, valve 48 is selectively opened and closed to regulate the administration of the drug, for example, controlled by an electronic switch. In some embodiments, valve 48 is located in unit 46. In some embodiments, valve is located in unit 58.

Figure 5A:
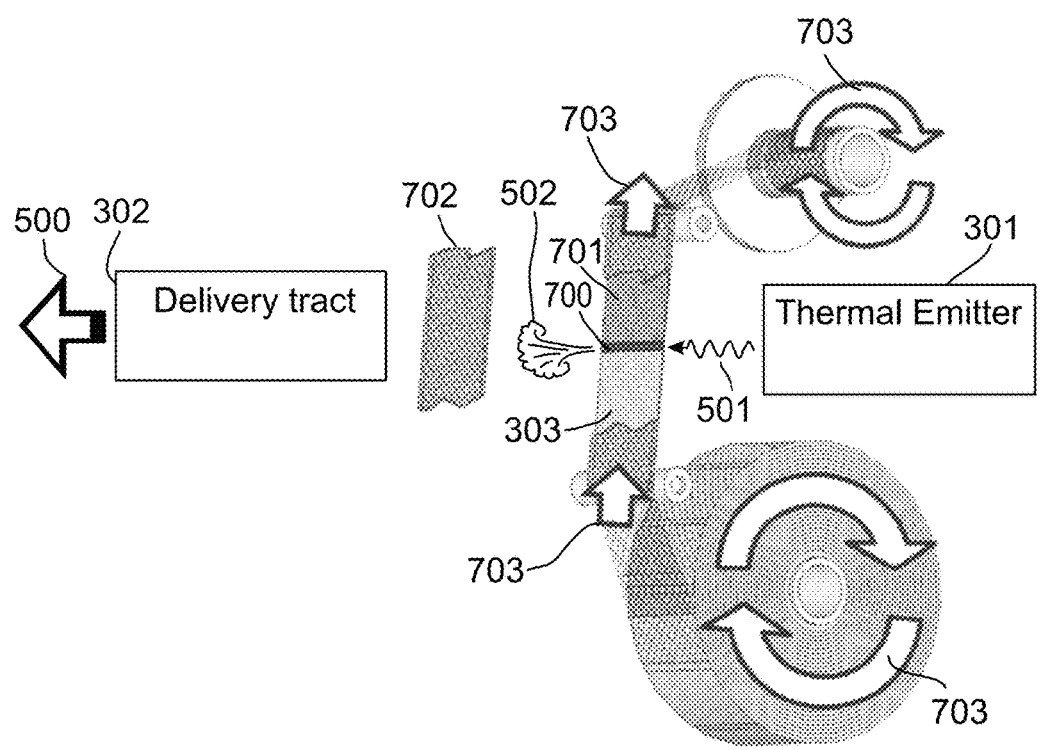
FIGS. 5A-5B are schematics depicting the movement of a tape relative to a thermal emitter, FIG. 5B also illustrates the flow of air through the device, in accordance with an exemplary embodiment of the invention.
Figure 5B:
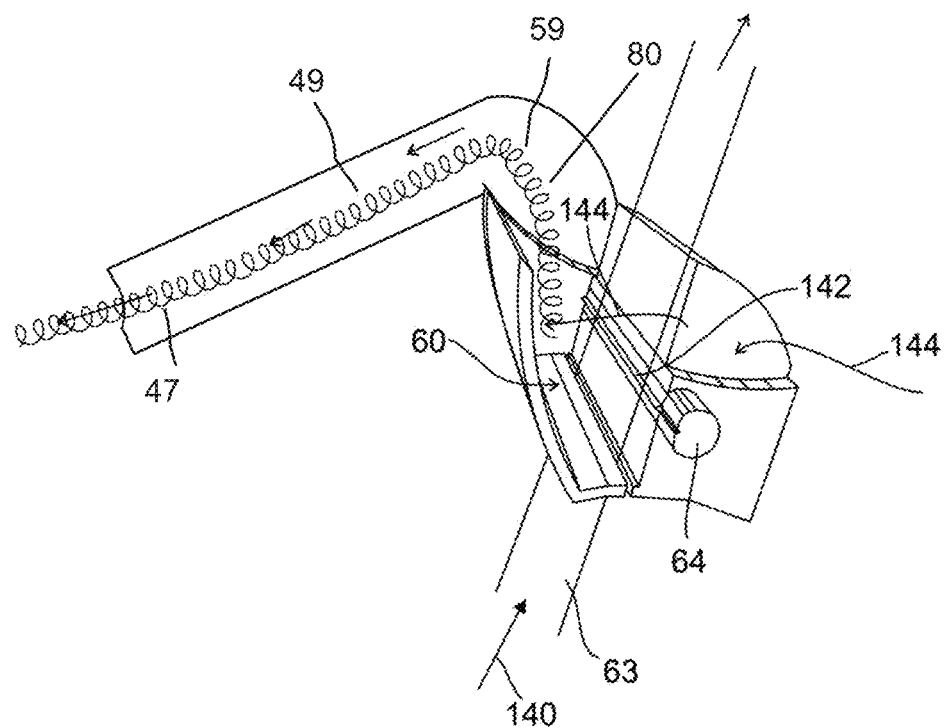
Figure 7A:
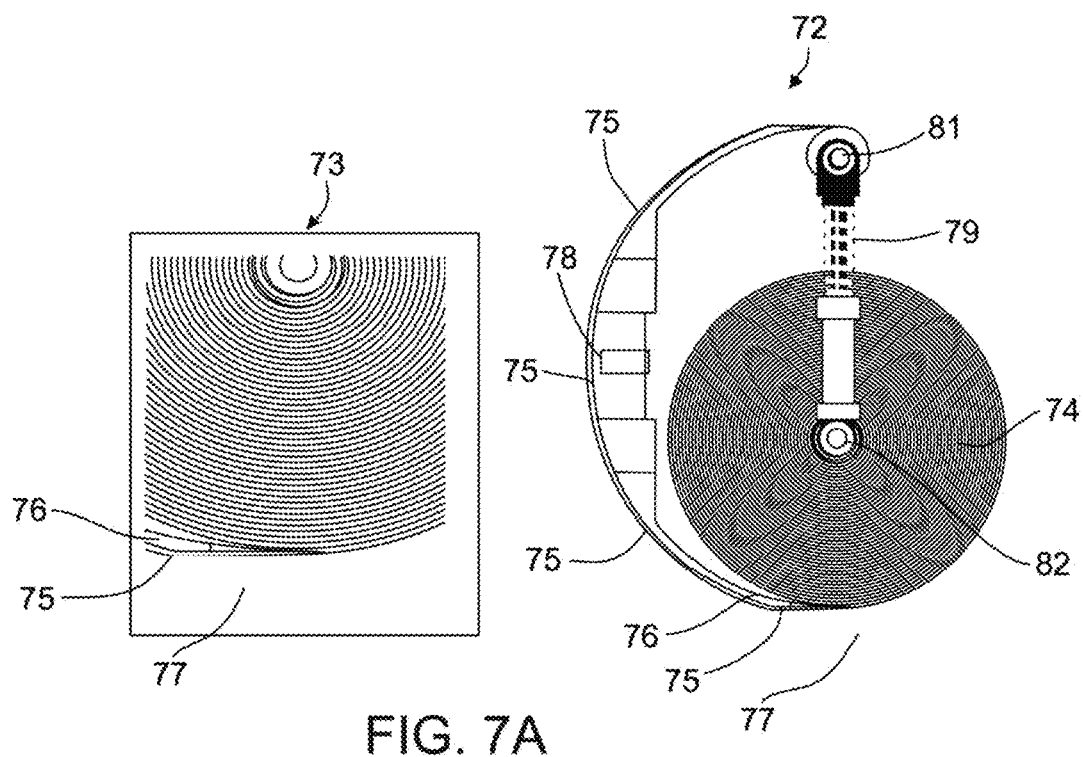
FIG. 7A is a spooling mechanism, for example, for use with the tape of FIG. 6A, in accordance with some embodiments of the invention.

FIG. 5B is a schematic illustration showing the flow of fluid in the device, in accordance with an exemplary embodiment of the invention. Fluid, for example room air 144, enters the device, for example, through an inflow tract. Air 144 mixes with vapors 80 formed from heated tape 63. Mixing occurs in optional vapor chamber 60. Vapor 80 and air 144 travel to an optional air transfer tract 59, optionally located above chamber 60, to direct the rising vapors 80 away from chamber 60. Optionally, tract 59 is in fluid communication with an optional air intake tract 49. Optionally, mouthpiece 47 is in fluid communication with air intake tract 49. The patient can inhale vapor 80 using mouthpiece 47. In some embodiments, vapor chamber 60 is housed in unit 46. In some embodiments, vapor chamber 60 is housed in unit 58. In some embodiments, vapor chamber 60 is formed when units 46 and 58 are combined.

In some embodiments of the invention, vapors travelling away from chamber 60 are cooled to a temperature below 60 degrees Celsius before being inhaled, or to a temperature below 70 degrees, below 50, degrees, below 40 degrees, below 30 degrees, or other smaller, intermediate or larger values are used. Optionally, vapors are cooled by room air entering vapor chamber 60, for example, by an air intake tract 61, located in unit 47 and/or unit 58. Alternatively or additionally, vapors are cooled by a heat pump, such as a Peltier element.

In some embodiments of the invention, cassette unit 58 comprises a thermal emitter 64. Optionally, emitter 64 applies heat by contact. Alternatively, emitter 64 applies heat without contact. Optionally, emitter 64 is an electrical resistor, made out of one or more alloys, for example, FeCrAl, Nichrome, NickelTitanium, Tungsten, Molybdenum. In a non-limiting example, the dimensions of element 64 are 30 mm×2 mm×0.15 mm. The 30 mm dimension substantially corresponds to the width of the tape, to heat the entire width of tape. The 2 mm dimension has been selected to heat an area of tape large enough to release a substantial volume of substance. Alternatively or additionally, emitter 64 is a laser or infrared (IR) emitter, e.g., diode. Alternatively or additionally, emitter 64 is chemically based. Alternatively or additionally, emitter 64 is a fire. Alternatively or additionally, emitter 64 is a pyrolitic converter and/or heated.

In an exemplary embodiment of the invention, element 64 resides on unit 46. Optionally, emitter 64 is controlled by controlled circuitry 51. Optionally, circuitry 51 resides on unit 46. Alternatively, circuitry 51 resides on unit 58. In some embodiments, thermal element 64 and control circuitry 51 reside on different parts. Assembling the parts connects element 64 and circuitry 51 to produce a functioning unit.

In some embodiments of the invention, cassette 58 comprises a packed source material tape 63 optionally organized as a supply reel 65, for example as described in the section "TAPE". Optionally, reel 65 is a prefabricated roll of packed source-material tape comprised of a medical grade *Cannabis* 66. Optionally, used tape 63 (after being heated) is rolled onto an optional intake reel 68. Optionally, reel 68 is driven by an intake transport slip belt 67. Alternatively, reel 68 is driven by a dedicated motor. Optionally tape 63 comes in contact with or passes near to a moisture absorbing medium 71 (e.g., desiccator) to remove excess moisture, for example, before being heated. Alternatively or additionally, moisture absorbing medium 71 removes excess moisture during storage and/or maintains tape 63 in a desiccated state. Alternatively or additionally, desiccator 71 is located in one or more of mouthpiece 47, air intake tract 49, air transfer tract 59 and/or vapor chamber 60, to remove moisture due to inhalation.

In some embodiments of the invention, tape 63 is pulled along by precision tape transport mechanics 62, optionally residing in cassette 58. Mechanics 62 are optionally further regulated by precision driving mechanics 54, for example, providing interlocking gears. Mechanics 54 are located on cassette 58 or unit 46. A motor 53 is coupled to optional mechanics 54 or directly to mechanics 62. Motor 53 is housed in cassette 58 or unit 46. In some embodiments, a spring is used, rather than motor 53. Potentially, the use of the spring provides a longer shelf life and/or can use smaller batteries.

Optionally, an optical encoder reads marks on tape 63 to tell how far tape 63 moved.

In some embodiments of the invention, a control module 52 controls heat generated by one or more thermal emitters 64 (e.g., by regulating power through circuitry 51) and/or movement of tape 63 (e.g., by regulating power to motor 53), to control heating and/or temperature of the tape unit. Optionally, different temperatures are applied to the same tape, for example, to release different substances. Alternatively or additionally, different temperatures are applied to different tapes. Module 52 is housed on cassette 58 or base unit 46. In some embodiments, module 52 is coupled to a computer interface 57, for example, wired communication using a USB port and/or wireless connection using a transmitter and/or receiver. Interface 57 is located on cassette 58 or unit 46.

In some embodiments of the invention, a dose display meter 55 provides visual and/or audio output about the delivered dose. Meter 55 can be located on the exterior of unit 46 and/or cassette 58.

In an exemplary embodiment of the invention, one or more power sources 50 provide power to one or more of; dose display meter 55, controller 52, motor 53 and/or circuitry 51 to power thermal element 64. In some embodiments of the invention, power source 50 is located on unit 46 and/or on cassette 58. Optionally power source 50 comprises one or more batteries, for example, off the shelf available AAA or AA batteries. Optionally, power source 50 is rechargeable, for example, Li-ion, LiFePo4, LiCo, LiPo. In a non-limiting example, a AA, 3.7V, 2400 mAh lithium ion battery is used. In some embodiments, power source 50 is manual, for example, a spring. Optionally, applied power ranges, for example, from about 1 W to about 40 W, or 5 W-35 W, or 10 W-20 W, or other smaller, intermediate or larger ranges are used.

One example of a possible embodiment is described with reference to FIGS. 10A-D, in which the base and cassette are organized into a single unit, for example, not designed to be separated by the user. In another example, base 46 and cassette 58 are assembled into functional device 1000 by linking one or more element, for example, as described with reference to the section "ASSEMBLE DEVICE".

Patient Use

In an exemplary embodiment of the invention, the patient assembles inhaler base unit 46 and cassette 58 to interconnected form 1000 ready for use. Optionally, with one or more drug administrations, data is collected about the administration, non-limiting examples of collected data include; inhaler base unit ID 97, cassette ID 100, time of administration, duration of administration and/or any other suitable data that the treatment process may benefit from. Optionally, data is stored on base unit 46. Alternatively or additionally, data is stored on cassette 58.

FIG. 1B is a method of operating a device for delivering a vaporized organic substance, in accordance with an exemplary embodiment of the invention. Optionally, the method and/or device allow for frequent changes in the dose regiment, for example, titration of the dose, delivery at different times and/or of different amounts. Optionally or additionally, the method and/or device allow for multiple and/or intermittent doses to be delivered for prolonged periods. It should be noted that the method described in the flowchart is non-limiting. For example, some steps are optional. Furthermore, there can be other methods and/or other apparatus used to obtain the results.

Optionally, at 250, the device is assembled, for example, as will be described in the section "ASSEMBLE DEVICE".

Optionally, at 252, the device verifies one or more parameters before administering treatment, for example, as will be described in the section "VERIFY PARAMETERS".

Optionally, at 254, the device detects a condition which results in a signal to start delivering treatment, for example, as will be described in the section "EXEMPLARY START SIGNAL".

At 256, in an exemplary embodiment of the invention, the tape is selectively heated, for example, as will be described in the section "HEAT TAPE".

At 258, in an exemplary embodiment of the invention, the tape is selectively moved with respect to the heating element, for example, as will be described in the section "MOVE TAPE".

Optionally, at 260, the extraction of the substance from the tape is stopped, for example, as will be described in the section "STOP".

Optionally, at 262, the device records data related to the substance extraction and/or delivery, for example, as will be described in the section "LOG".

Optionally, at 264, the patient is provided with feedback related to the substance delivery, for example, as will be described in the section "FEEDBACK".

Optionally, at 266, the delivery of the substance is adjusted, for example, as will be described in the section "ADJUST".

Optionally, one or more of 252, 254, 256, 258, 260, 262, 264, 266 are repeated.

Assemble Device

In an exemplary embodiment of the invention, the patient connects cassette 58 unit to inhaler base unit 46. FIG. 4B illustrates combined inhaler 1000, in accordance with an exemplary embodiment of the invention.

In an exemplary embodiment of the invention, the interconnection of units 46 and 58 links, for example one or more of;

Heating electronics 51 (e.g., on base 46), to heating element 64 (e.g., on cassette 58). Optionally, the linking completes a heating circuit.

Air intake tract 49 (e.g., on base 46) to air transfer tract 59 (e.g., on cassette 58). Optionally, the linking completes an air intake flow tract, having one end for air entering the tract, a region for vapors, and a second end for inhaling the air and/or vapors.

Precision driving mechanics 54 (e.g., on base 46) to the precision tape transport mechanics 62 (e.g., on cassette 58). Optionally, the linking completes a mechanism for controlled movement of the tape.

Tracing transceiver module 56 (e.g., on base 46) with the tracing module 69 (e.g., on cassette 58). Optionally, the linking completes the identification circuitry for identification that the cassette has been inserted into the correct base.

A potential advantage of distributing the functional elements between base 46 and cassette 58 such that assembly is required for functionality is for example, to reduce and/or prevent inadvertent access to regulated substances stored in cassette 58. Another potential advantage is reduction in costs, for example, the patient may be given the inhaler for free and only required to pay for the cassettes. Another potential advantage is ease of patient use, for example, the patient plugs the cassette into the inhaler, uses the device, and removes the cassette for a refill.

Verify Parameters

In an exemplary embodiment of the invention, controller 52 controls the movement of tape 63 and/or activation of heat by element 64. Optionally, controller 52 reads data stored on an associated memory, for example, user prescriptions, user usage data. Alternatively, controller 52 downloads data directly from system 120, for example, through a wireless connection.

In an exemplary embodiment of the invention, data is stored on unit 46. Potentially, breach of confidentially of data is reduced and/or prevented by not storing data on cassette 58, which may be returned. Alternatively or additionally, data is located on cassette 58. Potentially, control over the use of restricted substances is improved, for example, by analyzing the data when cassette 58 is returned.

In an exemplary embodiment of the invention, one or more parameters are accessed and/or verified, for example, by controller 52. Optionally, controller 52 verifies that the data is up to date, for example, by checking the timestamp associated with the data. Optionally, controller 52 downloads the most up to data, for example, using a wireless connection.

In an exemplary embodiment of the invention, controller 52 verifies that cassette 58 is authorized to work with device 46. Optionally, controller 52 is disabled if tampering has been detected by sensor 70. For example, as described in the section "TAMPER".

In an exemplary embodiment of the invention, controller 52 controls movement of tape 63 and/or application of heat by element 64, for example, to extract the active substances. In an exemplary embodiment of the invention, the treatment is administered by controller 52 according to logic (e.g., a software module), for example using a table. In an exemplary embodiment of the invention, the table correlates the prescription information and/or the packaging details of tape 63 (e.g., density of active substance) with tape movement and/or heating parameters to achieve the desired drug extraction. Optionally, the table is stored on memory. Optionally, the table has been pre-programmed, for example, by a manufacturer. Alternatively or additionally, controller 308 operates according to mathematical models (e.g., equations).

In an exemplary embodiment of the invention, data is updated, for example, once an hour, once a day, once a week, once a month, before and/or after a treatment session, before and/or after an inhalation has been delivered, or at other smaller, longer or intermediate intervals.

Exemplary Start Signal

In an exemplary embodiment of the invention, the drug delivery process is initiated by detection of mouth piece 47 in the patient's mouth, for example, by a temperature sensor measuring a temperature in the range of 32-42 degrees Celsius, or other smaller, intermediate or larger ranges are used. Alternatively or additionally, the drug delivery process is initiated by the patient inhaling, for example, by inhalation air flow opening unilateral valve 48 placed in air intake tract 49 of inhaler base unit 46. For example, an airflow rate of at least 0.1 liters/second, or 0.2 L/sec, or 0.5 L/sec, or 0.8 L/sec, or 1 L/sec, or other smaller, intermediate or larger flow rates are used. Alternatively or additionally, the drug delivery process is initiated by predetermined time periods. For example, the device might turn on by itself for debilitated patients, or only be able to be turned on during predetermined periods such as; 9:00 AM-9:05 AM, 1:30 PM-1:40 PM, 8:45 PM-9:00 PM. For example, for abuse prevention.

In some embodiments of the invention, there is a button which turns on the device. Optionally, after the button is pressed, one or more of the above act as triggers.

Heat Tape

In an exemplary embodiment of the invention, after determining that the user is authorized to receive the drug, controller signals heating element 64 inside cassette 58 to start applying heat to tape 63. Optionally, the authorization is provided by the remote server (e.g., central database) by wireless signal. Alternatively or additionally, the authorization is provided by the controller checking usage and/or prescription data. Optionally, control module 52 controls heating electronics 51 which heat element 64. For example, electronics 51 transmit current to element 64.

In an exemplary embodiment of the invention, element 64 transmits heat directly to the tape, for example, by contacting the tape directly, or by contacting one or more intermediate materials in contact with the tape. Alternatively, element 64 transmits heat by heating air, the air is then directed to contact the material, for example, the air is drawn by the inspiration of the patient. Alternatively, element 64 transmits heat by radiation, for example, by a laser and/or IR diode.

In an exemplary embodiment of the invention, element 64 is heated to a temperature of about 215 degrees Celsius, or about 200 degrees Celsius, about 250 degrees, about 230 degrees, about 180 degrees, about 160 degrees Celsius, or other smaller, intermediate or larger temperatures are used. Optionally, element 64 is heated to a stable vaporizing temperature.

In an exemplary embodiment of the invention, element 64 is heated cause the tape material to reach the selected temperature in no more than 500 milliseconds, or 100 msec, 250 msec, 400 msec, 700 msec, 1000 msec, or other smaller, intermediate or larger time frames are used. Optionally, the tape material is heated to a temperature that is sufficiently high to release the active substances. Optionally or additionally, the tape is heated to a temperature that is sufficiently low to prevent and/or reduce of unwanted substances.

In an exemplary embodiment of the invention, to provide a dose, several hundred milligrams of the organic material are heated in order to provide several milligrams of the active substance to the patient. For example, standard doses of medical *Cannabis* complexes range from about 4.90 mg (about 2.7 mg THC, about 2.5 mg CBD) and upwards to about 20 mg, administered up to several times a day. Optionally, the amount of tape provided is sufficient for at least a daily, a weekly, or a monthly dose regiment, or other smaller, intermediate or larger times frames are used.

In a non-limiting example, a tape having dimensions of about 30 mm wide by about 0.5 mm high by about 4000 mm long contains about 20 grams of source material. The source material contains various concentrations of active substances depending on the strain (e.g., 300 mg THC). In some embodiments, the delivery device is capable of vaporizing a minimal dose of about 10 mg of source material at a time, or about 5 mg, about 2 mg, about 15 mg, about 20 mg, or other smaller, intermediate or larger values are used. Optionally, the 10 mg of source material contains about 2 mg of THC. In some embodiments, the 20 grams of source material is sufficient for about 1 month according to some dosing profiles.

In an exemplary embodiment of the invention, the synchronized operation of selectively applying localized heat to the tape and/or moving the tape relative to the heat source yields a precise vaporized dose of the drug, for example, for immediate inhalation. Inventors hypothesize that the precision of the dose is limited by the make-up of the naturally derived organic matter, as the raw material is processed in a limited manner to prevent or reduce damage to the active substance, control over the amount of active substance is limited by the process. Precision of the dose vaporized is, for example, about +/−5%, about +/−10%, about +/−20%, about +/−25%, about +/−33%, about +/−50%, or other smaller, intermediate or larger values are used.

In an exemplary embodiment of the invention, the dose control is achieved by measuring the batch of matter in the tape (e.g., dose per unit area) and marking the cartridge with the information (e.g., RFID, QR code). In an exemplary embodiment of the invention, the speed of the tape and/or heating of the element are programmed according to the provided tape measurements (e.g., measurements read from the cassette).

In some embodiments, the heating element in conjunction with the control module may inscribe an identifier, for example, via alternating temperature fluctuations, on the tape itself in predetermined locations. The transcription may involve any sort of unique identifier verifying the use of the tape in this specific inhaler base unit, potentially, further complicating any illegal trafficking, for example, by the ability to link the tape with the assigned user.

In an exemplary embodiment of the invention, formed vapors enter vapor chamber 60. Optionally, the inhalation force generated by the patient brings in air (e.g., room air shown as arrows) through air intake tract 61, into vapor chamber 60, where the air mixes in with vapors 80 (shown as smoke). Optionally, vapors 98 mixed with the room air travel up air transfer tract 59, optionally assisted by a thermal draft (rising hot air), reaching mouthpiece 47 and enter the mouth of the patient.

Move Tape

FIG. 5A is a schematic depicting the movement of a source material 303 (e.g., a component of tape 63) relative to a thermal emitter 301 (e.g., heating element 64), in accordance with an exemplary embodiment of the invention. Optional forward movement of source material 303 is illustrated by arrows 703. In some embodiments, reverse motion is possible. For clarity, a section of an optional semi-permeable layer 702 overlayed on source material 303 (e.g., together forming an embodiment of tape 63) is shown as being virtually removed (details of the permeable layer will be described below, for example, in the section "TAPE").

In an exemplary embodiment of the invention, a volume of source material 700 is heated by the thermal emitter, forming vapor 502. A residual source material 701 (e.g., after heating) comprised of the remnant fibrous material is shown as having been moved away from the thermal element, for example, spooled into a roll.

FIG. 5B is a blown up picture showing tape 63 moving across element 64 (e.g., as in FIGS. 4A-4B), in accordance with the movement as shown in FIG. 5A. Tape 63 moves forward or reverse relative to element 64 (arrows 140 show forward motion). Area 142 of tape 63 contacting element 64 is heated. Optionally, vapors 80 enter vapor chamber 60, optionally mixing with room air (shown as arrows 144).

Referring back to FIGS. 4A-4B, in an exemplary embodiment of the invention, tape 63 is moved over heating element 64 in a controlled manner, for example, controlled by control module 52. Optionally, the plant complex in dose tape 63 is vaporized to produce the predetermined dose.

In an exemplary embodiment of the invention, control module 52 controls the application of power to motor 53. Optionally, motor 53 powers precision drive mechanism 54. Optionally or additionally, mechanism 54 drives precision tape transport mechanics 62 (e.g., comprised of pinch rollers and gears). Optionally or additionally, mechanism 62 pulls tape 63 at a predetermined rate. Optionally, tape 63 is pulled from supply reel 65 (e.g., pressed against drag elements (not shown) to maintain the tension of dose tape 63), across element 64, and into intake reel 68. Optionally, reel 68 is driven by a transport slip belt 67, potentially ensuring proper recovery of vaporized dose tape 63 on intake reel 68, for example, maintaining the tension of tape 63.

In an exemplary embodiment of the invention, the remains of the vaporized organic matter are moved away from the heating element. Optionally, the remains are kept in a waste chamber inside the cassette. Optionally, the localized heating is sufficient to substantially vaporize the organic matter, for example, at least 30% is vaporized, or 50%, or 70%, or 90%, or other smaller, intermediate or larger values. Optionally, the remaining residue of the source-material contains no significant amount of remaining drug. A potential advantage of preserving the post consumed drug inside the intake chamber, is that the authorities will have access to the post administered material for inspection purposes.

Stop

In an exemplary embodiment of the invention, delivery is stopped after the predetermined dose has been released. Optionally, the predetermined dose corresponds to the length of tape spooled and/or heated, for example, the delivery is stopped for the current treatment. Alternatively or additionally, delivery is stopped by detecting a slowdown (e.g., stop is temporary) in the inhalation flow rate (e.g., as sensed by flow sensor coupled to valve 48), for example, less than 0.1 liter/second, or less than 0.2 L/sec, 0.5 L/sec, 0.8 L/sec, 1 L/sec, or other smaller, intermediate or larger flow rates are used. Alternatively, the tape speed is adjusted to match the change in inhalation rate. Alternatively or additionally, drug delivery is stopped by detecting a drop in temperature, for example in mouthpiece 47, for example, to below 37 degrees Celsius, or below 35, 33, 31, 29, 27, 25, or other smaller, intermediate or larger values are used. Alternatively or additionally, drug delivery is stopped after detecting that the required dose has been delivered, optionally within a predetermined time period. For example, a dose of 1 gram has been delivered during the time period of 7 AM to 1 PM.

In some embodiments, the patient can take a break from inhaling, for example, a temporary stop. Optionally, the device starts and stops according to the patient inhalation pattern. Alternatively or additionally, the device continues to function for at least a predetermined amount of time, generating vapors that are temporarily stored in a vapor storage area. The device can continue to function (e.g., let the patient break) for no more than 10 seconds, or 20 seconds, or 30 seconds, or 60 seconds, or other smaller, intermediate or larger time frames are used.

In an exemplary embodiment of the invention, once a user ceases inhalation, control module 52 stops the pulling of dose tape 63, and/or disengage heating element 64.

Log

In an exemplary embodiment of the invention, one or more parameters related to the dosing process are logged, for example, in a memory coupled to control module 52 and/or in database 119. Non-limiting examples of the parameters include; start time of administration, end time of administration, dosing profile during the administration (e.g., dosing rate), total administered dose, unique identifier of inhalation base unit 46.

In an exemplary embodiment of the invention, the parameters are stored in association with the unique identifier of the cassette, for example, read from a memory coupled to a tracing module 69. Optionally, the unique identifier of the cassette is acquired by inhaler base unit 46 through a tracing transceiver module 56, for example, wirelessly by reading an RFID, NFC, Bluetooth chip, and/or by a physical connection between transceiver module 56 and tracing module 69, and/or by an external optical machine readable identifier, for example, Barcode, QR code.

User Feedback

In an exemplary embodiment of the invention, dose display meter 55 (e.g., positioned on the outside of inhaler base unit 46) indicates the dose administration status, for example, an output of the progress of the treatment dose completing for the user. Optionally, the output is visual, for example, displaying the percentage of the dose delivered or remaining, for example, as a number or as parallel lines. Alternatively or additionally, the output is audible, for example, tunes, beeps and/or spoken language. Optionally, control module 52 controls the output.

In an exemplary embodiment of the invention, dose display meter 55 indicates visually and/or audibly that the dosing is complete.

In an exemplary embodiment of the invention, dose display meter 55 indicates that the content of cassette 58 unit is nearly or entirely consumed, for example, by flashing lights and/or by a distinct long beep.

Adjust

In an exemplary embodiment of the invention the user resumes inhalation, for example, if the dose cannot be obtained in a single inhalation. Optionally, the vaporization process is resumed. Alternatively, the vaporization process is not shut down, for example, vapors are held within vaporization chamber 60, optionally prevented from leaving by valve 48 until inhaled by the patient. Potentially, the method provides for intermittent administration of the dose.

In some embodiments of the invention, the inhalation velocity (e.g., generated by the patient) is detected, for example, by unilateral valve 48 and/or by a flow rate sensor. In some embodiments of the invention, the inhalation velocity is used to adjust the heating process. Optionally, an increase in inhalation velocity is used to trigger an increase in the current to the heating element, for example, to offset the additional cooling generated by the faster flowing air. Optionally, an increase in inhalation velocity is used to trigger an increase in the rate at which the tape flows over the heating element, for example, to deliver a relatively larger dose and/or at a relatively faster rate. Alternatively, the temperature of the element is maintained by measuring the temperature of the element directly, for example, by a temperature sensor. Optionally, control module 52 controls the adjustments based on the inhalation rate.

In some embodiments of the invention, the rate of drug delivery remains constant regardless of the inhalation flow rate. Optionally, the inhalation flow rate is controlled, for example, by a valve in the nozzle that does not allow faster flow rates. Alternatively or additionally, the flow rate through vapor chamber 60 is maintained, for example, by a valve that opens to allow an increase in flow rate to be accommodated through a secondary air flow that does not flow through chamber 60.

In some embodiments of the invention, the heating and/or tape movement is adjusted in accordance with the characteristics of the packed organic matter in the tape of the cassette, for example, each strain with its unique physical properties may require a different dosing profile. Optionally, control module 52 stores specific dosage profiles according to specific cassette 58 attached, in order to 'translate' the prescribed dose according to the characteristics of the packed organic matter. For example, to deliver 10 mg of active compounds, 10 cm of tape may be required for a first type of cassette, whereas in a cassette containing organic matter with higher concentration of active compounds, only 5 cm of tape may be required.

In some embodiments of the invention, the user adjusts the device. Optionally, the user adjusts the rate of vaporization (e.g., upwards or downwards), for example, to accommodate the ability of the user to inhale the produced vapors. Alternatively or additionally, the user adjusts the pattern of vaporization, for example, continuous or in steps separated by stop times. The user can adjust the device manually (e.g., by buttons and/or dials) and/or through software (e.g., control module on a web site).

Exemplary Tape Embodiments

In an exemplary embodiment of the invention, the organic source material is packaged into a predetermined (e.g., estimated) layer of tape (e.g., strip or sheet). Optionally, the material is packaged in a homogenous layer, for example, a first area or volume has substantially the same density (e.g., of active drug) as a second area or volume. Optionally, the difference in density of active drugs between any two volumes of packed organic material on the tape differs by no more than 1%, or no more than 5%, or 10%, or 15%, or 20%, or 25%, or 33%, or other smaller, intermediate or larger values are used.

In an exemplary embodiment of the invention, cassette 58 is vacuum sealed in sterile packaging. Optionally, cassette 58 is registered in the database, for example to allow tracking, for example, to a specific pharmacy.

In an exemplary embodiment of the invention, the source material is packaged in a continuous manner. Alternatively, the material is packaged into specific dose sections, for example, having a non-vaporisable material and/or space separating the sections.

In an exemplary embodiment of the invention, cassette 58 is labeled describing the standardized and/or homogenous packing information, for example, of structurally processed medical grade *Cannabis* plants. For example, the stain type, the strain chemical composition (e.g., 20% THC, 5% CBD), the expiration date when sealed, the expiration date when opened. Optionally, the label information is provided in identifier 69, for example, a circuit and/or RFID. Alternatively or additionally, the label information associated with cassette 58 is entered into the database, for example, by the drug producers, for example, via the drug domain.

Optionally, the tape is processed for immediate and/or frequently recurrent administration. Optionally, the processing preserves the entire complex properties of the plant until heating for delivery.

In an exemplary embodiment of the invention, the tape is packed in a spooled arrangement, for example, in a diameter of about 30 mm, about 40 mm, about 50 mm, about 60 mm, about 70 mm, or other smaller, intermediate or larger measurement are used. Optionally, the tape is spooled as necessary to vaporize and deliver selected portions.

In an exemplary embodiment of the invention, the tape is sufficiently resilient for tight packing, unrolling, passing across the heating element, and/or re-rolling. For example, one or more material layers (e.g., as described with reference to FIGS. 6A-6F) provide the resiliency. Optionally, spooling the tape (e.g., comprising the material layers) does not crumple the layers of the tape and/or separate the layers. Potentially, the packed design prevents and/or reduces various faults throughout the system operation, for example, inaccurate dosing, and/or complete jamming of the system.

In an exemplary embodiment of the invention, the edges of the tape are sealed, for example, using thixtropic adhesive sealant (e.g., FDA compliant, high temperature silicone). Alternatively, the tape's edges are left unsealed, for example, allowing the encapsulating walls of the host enclosure system, and/or the tension maintained by the pooling mechanism to keep the tape's stacked layer structure intact.

Some non-limiting examples affecting the selection of one or more materials of the tape include; biocompatibility requirements, tensile strength requirements, flexibility requirements, chemical interaction requirements with the source-material and its resulting output, operational temperature requirements, heat dissipation requirements, friction coefficient requirements and/or an adhesion process which is not harmful to the source-material.

In some embodiments of the invention, the dose tape contains buffer sections comprised of a cleaning material between each sectioned dose. Optionally, the cleaning material cleanses the heating element, for example, after each dose. For example, the cleaning material absorbs any residue adhering to the heating element. Potentially the cleaning prevents degradation of the heating process and/or maintains accurate vaporization units.

In a non-limiting example, 10 grams of medical grade dried *Cannabis* is packaged into a tape about 29.5 mm wide×about 2000 mm long×about 0.6 mm thick. The tape is rolled onto a 10 mm diameter core, resulting in an overall roll diameter of about 40 mm.

In an exemplary embodiment of the invention, the tape is organized with a predetermined amount of active substance per unit of volume and/or surface area. For example, the tape is organized in units. Optionally, the units are the smallest clinically useful doses that would be administered to a patient. Alternatively or additionally, the units represent the resolution of the device in administering doses, for example, the device being unable to regulate doses below the units. Optionally or additionally, the units are separated by spaces which do not release drugs when heated, for example, empty spaces and/or inert materials.

In an exemplary embodiment of the invention, the tape is substantially uniform throughout. Alternatively, the tape is non-uniform, for example increasing in thickness and/or density of active substance from one end to another, for example, to allow titration of doses up or down.

In an exemplary embodiment of the invention, the tape contains a sufficient amount of raw material for a plurality of doses. In an exemplary embodiment of the invention, the tape contains, for example, at least 1 gram of raw materials, or at least 5 grams, 10 grams, 15 grams, 20 grams, 50 grams, 100 grams, or other smaller, intermediate or larger amounts are used.

In an exemplary embodiment of the invention, the dried vegetable matter is compressed, leaving enough air spaces to allow for vapors to escape. For example, the density is about 10% matter, or about 20%, about 30%, about 40%, about 50%, or other smaller, intermediate or larger values are used.

Figure 6A:
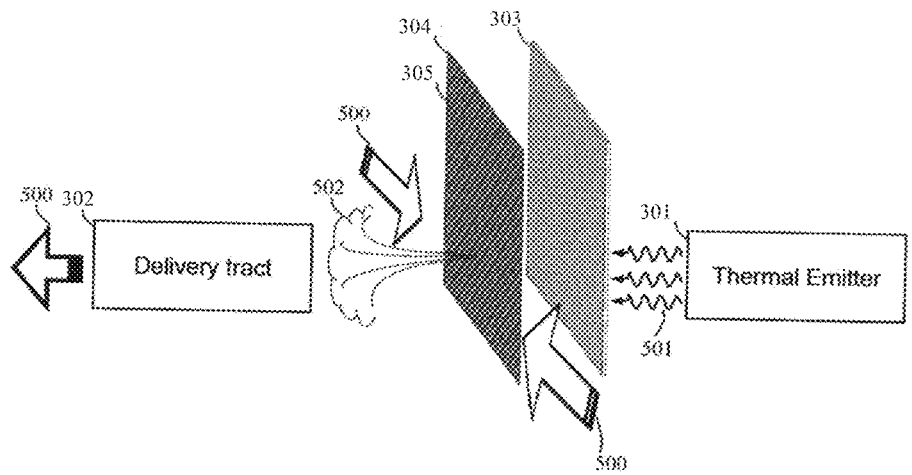
FIGS. 6A-6F are schematics of some embodiments of the tape, in accordance with an exemplary embodiment of the invention.

FIG. 6A illustrates an embodiment of a segment of tape, in accordance with some embodiments of the invention. The tape segment is shown in a state ready for delivery of drugs, being positioned between thermal emitter 301 and delivery tract 302. In an exemplary embodiment of the invention, the tape comprises packed source material 303, for example, packed *Cannabis* in organic matter form.

In an exemplary embodiment of the invention, the tape is mechanically coupled to an optional semi-permeable layer 304, for example, by frictional forces from tight packing and/or by sealing of the edges. In an exemplary embodiment of the invention, permeable layer 304 is positioned between source-material layer 303 and delivery tract 302 (e.g., outflow tube, from which the patient inhales). Permeable layer 304 comprises a plurality of apertures, the apertures are sufficiently small to contain material 303 (before vaporizing and after vaporizing) and the apertures are sufficiently large to allow the vaporized substance to escape to delivery tract 302.

In a non-limiting example, layer 304 is a mesh, for example, made from stainless steel. In the case of *Cannabis*, the hole sizes range from about 25 µm (e.g., below which only vapors can pass through) to about 500 µm for example, about 40 µm (e.g., size of cannabinoid containing trichomes), about 50 µm, about 55 µm, about 60 µm, about 100 µm, about 150 µm, about 200 µm, about 250 µm, about 300 µm, about 400 µm, about 500 µm, or other smaller, intermediate or larger sizes are used. In some embodiments, the hole size is selected to be smaller than the smallest plant particle containing active substances, for example, the size of cannabinoid containing trichomes.

In an exemplary embodiment of the invention, the thickness of layer 304 is about 0.005 mm, about 0.01 mm, about 0.03 mm, about 0.05 mm, or about 0.06 mm, about 0.08 mm, about 0.1 mm, about 0.5 mm, about 1 mm, or other smaller, intermediate or larger sizes are used.

In an exemplary embodiment of the invention, outer edges 305 of semi-permeable layer 304 are adapted to prevent or reduce excessive friction with the device walls (e.g., while tape is being spooled). For example, edges 305 are smooth, and/or do not contain partial aperture circumferences.

In an exemplary embodiment of the invention, the edge comprising the source material and one or more material layers are sealed together. In a non-limiting example, the sealant is an FDA compliant high temperature thixtropic adhesive silicone sealant. Potentially, sealing assists in maintaining the tight configuration of the tape.

In an exemplary embodiment of the invention, an area of source-material layer 303 contacts thermal emitter 301. Heat 501 is directly transferred to source-material layer 303 (e.g., radiation, conduction). Potentially, the transfer of energy by contact is relatively higher in energy efficiency. Alternatively or additionally, at least some heat is transferred to source material layer 303 without directly contacting layer 303, for example, by heating air, the hot air then transfers heat to layer 303 (e.g., convection). Alternatively or additionally, at least some heat is transferred to source material layer 303 by radiation, for example, by a laser with specific spectrum properties for efficiently vaporizing the specific source material 303.

In an exemplary embodiment of the invention, vaporized substance 502 (e.g., containing the active substance to be inhaled) from source-material layer 303 escapes through the pores of semi permeable layer 304 into delivery tract 302 and from there to the desired target, for example, the patient's respiratory system.

In some embodiments of the invention, the next time the tape is heated, partially heated areas are skipped.

In an exemplary embodiment of the invention, air 500 (shown as arrows) flows in front of semi-permeable layer 304, for example, brought in by tubes. Vapors 502 (e.g., containing the active substance to be inhaled) become mixed in with air 500 and travel to delivery tract 302. Alternatively or additionally, at least some air flows from behind layer 303 and through layer 304, for example, brought in by tubes to a location behind layer 303.

A potential advantage of the tight tape configuration, for example, the packed ground raw material sealed to the semi-permeable layer, is reducing and/or preventing trafficking of regulated substances such as *Cannabis*. For example, by tracking the amount of tape that has been vaporized in accordance with the allowed dose.

FIG. 7A illustrates a spooling mechanism 72 (seen as close up in a box 73) for maintaining the tight configuration of the tape (e.g., plant material and one or more layers), for example tape as described with reference to FIG. 6A, in accordance with some embodiments of the invention.

In some embodiments of the invention, a packed source-material tape 74 is loaded in spooling mechanism 72. A biasing element, such as a spring 79 is optionally attached to a vertically movable intake reel 81, and/or an optional vertically movable supply reel 82. Rolled packed source-material tape 74 by force of spring 79 is pressed against an internal wall 76. Semi permeable layer 75 of packed source-material tape 74 is pulled, transporting a tape 74 to contact a thermal emitter 78. Optionally pulling and/or spooled are performed by intake reel 81.

Some potential advantages of the described tape spooling embodiment include; tightly packed organic material that is entirely contained within the tape before and after vaporizing, a dynamic supply and intake reel sizes allowing for a compact design, and/or a constant angle of entry of the packed source material tape into the channel leading to thermal emitter 78. Another potential advantage includes preventing messy residue from vaporized material by tightly packing the material after vaporizing.

FIG. 6B illustrates the tape of FIG. 6A, further comprising a second layer 307, in accordance with some embodiments of the invention. In some embodiments, second layer 307 is coupled (e.g., mechanically by friction and/or adhesive) to a surface of source material 303, opposite that of semi-permeable layer 304. In some embodiments of the invention, the outer layers 307 and 304 form a sandwich around source material 303, containing material 303 before and after vaporizing.

In some embodiments of the invention, layer 307 prevents excessive distribution of heat from thermal emitter 301, for example, heat is transferred laterally to source layer 303, instead of dissipating across layer 307 and then to other unwanted parts of source layer 303. Non-limiting examples of materials include Kapton (made by Dupont).

In some embodiments of the invention, layer 307 does not contain apertures.

In some embodiments of the invention layer 307 scours the heater. Optionally, tape is intentionally advanced when the heater is turned off to obtain the scouring effect.

A potential advantage of the described tape embodiment is the prevention of vaporized residue on the heating element, (e.g., layer 307 prevents or reduces direct contact between material 303 and thermal emitter 301). Another potential advantage is the containment of the source material in the tape at all times.

FIG. 6C illustrates the tape of FIG. 6A, further comprising a third layer 12, in accordance with some embodiments of the invention. In some embodiments, layer 12 is coupled to a surface of source material 303 opposite that of semi-permeable layer 304. Material 303 is sandwiched between layers 312 and 304.

In some embodiments of the invention, layer 312 serves to maintain the packed state of the 'sandwich', for example, to stabilize the structure of the tape. Optionally, layer 312 maintains the desiccated state of the organic material. Non-limiting examples of the material of layer 312 include; plastic wrap.

In some embodiments of the invention, layer 312 is removed prior to heating. FIG. 7B illustrates a mechanism 600 for automatic removal of layer 312, for example, for use with the tape embodiments of FIG. 6C. The enlarged section is a detailed view of spooling mechanism 601.

In some embodiments of the invention, a tape 603 is organized as a roll 604, and dispensed by spooling. In some embodiments of the invention, layer 312 is separated from tape 603 prior to heating by thermal emitter 301. Optionally, layer 312 is separately spooled from tape 603, for example, by a separate spooling mechanism 605 into a separate spooling chamber. A tape 602 (with layer 312 removed) having the organic layer exposed continues to travel to contact thermal emitter 301. Optionally, remaining tape 602 is separately spooled by spooling mechanism 606.

FIG. 6D illustrates the tape embodiment of FIG. 6B, wherein layer 307 contains at least some apertures having a size sufficiently small to prevent material 303 from escaping, but a size sufficiently large to allow air to enter through layer 304 into source material 303.

FIG. 6E illustrates a tape embodiment in which the heating elements are an integral part of the tape. In some embodiments of the invention, the tape comprises source material layer 303, and at least one electrically resistive layer 25A coupled to at least one side of layer 303. Optionally, two layers 25A-B are coupled, one to each side of layer 303.

In some embodiments of the invention, at least one of layers 25A-B is made out of an electrically resistive material. Heat 501 is emitted by an area of layer 25A-B when contact is made with electrodes 26A-B.

In some embodiments of the invention, at least one layer 25A-B is semi-permeable, having apertures to allow vapor 502 to escape. Optionally, both layers 25A-B comprise apertures, allowing vapor 502 to escape from both sides of material 303. Optionally, both vapors 502 are directed towards delivery tract 302, for example, by an additional tube extending from layer 25B.

In some embodiments of the invention, one or more layers 25A-B stabilize and/or contain material 303, for example, by acting as a sandwich.

Figure 6B:
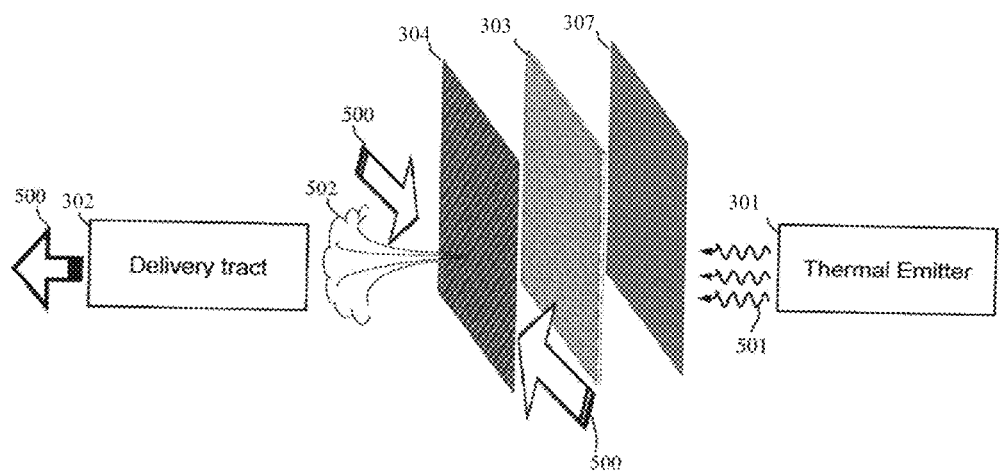
Figure 6C:
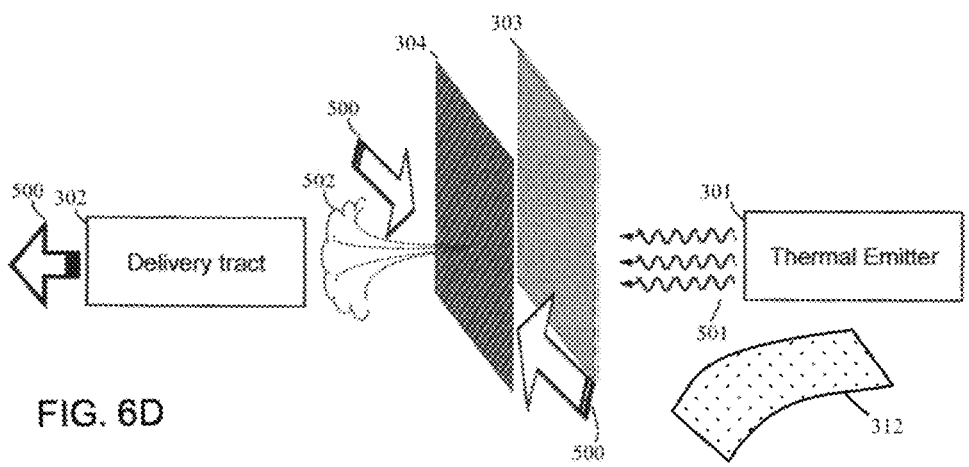
Figure 6D:
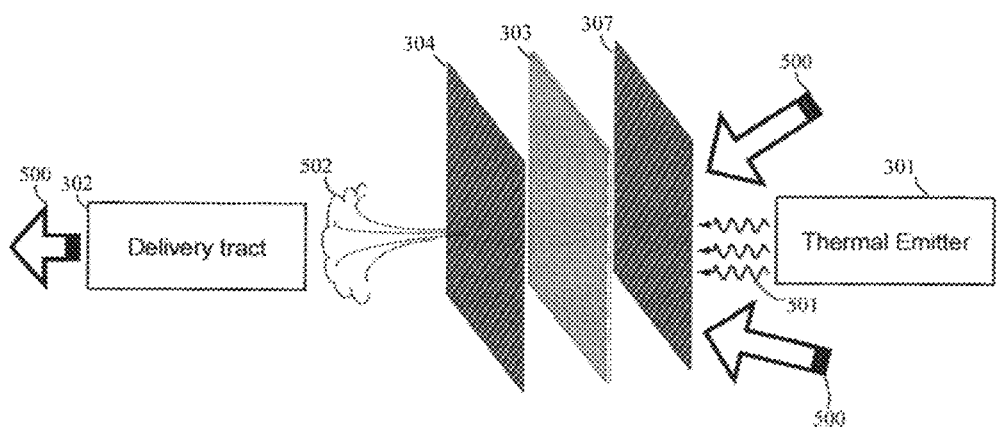
Figure 6E:
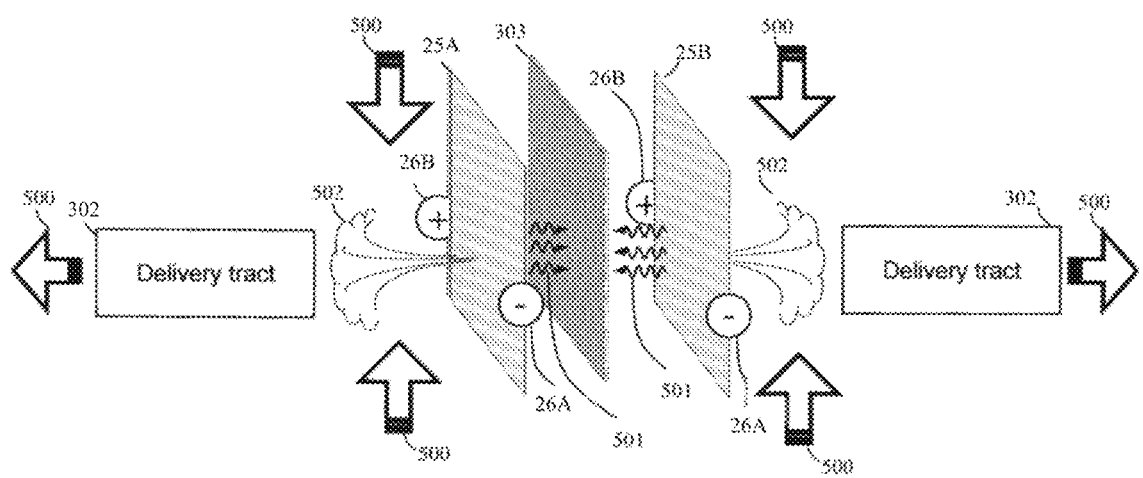
Figure 6F:
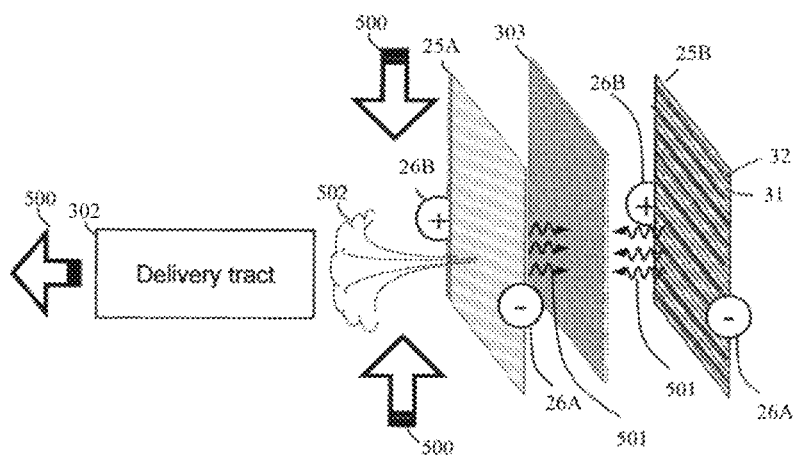

FIG. 6F illustrates the tape of FIG. 6E, in which some areas 32 of layers 25A-B are resistive acting as thermal emitters, and some areas 31 are insulators, in accordance with some embodiments of the invention. Optionally, areas 32 and/or 31 comprise apertures.

In some embodiments, resistive areas 32 are formed over an insulating material 31, non-limiting examples include; printing, adhesion, coating.

In some embodiments, resistive areas 32 alternate with insulating areas 31, for example, are lined up in parallel.

Potentially, insulating areas 31 prevent heat from dissipating from resistive areas 32, allowing the generated heat to be directed towards source material 3. Potentially, vaporization is relatively more precise and/or relatively more energy efficient.

In some embodiments of the invention, the tape is formed into different shapes. Optionally, the tape is cut into sections. Optionally the sections contained a measured amount of active substance.

Figure 8:
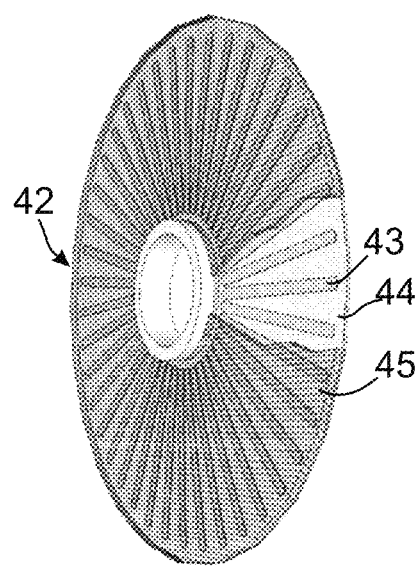
FIG. 8 is a disc shaped design of the tape, in accordance with an exemplary embodiment of the invention.

FIG. 8 illustrates a disc shaped design of a packed source-material 42 version of the tape, in accordance with some embodiments of the invention. A source-material layer 44 is optionally positioned behind a semi-permeable layer 45.

In some embodiments, material 44 is sectioned into specific dose slots, optionally separated by one or more inert barriers 43 (seen as visible through a virtual cut out of the figure). Alternatively, material 44 is continuous, without barriers 43.

A potential advantage of the disc tape embodiment is allowing for a 'no moving parts' device, for example, by positioning the tape around a central delivery tract, for example, as will be described with reference to the section "ADDITIONAL DEVICE EMBODIMENT".

Exemplary Device Embodiment with No Moving Parts

Figure 9A:
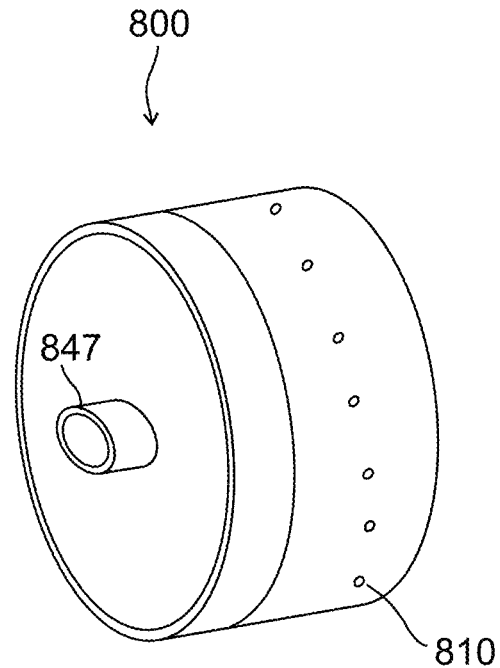
FIGS. 9A-9C are various views illustrating the delivery device having no moving parts, in accordance with some embodiments of the invention.
Figure 9B:
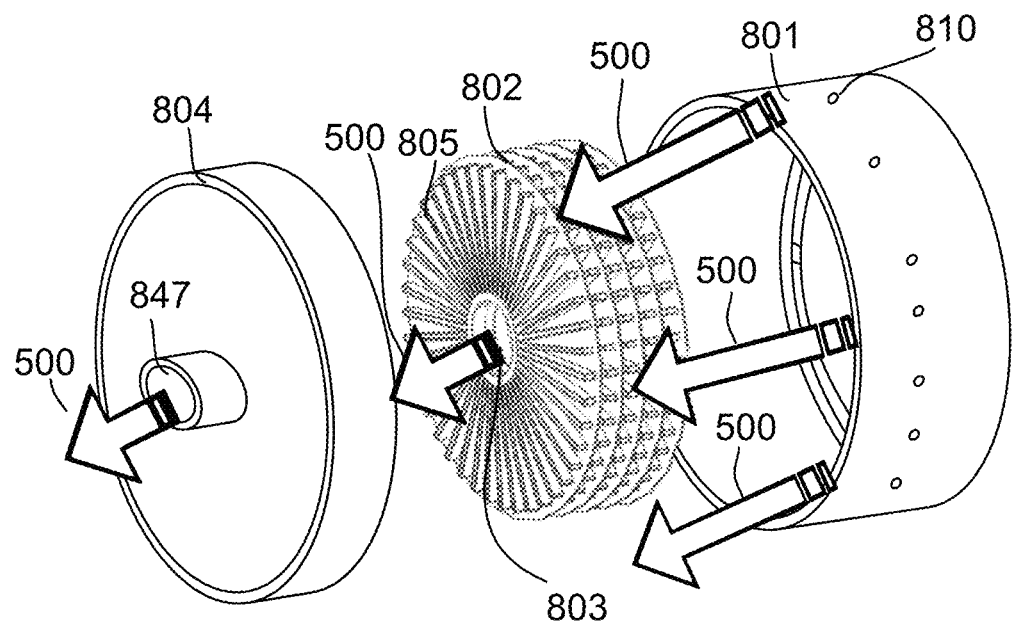
Figure 9C:
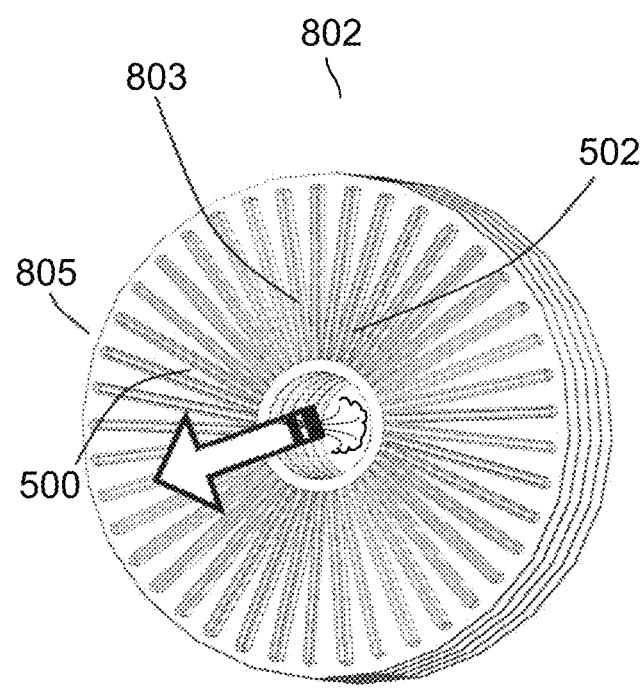

FIGS. 9A-9C illustrate an inhaler 800 designed to have a 'no moving parts' operation, in accordance with some embodiments of the invention. FIG. 9A is an isometric view of inhaler 800. FIG. 9B illustrates the internal components of FIG. 9A. FIG. 9C is a close up view of the discs used in inhaler 800.

In some embodiments of the invention, a stack 802 of one or more plates (e.g., discs, rectangles, other suitable shapes), for example, as shown in FIG. 8, are used. Optionally, discs are divided into individual doses 805, for example, by slots.

In some embodiments of the invention, doses 805 are administered individually, for example, each dose 805 is associated with a dedicated heating element. A controller selectively activates the heating elements to release doses 805.

In some embodiments of the invention, vapors 502 from heated doses 805 are channeled to a central delivery tract 803. Optionally, doses 805 and/or discs 802 are symmetrically arranged around tract 803. In some embodiments of the invention, inhalation through a mouthpiece 847 draws air 500 (shown as arrows) and vapor 502 to the patient. Optionally, air 500 is drawn in from one or more apertures 810 located around the perimeter of the storage chamber 801, passing to central delivery tract 803 through segmented dose slots 805. Air 500 collects vapor 502 and channels it to mouthpiece 847.

In some embodiments of the invention, a lid 804 of storage chamber 801 may hold the required electronics, necessary for activating this design. For example, one or more of: device ID chip, communication port, power source, electronics controlling emitters, controller, dose display meters.

In some embodiments of the invention, inhaler 800 comprises a desiccator to remove moisture from the inhalation. Optionally, inhaler 800 is located in mouthpiece 847.

In some embodiments of the invention, there can be a few moving parts, for example, to move stacks 802 of discs towards a heating element, for example, as described in the section below.

Exemplary Device Embodiment Formed as a Single Component

Figure 10A:
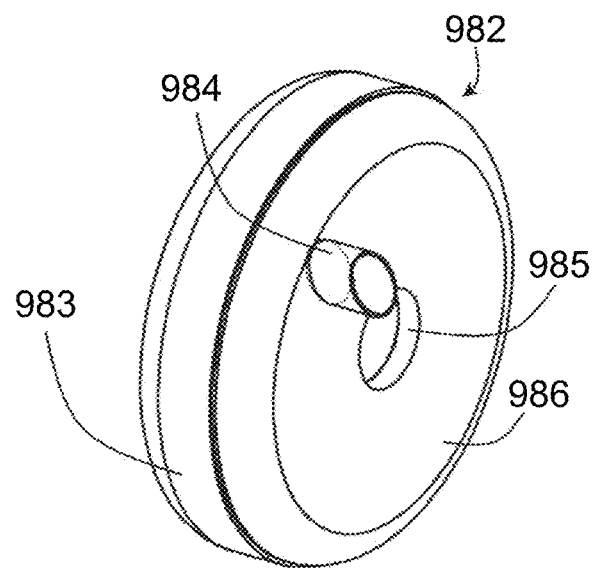
FIGS. 10A-10D are various views illustrating the delivery device using a disc shaped version of the tape, in accordance with some embodiments of the invention.
Figure 10B:
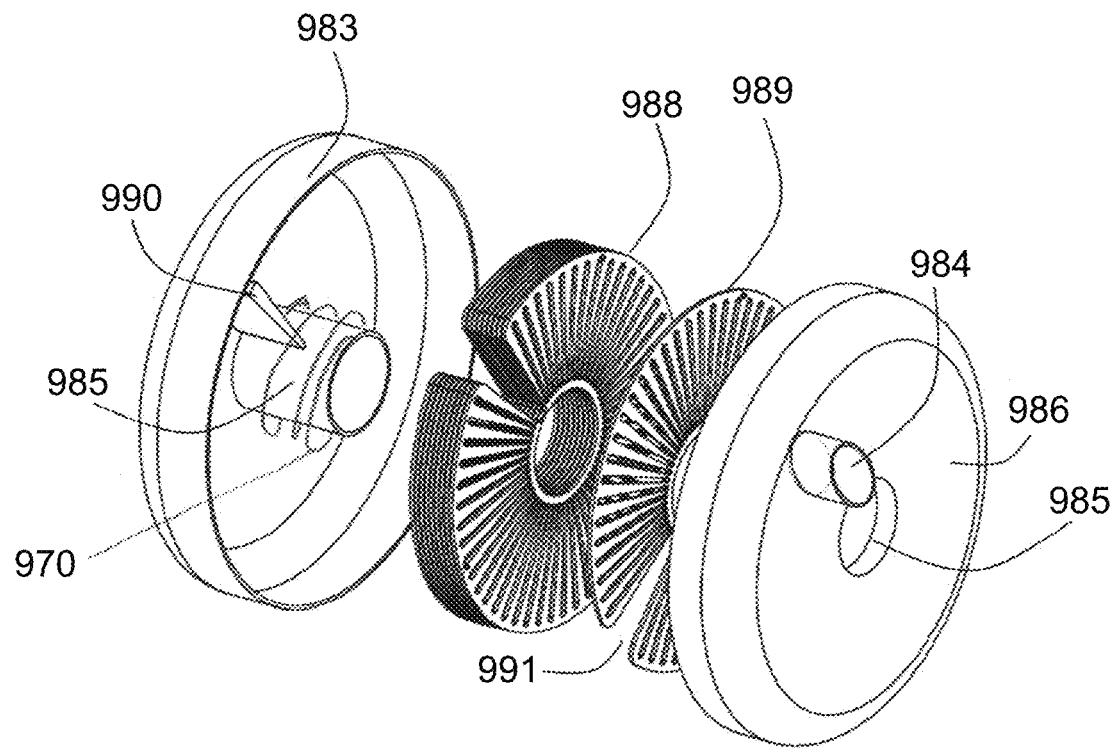
Figure 10C:
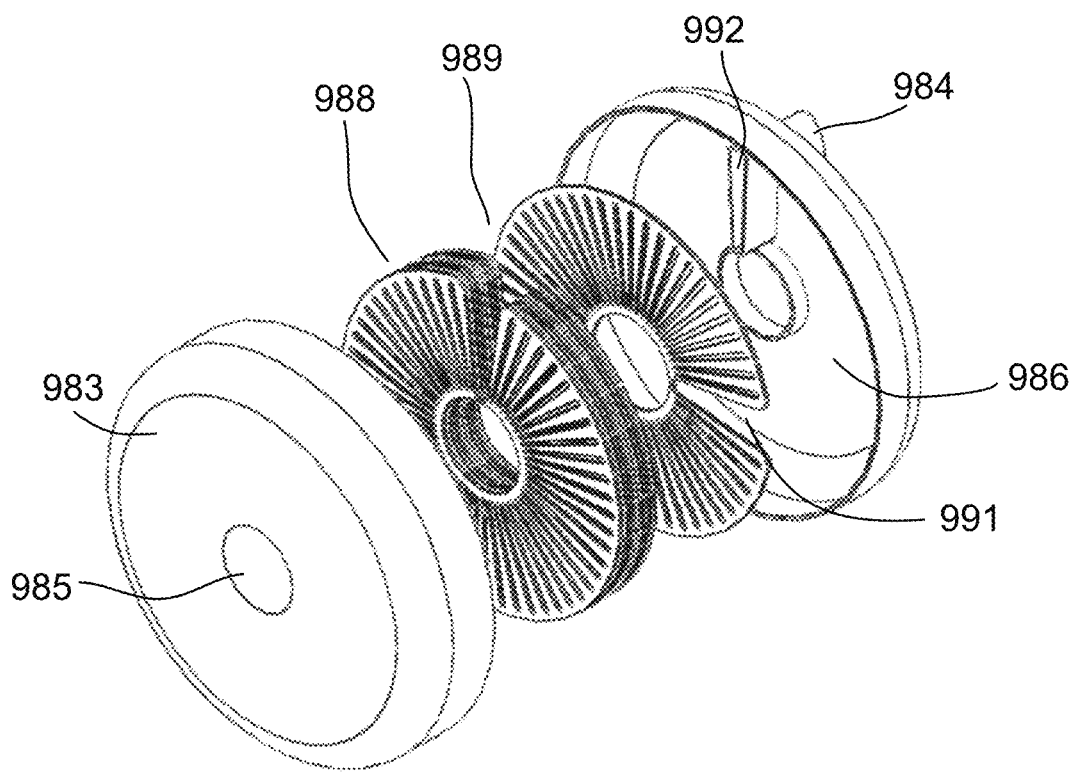
Figure 10D:
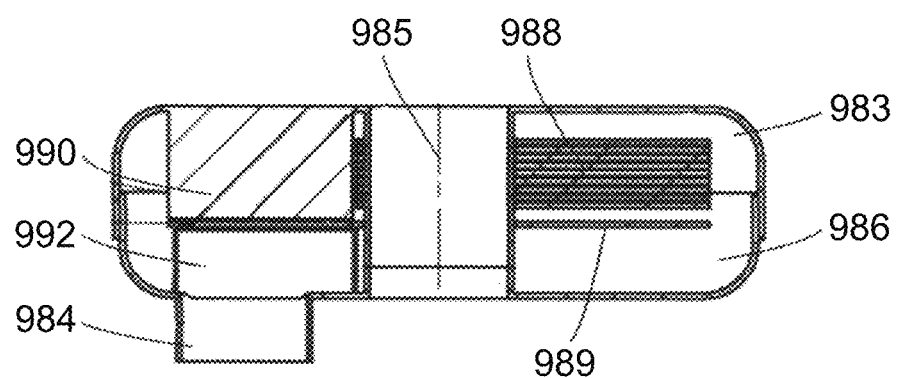

FIGS. 10A-10D illustrate a single component embodiment of an inhaler 982 (e.g., does not require assembly of nozzle and cassette), in accordance with some embodiments of the invention. Optionally, inhaler 982 uses one or more discs, for example, as described with reference to FIG. 8, in accordance with some embodiments of the invention. FIG. 10A is an isometric view of inhaler 982. FIGS. 10B and 10C illustrate different views of the components inside inhaler 982. FIG. 10D is a cross section through inhaler 982. Potentially, inhaler 982 provides improved security over the distribution of drugs, for example restricted substances, such as by reducing the ability to break open inhaler 982 to remove the drugs inside.

In some embodiments of the invention, a supply chamber 983 houses source material in one or more discs 988. A biasing element such as a spring 970 urges discs 988 in a direction, for example, towards a mouthpiece 984. An active disc 989 currently delivering drugs is rotated clockwise or anticlockwise, for example, by a motor automatically controlled by a controller. Rotation is continuous or discrete for example, to position a dose located on a dose slot against a thermal emitter 990. Emitter 990 heats a section of active disc 989 to release vapors. Vapors travel through an optional delivery tract 992 (optionally located opposite emitter 990) and through mouthpiece 984 to reach the patient. After the dose is administered, active single packed source-material disc 989 rotates further until all sequential doses are administered, for example, until an optional disc cut out 991 is reached. The used packed source-material disc 989 is transported into an intake chamber 986, and the next disc now becomes the active disc.

In some embodiments of the invention, all components necessary for function are housed in inhaler 982, for example, in a housing 985.

Potentially, inhaler 982 provides improved security over the distribution of drugs, for example restricted substances, such as by reducing the ability to break open inhaler 982 to remove the drugs inside. Potentially, security is improved over abuse and/or trafficking. For example, the patient may have a hard time opening the device to take additional drugs (e.g., abuse). For example, the patient may have a hard time opening the device to sell the material to others (e.g., trafficking.)

In some embodiments of the invention, the tape is a single component, for example, a tape made by mixing source material (e.g., plant material) with a suitable adhesive, for example, as described in the section "EXEMPLARY METHOD OF MANUFACTURING TAPE". The hardened solid mixture can be used in the inhaler, for example rolled, spooled and directly contacting the heating element, for example, as described herein.

Exemplary Drug Delivery Profiles

Figure 11A:
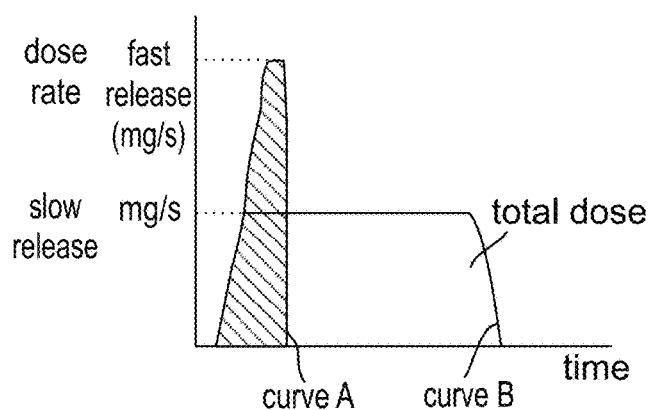
FIGS. 11A-11F are some non-limiting examples of substance extraction profiles, in accordance with an exemplary embodiment of the invention.
Figure 11B:
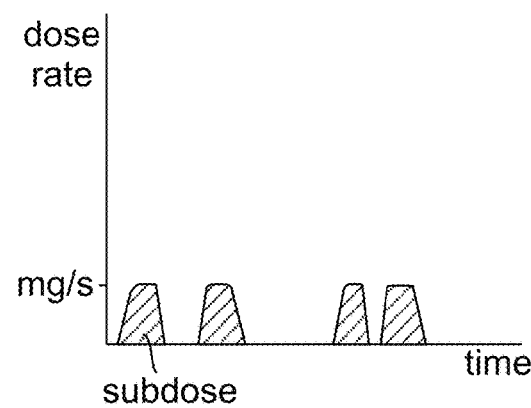
Figure 11C:
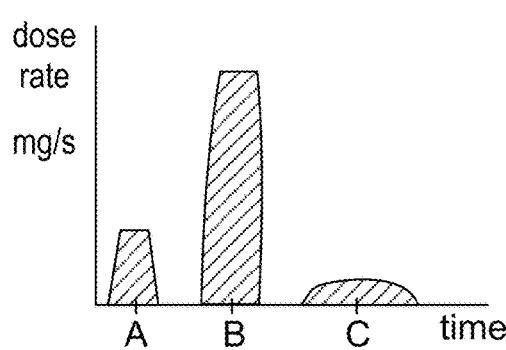
Figure 11D:
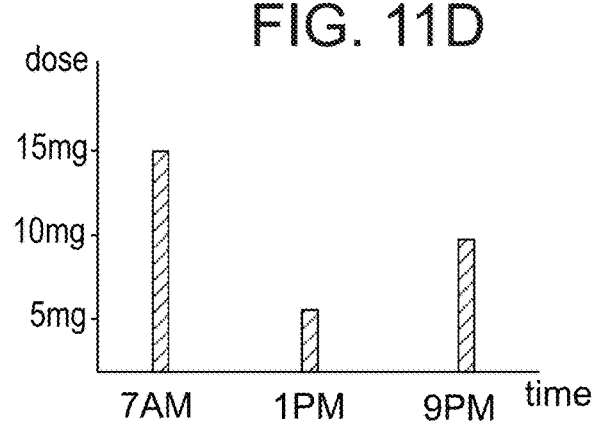
Figure 11E:
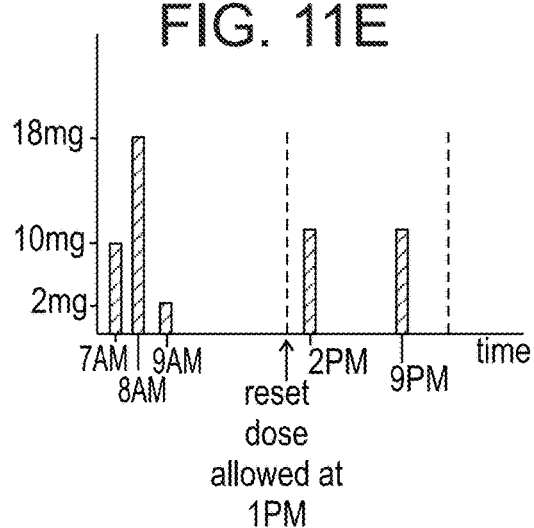

FIGS. 11A-11F illustrate various exemplary drug delivery regimens available using the inhaler, in accordance with an exemplary embodiment of the invention. FIGS. 11A-11C illustrate the administration of a single dose. FIGS. 11D-11E illustrate the administration of multiple doses. Optionally, each dose is delivered according to FIGS. 11A-11C.

FIG. 11A illustrates the continuous administration of a single dose. Optionally, the dose is provided during a single inhalation period, as shown by curve A, for example, by vaporizing the entire dose at a relatively high rate (e.g., shown as milligrams per second). Potentially, the user obtains the entire dose during one inhalation, beneficial for patients that find the inhalation uncomfortable and/or that need fast relief. Alternatively, the inhaler continues to vaporize the material at a continuous rate, as shown by curve B for example, by vaporizing at a relatively slow rate. Potentially, by continuously releasing vapors, the inhaler allows the patient to slowly inhale the drug at leisure over a longer period of time.

FIG. 11B illustrates the administration of a single dose in 'burst' form, divided into a plurality of sub-doses. Optionally or additionally, the sub-doses are substantially equal in amount. Optionally, sub-doses are administered only during inhalation, for example, as shown by different lag times separating the sub-doses in the figure. Alternatively, sub-doses are administered during set intervals, for example, every 15 seconds. The patient can inhale during the set times, for example being notified to inhale by audio or visual messages (e.g., beep or flashing light), and/or can wait to see the vapor rising from the mouthpiece, and then inhale.

FIG. 11C illustrates the administration of a single dose delivered as a plurality of sub-doses, each dose being adjusted according to the inhalation. Optionally, the total amount of drug delivered in each sub-dose and/or the rate of delivery is adjusted according to the inspiration of the patient. Optionally, sub-doses are delivered until the total dose has been delivered. For example, sub-dose A represents an average dose inhaled during an average inspiratory cycle. For example, sub-dose B represents a relatively higher dose delivered and/or a relatively higher dose rate, for example delivered during a strong inspiration, such as a patient in pain needing immediate relief. For example, sub-dose C represents a relatively lower sub-dose amount and/or delivered at a relatively lower rate, for example, during a weak inspiration, such as for a patient with lung problems.

FIG. 11D illustrates a dosing profile, in which the dose amount and/or dose time is preset. For example, at 7 AM, the patient is prescribed 15 mg of the drug. For example at 1 PM, the patient is prescribed 5 mg of the drug. For example, at 9 PM the patient is prescribed 10 mg of the drug. Optionally, the patient has a time limit window during which the dose can be administered, for example, 1 minute, 5 minutes, 15 minutes, or other smaller, intermediate or larger time periods are used.

FIG. 11E illustrates a dosing profile, in which the maximum dose allowed is allocated for a period of time. The patient is free to choose how the drug dose is distributed during the time period, for example, on an 'as needed' basis. For example, from 7 AM to 1 PM, 20 mg have been allocated. The patient chose to take 10 mg at 7 AM and 18 mg at 8 AM. The patient only had 2 mg remaining, which were taken at 9 AM. The patient had to wait until 1 PM for the drug dose to reset. The patient then took 10 mg at 2 PM and another 10 mg at 9 PM.

Figure 11F:
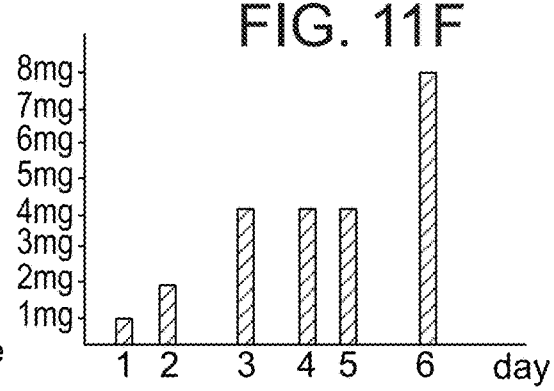

FIG. 11F illustrates a dosing profile, in which the dose is titrated up over time, for example, prescribed by the physician in response to the effect on the patient. The titration can be preset, for example, by the physician programming the prescription into the central database. Alternatively or additionally, the patient reports back to the physician (e.g., by phone, in person, by a request through the central system), and the physician titrates the doses accordingly. For example, the patient is initially allocated 1 mg per day, which is taken on day 1. The patient continues to experience pain, and is allocated 2 mg for the next day. The patient sends another request due to severe pain, and is allocated 3 mg. The patient is stable on days 3-5 on 3 mg, but then experiences pain again. The physician expecting the pain, has already preauthorized 8 mg to the patient.

In some embodiments, the dose profile is titrated down, for example, for a patient trying to quit smoking and/or narcotics (e.g., methadone). For example, the daily allowed nicotine level is slowly reduced, optionally based on side effects experienced by the patient (e.g., to prevent the side effects).

The control of allowing the patient an allocated dose, which is only provided during set time periods and/or during inhalation is potentially useful, for example, to control the use of restricted materials which people might share, and to prevent abuse of the drug.

Exemplary Method and Device for Delivery of Two or More Substances

Figure 12:
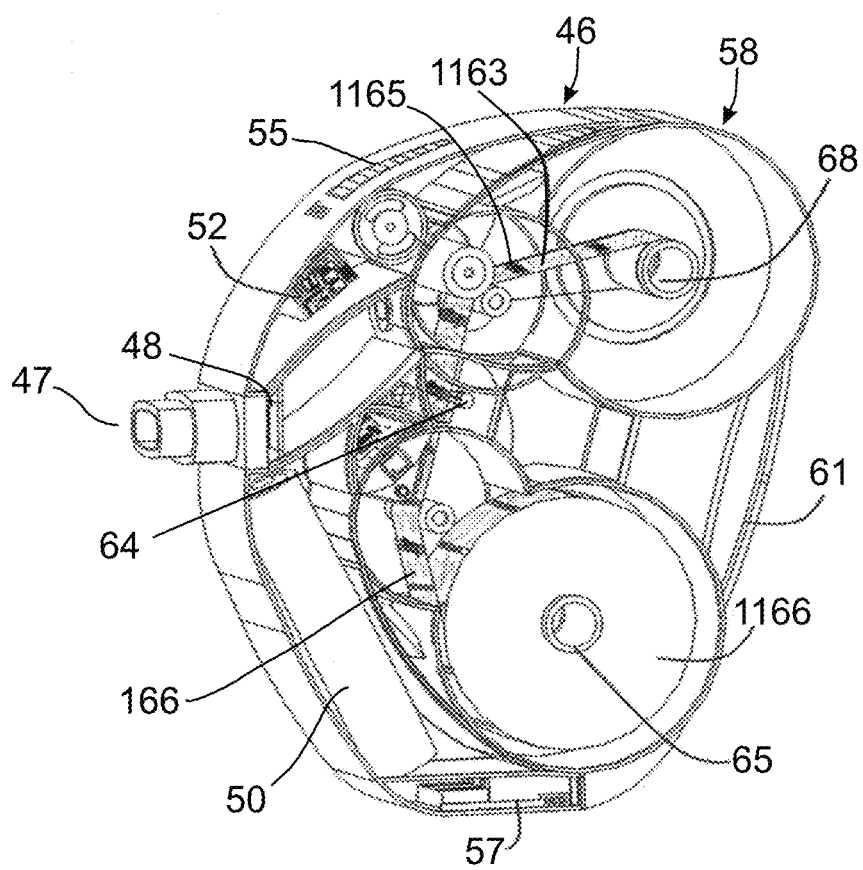
FIG. 12 is a schematic of a drug delivery device for extracting two or more different substances, in accordance with some embodiments of the invention.

FIG. 12 illustrates the inhaler (e.g., comprising base unit 46 and cassette 58), used for delivery of two or more active substances from two or more types packed materials, in accordance with some embodiments of the invention. In a non-limiting example, one substance is medical *Cannabis*, and the second substance is medical cocaine. In another example, two different strains of medical *Cannabis* are used. Potentially, concurrent administration (e.g., at the same time, close in time) results in a synergistic pain reduction effect, relatively higher than would be available with each drug alone.

In some embodiments of the invention, the inhaler designed for administration of a single substance is used, the two substances being provided by the tape, for example, by programming of the controller. In some embodiments of the invention, a tape 166 comprises two or more substances, for example, a first material 165 releases a first drug and a second material 163 releases a second drug. Optionally, materials 165 and 163 alternate relative to the long axis of tape 166. Optionally, the individual sections of material 165 and/or 163 deliver substantially equal doses per section, optionally different doses for the different drugs. Alternatively, individual sections of material 165 and/or 163 deliver different amounts, for example, being thicker and/or longer, for example, if the dose per session is being titrated up.

In some embodiments of the invention, the dose of each drug released is related to the pattern of materials 165 and 163 on tape 166. Optionally, thermal element 64 vaporizes contiguous sections of tape 166, vaporizing material 165 or 163, followed by the other material.

In some embodiments of the invention, the dose of each drug released is according to continuous movement of the pattern of materials 165 and 163 on tape 166. Optionally, thermal element 64 is selectively turned on and off (e.g., by the controller) to adjust the proportion of drugs released. For example, only the first drug can be released, for example, by activating thermal element 64 corresponding to locations of material 165 and turning off element 64 corresponding to locations of material 163. For example, the dose of the first drug can be doubled while the dose of the second drug is maintained, for example, by activating element 64 corresponding to every location of material 165, but activating element 64 corresponding to every other location of material 163.

In some embodiments of the invention, two or more drugs are released simultaneously. For example, using a tape divided along the long axis into two or more sections, each section comprising a different source material and releasing a different drug. Optionally, a single thermal element is used. Activating element applies heat to the tape, releasing the two drugs according to the structure of the tape. Alternatively, two or more thermal elements are used, for example, an array of thermal elements. Each element is independently activated and temperature controlled (e.g., by the controller), allowing control over the dosing profile of each drug, for example, each material may require a different temperature and/or heating time. Optionally or additionally, two or more spooling mechanisms are used corresponding to two or more different tapes. The two or more tapes can be moved independently over the heating element. Potentially, the amount of skipped or unused drug is reduced.

In some embodiments of the invention, an inhaler design allows the insertion and/or use of two or more cassettes simultaneously, for example, the inhaler base contains two or more access ports. Optionally, the inhaler and/or cassettes are put together at the pharmacy. Optionally, each cassette releases one drug. Optionally, each cassette is controlled independently. In a non-limiting example, one cassette contains a restricted substance and one cassette contains an unrestricted substance. A potential advantage of two or more cassettes is that only the drug that ran out needs to be replaced.

Additional Embodiment

Figure 16:
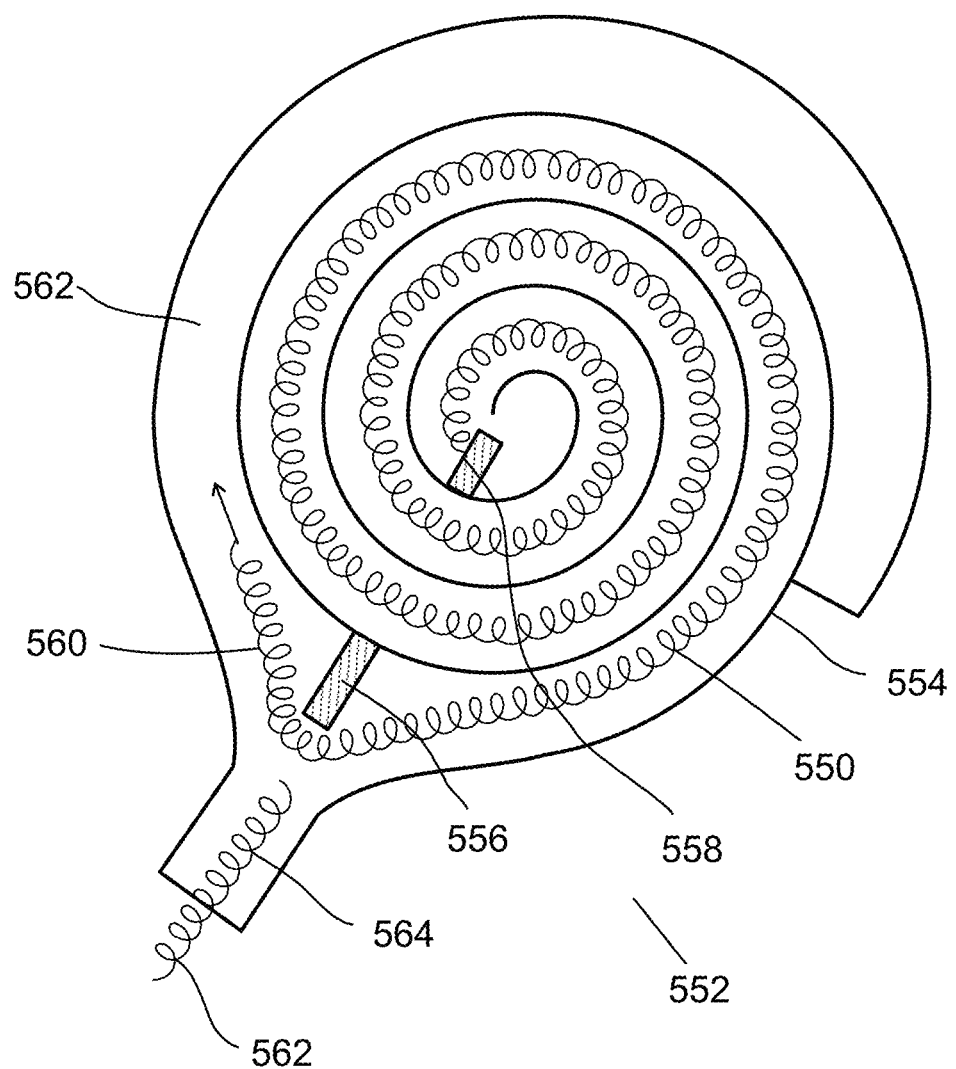
FIG. 16 is another embodiment of the device, in accordance with some embodiments of the invention.

FIG. 16 illustrates another embodiment of an inhalation device 552. In some embodiments of the invention, plant matter 550 is stored in a maze like structure, for example, a spiral shaped 554 container and/or tube. Optionally, matter 550 has been placed inside spiral 554, for example, in a granular material-like and/or compressed form. Alternatively, matter 550 is in the form of a tape, for example, as described herein.

In some embodiments of the invention, matter 550 is pushed towards a heating element 556, for example, pushed by a pushing element 558. Element 558 moves along spiral 554 pushing matter 550 from behind, for example, element 558 is powered by a small motor, and moves along optional tracks.

In some embodiments of the invention, residual matter 560 (e.g., after being heated) moves (e.g., pushed by advancing matter 550) into storage chamber 562.

In some embodiments of the invention, vapors 562 comprising the active substances are inhaled by use of mouthpiece 564.

Alternatively, in some embodiments of the invention, heating element 556 is moved inside spiral 554 (e.g., by small motor on optional tracks), releasing vapors 562 from plant matter 550, for example, element 556 moves towards the center of spiral 554. Optionally, pushing element 558 is not required.

Tamper

Referring back to FIGS. 2, 3 and 4A-B, in an exemplary embodiment of the invention, the drug delivery device comprises one or more elements to detect and/or prevent tampering with the drugs stored therein, for example, trafficking of *Cannabis*.

In an exemplary embodiment of the invention, tampering includes unauthorized use of the device, for example, sharing with others, attempts to increase dosage and/or excessive usage. Alternatively or additionally, tampering includes physical interference with the device itself. Anti-tampering methods can be classified as positive, for example, triggering, or negative, for example, tamper detection.

In an exemplary embodiment of the invention, base unit 93 comprises an identifier 97 for communicating the ID of base 93 to system 120, for example, a barcode. Optionally or additionally, cassette 94 comprises identifier 100 for communicating the ID of cassette 94 to system 120, for example, a barcode. Alternatively or additionally, unit 93 and/or cassette 94 comprise a communication port (e.g., physical port such as USB and/or wireless transmitter) for wireless communication with system 120. Optionally, system 120 provides remote monitoring and/or control of the device, for example by drug enforcement agencies, for example; track the location (e.g., through a GPS module), track the usage (e.g., as described herein), track the assembly or disassembly of unit 93 and cassette 94 (e.g., detect disassembly of cassette 94 without subsequent detection of refill or disposal).

In some embodiments of the invention, some breaches are not reported to the authorities, for example, repeated attempts to increase the dose, for example, non-illegal attempts. Optionally, relatively minor breaches are reported to personnel such as the patient's physician, who can try to work with the patient to resolve problems before the problems escalate. For example, the patient may need higher doses, but was too afraid to ask.

In an exemplary embodiment of the invention, inhaler 1000 comprises one or more intrusion detection sensors 70, for example, to detect physical interference. Optionally sensor 70 is a pressure sensor, for example, to detect opening of cassette 94 by a reduction in pressure of pressure of the cover against the sensor due to remove of the cover and/or by excessive pressure due to attempts to break the cover. Alternatively or additionally, sensor 70 is a temperature sensor that detects temperature increases suggesting unauthorized heating or burning of tape 63, for example, when element 64 is not activated. Alternatively or additionally, sensor 70 is a movement sensor, for example, coupled to one or more tape moving mechanisms (e.g., motor 53, mechanics 54, mechanics 62, reel 65, slip belt 67, spooling mechanism 72, intact reel 68) to detect unauthorized movement of tape 63, for example, trying to forcibly remove tape 63 from cassette 58.

In some embodiments of the invention, the module is smart enough to not accept 'inappropriate commands' from the inhaler, for example, upper limits to requests for high doses and/or long dosing periods. Such rules may be fixed and/or programmable. Potentially, the 'smart' module prevents more sophisticated tampering, for example, hacking of the inhaler.

In some embodiments of the invention, the modules are color coded.

In an exemplary embodiment of the invention, tracing transceiver module 56 on base unit 46 communicates with tracing module 69 on cassette 58. Optionally, communication occurs when cassette 58 has been inserted into base unit 46, for example, by a physical link. Optionally, module 56 verifies the identity of cassette 58 through module 69, for example, by comparing a code and/or ID to the expected code and/or ID (e.g., encrypted ID). Alternatively or additionally, module 69 verifies the identity of base unit 46 through module 56. Optionally, verification that cassette 58 is authorized to work with unit 46 triggers controller 52 to release drugs.

In an exemplary embodiment of the invention, physical tampering with unit 93 and/or cassette 94 triggers an optional sensor that raises an alarm with system 120. Optionally or additionally, drug enforcement agency 115 is notified. Optionally, physical tampering prevents registration of any ensuing doses, for example, by disabling the controller function of recording the doses. Alternatively or additionally, physical tampering is detected when the patient returns the cassette for resupply.

In some embodiments of the invention, the breach is detected indirectly, for example, by comparing the actual usage as tracked by the controller, to the usage claimed by the patient, for example, obtained through a survey. Optionally, patient 106 is requested to access patient domain 109 for example using a personal computer 110,103, with his/hers inhaler base unit 105,93 within a predetermined period post administration, for example, to fulfill surveys or specific researches on the effects of the drug. Optionally, breach is suspected, for example, if patient 108 claims to meet requirements by the data provided by the patient, yet the log data in inhaler base unit 93 discloses data which indicates breach of cassette 94, for example, logged doses without cassette 94 ID 100. Optionally, enforcing authorities 115 are notified via enforcement domain 116 to proceed with a nation specific investigative routine.

In some embodiments of the invention, breach and/or unlawful use of the device is detected by analyzing data, for example, uploaded by the patient. Optionally, the patient, wishing to replenish his/hers prescription, communicates with the distribution center remotely or physically by using the delivery device and/or the cassette. During the communication, and/or in conjunction with downloading and/or uploading medical data, any doses, registered and/or unregistered, indicating abuse and/or trafficking, will be detected by the database. Optionally, the suspected data is made accessible and/or forwarded to the relevant authorities, for example, according to nation specific regulations.

In some embodiments, reported time stamped doses, serve as a digital record to defend or prosecute accused patients, for example, involved in accidents operating heavy machinery or driving. Alternatively, time stamped doses are used to provide a warning that it is unsafe to drive and/or operate heavy machinery. Optionally or additionally, the device acts as a timer to let the user know when they can act safety again. Alternatively or additionally, user surveys and/or cognitive tests are administered to the user by web or phone to evaluate the ability to safely drive and/or operate heavy machinery Since contemporary chemical analysis tools are unreliable in some cases for determining recent drug usage (e.g., inaccurate temporally and/or quantitatively, as *Cannabis* levels remain high in the blood even 2 weeks after use), the time stamped doses can provide a more accurate picture.

In some cases, enforcing authorities 115 may request to inspect cassette 94 used by patient 108. Optionally, the dose tape is recovered. Optionally, inspection of the dosing tape allows verification if any tampering or abuse of the controlled substance has taken place, for example, by analyzing if the vaporized patterns of the tape differ from those expected to be produced by the heating element (e.g., if vaporized by an external source of heat).

Potentially, allowing the drug enforcing agencies and/or policing authorities complete tracing capabilities of the raw material distributed, will enable rapid widespread implementation of new and existing treatment using controlled substances, for example, medical *Cannabis*.

In some embodiments of the invention, the delivery device comprises a module with firmware upgradeable capabilities storing the unique identifier. Optionally, unique identifiers are periodically changed, potentially continuously or during set intervals, preventing electronic replication and/or abuse of cassettes 94, for example, by preventing any sustainable replications of the unique identifier. Optionally, the firmware is upgraded through the computer interface elements. Optionally, the firmware update is transferred to cassette 94 through inhaler base unit 93, potentially increasing the difficulty in hacking the system.

In a non-limiting example, at least some of the communication and/or functions between inhaler base unit 93 and cassette 94 occur as described, for example, in U.S. Pat. No. 7,819,116, the disclosure of which is incorporated herein by reference in its entirety.

Refill Supply

Referring back to FIGS. 2 and 3, in an exemplary embodiment of the invention, once cassette 94 is consumed, or nearly consumed to the extent set by specific national regulations, the patient may contact and/or approach distribution center 106 to request resupply.

In an exemplary embodiment of the invention, once patient has completed the use of cassette 94, for example, the organic material has been consumed, and/or the patient completed the treatment regimen, the patient disengages cassette 94 from inhaler base unit 93. Alternatively, cassette 94 is left engaged with base unit 93. Optionally, patient disposes of cassette 94. Alternatively, cassette 94 and/or combined cassette 94 and unit 93, are returned to distribution center 106, for example, dependent on nation specific regulations.

In an exemplary embodiment of the invention, returned modules are recycled, for example, sent to a recycling system. Optionally, the remaining tape is analyzed and kept for future evidence. Alternatively, the remaining plant material is destroyed. Optionally, the cassette and/or material support structure of the tape are cleaned and/or sterilized for another use, by the same patient or by another patient. Alternatively, some parts are not reused and are optionally recycled and/or replaced, for example, the mouthpiece, the desiccator, the mesh covering the plant material of the tape.

In an exemplary embodiment of the invention, resupply is requested in person by the patient. Optionally, distribution center 106 interfaces the patient's inhaler base unit 93 to distribution terminal 99,104, for example, by a physical connection with distribution terminal 99,104, and/or any other suitable means, for example, by direct contact. Optionally, distribution center 106 downloads the logged usage data from inhaler base unit 93, to distribution domain 107, which in turn stores it in main database 119. Optionally, the data from inhaler base unit 93 is verified for compliance with nation specific resupply regulations, for example, the number of fully logged doses is not below the threshold for resupply. Optionally, distribution center 106 issues the patient a new cassette 94.

In some embodiments of the invention, patient 108 requests resupply remotely, for example, by interfacing his/her inhaler base unit 105,93 to his/her personal computer 103,110, and/or smartphone, and communicating with main database 119 via patient domain 109. Alternatively, unit 105 directly communicates with domain 109, for example, wirelessly. Optionally, patient 108 proceeds to distribution center 106 without inhaler base 93, or alternatively cassette 94 is delivered directly to the patient.

In an exemplary embodiment of the invention, patient 108 issuing a resupply request that does not comply with the resupply regulations, is refused resupply until he/she meets the requirements for resupply. Optionally, refusal is automatic, for example, by a computer checking the request against the resupply regulations. Optionally, the computer provides a reason to the patient for the refusal, and/or a way to appeal the request. Optionally or additionally, refusal is manual, for example, by a worker manually checking the request against the guidelines. Optionally or additionally, refusal is partial, for example, the user is provided the allowed supply but refused the additional supply.

Update

In an exemplary embodiment of the invention, one or more stakeholders are involved with the development of new software and/or firmware, for example, for the control module of the inhaler base unit. Optionally, one or more entities contribute their software requirements for period upgrades. Optionally, every predetermined period one or more inhaler base units interface with the main database to download the new firmware automatically to update the control module software. In some embodiments of the invention, the vaporizing processes are updated, which may include, for example, modifications in one or more of the involved elements of the vaporization process, such as an improved algorithm to synchronize heating with tape movement and/or new rules for drug usage.

Feedback

In an exemplary embodiment of the invention, inhaler base unit 93, 105 transmits one or more data parameters collected during drug delivery, for example, to central database 119. Optionally, unit 93 is interfaced with a personal computer 103, 110 and/or any suitable mobile device (e.g., smartphone) via USB interface 95 and/or any other suitable wired and/or wireless communication protocol. Optionally, inhaler base unit 93,105 initiates a kiosk on personal computer 103,110 and/or mobile device which communicates with patient domain 109 to perform one or more functions, for example, reporting dose usage, placing renewal orders, complete surveys and/or research on the use of the drug and/or communication with prescribing physician 111.

In some embodiments of the invention, feedback is provided before inhalation, for example, that the user is about to start. Alternatively or additionally, feedback is provided during inhalation, continuously throughout the inhalation or during some periods, for example, the usage of the user. Alternatively or additionally, feedback is provided after inhalation.

In some embodiments of the invention, data downloaded from the inhalation device may assist in clinical research and/or drug development. In a non-limiting example, the period from which patient reports the effects of the drug may be provided for example, by filling out a survey. The provided data is compared to the actual time stamped administration, for example, to increase the ability to measure the interactions of one or more substances, such as cannabinoids, terpenoids and/or flavonoids derived from various strains of *Cannabis* with the human body. Potentially, evidence of clinical effectiveness will increase widespread adoption of new and existing treatments, and/or stimulate research and development beyond a limited number of specific strain compositions by making it easier to surmount the rigorous pharmaceutical regulatory process.

Potentially, a strict logged and/or orderly administration system involving direct patient input, spanning the entire supply process from raw material composition to the exact time and administrated dose, will allow the medical and academic institutions to access a vast highly detailed dynamic database, potentially opening up an unprecedented opportunity to derive accurate predictions and/or evidence on the interactions of the complexities of plant complexes with the human body. Potentially, the effects of restricted substance will be easier to study.

Exemplary Method of Manufacturing Tape

Figure 13:
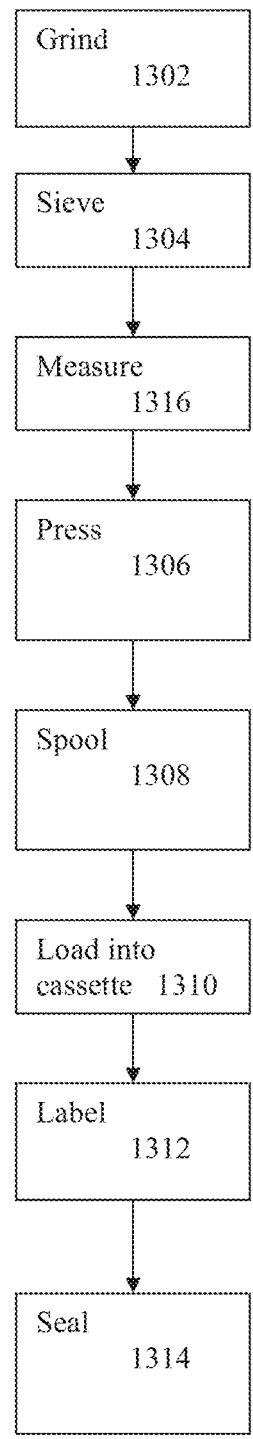
FIG. 13 is a flowchart of a method of manufacturing the tape, in accordance with an exemplary embodiment of the invention.

FIG. 13 is a flow chart of a method of manufacturing a tape of plant matter, in accordance with an exemplary embodiment of the invention.

Optionally, at 1302, the raw plant matter is ground to preserve the active substance, for example, without breaking the tricomes of the *Cannabis*. In a non-limiting example, one tape comprises 10 grams of government approved medical grade dried *Cannabis flos*, comprising of 20% THC and 5% CBD. Alternatively or additionally, other methods are used to transform the matter into granular form, non-limiting examples include one or more of; slicing, application of ultrasonic energy, application of a centrifugal force, separation by cooling, application of air pressure, application of a direct physical force.

Optionally, at 1304, the material is sieved. Optionally or additionally, the material is sieved sequentially. Optionally or additionally, sieving is performed using apertures of different diameters. Optionally, the sieving is performed with decreasing and/or increasing aperture diameters. In some embodiments of the invention, sieving isolates small particle of the plant material. In a non-limiting example, The *Cannabis flos* is sieved in sequential sieves of the following diameters: 700 μm, 500 μm and 100 μm. The resulting *Cannabis flos* is comprised of 6 grams of particles sized 700 μm-500 μm, and 4 grams of particles sized 500 μm-100 μm. Alternatively or additionally, one or more other methods are used to obtain a granular material with a selected range of particle sizes, non-limiting examples include; centrifugal separation, static electricity attraction, air pressure and/or ultrasonic separations (e.g, particles with mass/size smaller than the selected value will be blown to a different chamber).

At 1316, the concentration of active material in the material is measured. Optionally, the particles of the plant are first mixed to form a substantially homogenous mixture. Optionally, measurement is performed by taking one or more samples from the material, and analyzing the substance contents of the sample, for example, using suitable lab techniques, non-limiting examples include; high pressure liquid chromatography, gas chromatography, mass spectrometry, thin layer chromatography.

At 1306, the particles of plant material are pressed into a tape. For example, the tape is a relatively long strip, or the tape is in the shape of a disc. Optionally, the pressing occurs against a material backing layer. Optionally, the pressing is done in a homogenous manner, for example, the pressed material is vibrated to evenly level the particles on the backing layer. Alternatively or additionally, one or more methods are used to form the granular material into a specific shape and/or density, non-limiting examples include; rotating cylindrical press, air pressure, centrifugal force.

In some embodiments of the invention, the measured concentration per unit volume and/or weight (e.g., as in 1316) is used to form a baseline. Optionally, the baseline measurement is used to form the tape with predetermined concentrations, for example, substantially uniform doses and/or varying doses. Alternatively, the baseline measurement is used to estimate the doses in the tape after the plant material has been formed into the tape, for example, to estimate the variation in the doses along the tape and/or to estimate the consistency of the doses along the tape.

In an non-limiting example, the backing layer is a 316 type steel mesh with 56 μm hole diameter, and 0.05 mm wire thickness is cut into a 29.5 mm wide by 2,000 mm long strips. The sieved *Cannabis flos* is homogenously laid out on the entire length of the steel mesh strip which is housed in an anchored mold, the entire assembly is vibrated, leveling the resulting *Cannabis flos* on the steel mesh strip substantially evenly. The entire assembly is pressed until obtaining a combined thickness of 0.6 mm, resulting in a stacked layer segment of tape, for example, as illustrated in FIG. 6A. The density of *Cannabis* is 30%, with the rest being empty space between the particles. A further 29.5 mm wide by 2,000 mm long and 0.01 mm thick strip of inert material is placed on top of the *Cannabis flos* layer, resulting in a stacked layer segment, for example, as illustrated in FIG. 6B.

In some embodiments of the invention, the source material (e.g., plant matter) is mixed with an adhesive, for example, an inert, biocompatible and/or flexible material, for example, FDA compliant high temperature thixtropic adhesive silicone sealant. Optionally, the mixture is poured into a tape shaped mold. Alternatively, the adhesive is poured over the mold with the source material already laid out. Optionally, the adhesive is cured at room temperature. Optionally or additionally, the mixture is perforated to allow vapors to escape during heating.

In some embodiments of the invention, the source material is bound to an inert layer, for example hemp paper. Optionally, the binding is done with an inert, biocompatible and/or flexible adhesive. Potentially, the inert layer contacts the heating element, and the inert layer transfers the heat to vaporize the plant matter.

In some embodiments of the invention, the tape is prepared using a mold having vertical partitions, for example the partitions are about 1 mm high and/or about 0.5 mm apart. Optionally, the source material is loaded into the mold while the partitions are spread or fanned out (e.g., angle <180 degrees). Optionally or additionally, after the source material is loaded, the partition angles are pushed together (e.g., angle >180 degrees). The change in orientation squeezes the source material in between the partitions.

In some embodiments of the invention, the flexible tape is stretched at least at the point of contacting the heating element. Potentially allowing for relatively more vapors to escape from the tape. Stretching can be accomplished by applying a suitable tension to the tape during packaging and/or spooling in the device.

Optionally, at 1308, the tape is spooled into a roll. Alternatively, the tape (e.g., disc) is cut into doses. In a non-limiting example, the tape is spooled on a 30 mm diameter core, resulting in a rolled tape, for example, as depicted in FIG. 5A. Alternatively or additionally, one or more other methods are used to compact the material and mount the material on the packing medium, non-limiting examples include; fold, inject, lay, apply, bind.

Optionally, at 1310, the tape is loaded into a cassette.

Optionally, at 1312, the cassette is labeled. Non-limiting examples of labels include electronic (e.g., memory chip), optical (e.g., hologram), RF (e.g., RFID), magnetic (e.g., magnetic strip) and/or mechanical (e.g., Braille, QR code). Optionally, the unique identifier embedded in the cassette is loaded with the details of the tape. Optionally, the cassette is labeled with a visual label, for example, written text and/or a bar code. Non-limiting examples of loaded data include; the total weight of the raw material, the size of the particles, the strain of the material, the estimated amount of active substance per centimeter of tape, the thickness of the material, the density of the material, the temperature required to release one or more of the active substances, the speed of movement of the tape required to release a unit of the active substance. Potentially, labeling the cassette comprising the restricted substance allows for tracking and control of the substance.

Optionally, at 1314 the cassette is hermetically sealed, for example in a tamper proof manner.

In some embodiments of the invention, the method is used to manufacture a tape comprising a pharmaceutical and/or other synthetic composition of active substances releasable by application of heat. For example, one or more of 1316, 1306, 1308, 1310, 1312 and/or 1314 can be performed to manufacture the tape.

Potential Advantages of Some Embodiments

In some embodiments, effective therapeutic properties of the medication, for example, due to limited processing that preserves the natural active ingredients of the organic material.

In some embodiments, standardized raw material, for example, due to packaging of the material into known doses. In some embodiments of the invention, the concentration of the material is marked on the packaging, according to the measurements of the material during processing. Alternatively, the concentration of the material is pre-set.

In some embodiments, precise titration and dosage, for example, by the controller controlling the application of heat to vaporize a known amount of active material.

In some embodiments, safe non-combustive administration method, for example, by vaporization.

In some embodiments, convenient administration method, no user intervention prior to administration; automatic dose loading, cleaning, discarding of residual waste, for example, the patient simply inhales and the device does the rest.

In some embodiments, immediate and/or high efficacy, for example, due to lung deposition by inhalation, for example as compared to pills and/or sublingual sprays.

In some embodiments, affordability, for example, by using naturally grown plants as opposed to pharmaceutical solutions.

In some embodiments, traceable raw material with complete administration and logging, especially allowing use of restricted substances, for example, through the use of the tracking abilities of the system.

In some embodiments, the ability to provide repeatable drug doses of specific strains allows for improved treatment, for example, by providing drugs deemed to be most suitable for the patient's medical condition.

In some embodiments, mobile form factor, for example, allowing use of the device anywhere at anytime.

In some embodiments, applicable to patients with respiratory difficulties, for example, by automatic adjustment of dose delivery according to the breathing pattern of the patient.

In some embodiments, strict differentiation from the recreational market, especially for controlled substances, for example, designed for precise titration of doses.

In some embodiments, the possibility to introduce new medicine compositions frequently, enabling a rapid iteration product cycle. This allows flexibility for swiftly adapting the drug composition to specific patient physical properties, or specific symptoms. For example, by researchers having access to usage data and/or to conduct studies. The mix of drugs provided to the patient can be changed in real time, without requiring any patient interference or activity.

A solution for treating patients using medical *Cannabis* that is balanced, taking into account the needs of involved official stakeholders.

It is expected that during the life of a patent maturing from this application many relevant devices that deliver drugs by applying localized heat to plant matter will be developed and the scope of the term delivery device is intended to include all such new technologies a priori. As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

General

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of processing plant material which comprises one or more active substances into a layer unit for use in an inhaler device, the method comprising:
   grinding raw plant material, while maintaining a macroscopic plant structure by preserving trichomes of the plant material;
   sieving the ground plant material to obtain particles having a particle size between 100 um and 700 um; and
   pressing said particles into a mold which comprises a semi-permeable layer to form a layer unit of a cartridge, wherein said particles are squeezed against vertical partitions of said mold, said layer unit having a uniform thickness, wherein an amount of said particles in said layer unit corresponds to a single dose of said one or more active substances.

2. The method according to claim 1, comprising measuring a concentration of said one or more active substances in said particles.

3. The method according to claim 2, wherein said measuring comprises analyzing a sample of said particles using one or more techniques selected from the group consisting of: high pressure liquid chromatography, gas chromatography, mass spectrometry and thin layer chromatography.

4. The method according to claim 1, wherein said grinding preserves said one or more active substances in their natural form.

5. The method according to claim 1, wherein said plant material comprises medical grade dried *cannabis* flos.

6. The method according to claim 5, wherein said one or more active substances comprise one or both of tetrahydrocannabinol (THC) or Cannabidiol (CBD).

7. The method according to claim 1, wherein said grinding does not break said trichomes.

8. The method according to claim 1, wherein said pressing comprises compressing said particles into a density of between 10-50% plant matter.

9. The method according to claim 1, comprising, prior to said pressing, vibrating said particles to form a homogenous layer having air spaces between said particles.

10. The method according to claim 2, further comprising labeling said layer unit with the measured concentration of said one or more active substances.

11. The method according to claim 2, further comprising labeling said layer unit with one or more of: the strain type of said plant material, the strain composition of said plant material, or expiration date of said plant material.

12. The method according to claim 1, wherein said sieving is performed using apertures of different diameters.

13. The method according to claim 1, further comprising connecting said layer unit to an inert layer, thereby forming a stacked layer structure.

14. The method according to claim 1, wherein said semi-permeable layer comprises apertures small enough to contain said trichomes and large enough to allow said one or more active substance to escape said layer unit when vaporized.

15. The method according to claim 14, wherein said semi-permeable layer comprises a mesh.

16. The method according to claim 14, wherein said semi-permeable layer is resistive and acts as a thermal emitter configured for directly heating said unit layer by contact.

17. The method according to claim 14, further comprising coupling said layer unit, at an opposite surface of said layer unit, to form a second semi-permeable layer.

* * * * *